US006797466B1

(12) United States Patent
Bult et al.

(10) Patent No.: US 6,797,466 B1
(45) Date of Patent: Sep. 28, 2004

(54) **COMPLETE GENOME SEQUENCE OF THE METHANOGENIC ARCHAEON, *METHANOCOCCUS JANNASCHII***

(75) Inventors: Carol J. Bult, Bar Harbor, ME (US); Owen R. White, Gaithersburg, MD (US); Hamilton O. Smith, Baltimore, MD (US); Carl R. Woese, Urbana, IL (US); J. Craig Venter, Rockville, MD (US)

(73) Assignees: The Institute for Genomic Research, Rockville, MD (US); Johns Hopkins University, Baltimore, MD (US); The Board of Trustees of the University of Illinois, Urbana, IL (US)

( * ) Notice: Subject to any disclaimer, the term of this patent is extended or adjusted under 35 U.S.C. 154(b) by 137 days.

(21) Appl. No.: 09/692,570

(22) Filed: Oct. 20, 2000

Related U.S. Application Data

(63) Continuation of application No. 08/916,421, filed on Aug. 22, 1997.
(60) Provisional application No. 60/024,428, filed on Aug. 22, 1996.

(51) Int. Cl.$^7$ ................................................ C12Q 1/68
(52) U.S. Cl. ..................... 435/6; 435/320.1; 435/252.3; 435/325; 536/23.7; 536/24.32
(58) Field of Search .............................. 536/23.7, 24.32; 435/320.1, 325, 252.3, 64.1, 6

(56) References Cited

U.S. PATENT DOCUMENTS

| | | |
|---|---|---|
| 4,431,739 A | 2/1984 | Riggs |
| 4,601,980 A | 7/1986 | Goeddel et al. |
| 5,518,911 A | 5/1996 | Abo et al. |
| 5,919,620 A * | 7/1999 | Brodeur et al. ................. 435/6 |

OTHER PUBLICATIONS

GIBCOBRL, 1993–1994 Catalogue and Reference Guide, pp. R–114.*
Robert D. Fleischmann et al., Science, vol. 269 Jul 28, 1995, pp. 496–520.*
Akio Adachi et al., Journal of Virology, Aug. 1986, pp. 284–291.*
Almond et al., "Complementation of a thr–1 mutation of *Escherichia coli* by DNA from the extremely thermophilic archaebacteruim *Methanococcus jannaschii*," Appl. Microbiol. Biotechnol. 30:148–152 (1989).
Belay et al. "Dinitrogen fixation by a thermophilic methanogenic bacterium," Nature 312:286–288 (1984).
Bernad et al., "Structural and functional relationships between prokaryotic and eukaryotic DNA polymerases," EMBO J. 6(13):4219–4225 (1987).
Blaut et a., "Metaboism of methanogens," Antonie van Leeuwenhoek 66:187–208 (1994).

Brown et al., "Root of the universal tree of life based on ancient aminoacyl–tRNA synthetase gene duplications," Proc. Natl. Acad. Sci. USA 92:2441–2445 (1995).
Bult et al.., Science 273:1043–1045 and 1067–1072 (1996).
Cooper et al., "Protein splicing of the yeast TFP1 intervening protein sequence: a model for self–excision," EMBO J. 12(6):2575–2583 (1993).
Cooper et al., "Protein splicing: Self–Splicing of Genetically Mobile Elements at the Protein Level," TIBS 20:351–356 (1995).
Cullman et al., "Characterization of the five replication factor C genes of *Saccharomyces cerevisiae*," Mol. Cell. Biol. 15(9):4661–4671 (1995).
Delaure et al., "An attempt to unify the structure of polymerases," Protein Engineering 3(6):461–467 (1990).
De Pouplana et al., "Evidence that two present–day components needed for the genetic code appeared after nucleated cells separated from eubacteria," Proc. Natl. Acad. Sci. USA 93:166–170 (1996).
Dimarco et al., "Unusual coenzymes of methanogenesis," Annu. Rev. Biochem. 569:355–394 (1990).
Eberhart et al., "The pelota locus encodes a protein required for meiotic cell division: an analysis of $G_2/M$ arrest in Drosophila spermatogeneiss," Development 121:3477–3486 (1995).
Faguy et al., "Molecular analysis of aarchaeal flagellins: similarity to the type IV pilin—transport superfamily widwspread in bacteria," Can. J. Microbiol. 40:67–71 (1994).
Flieschmann et al., "Whole–genome random sequencing and assembly of *Haemophilus influenzae* Rd," Science 269:496–512 (1995).
Gavin et al., "Conserved initiator proteins in eukaryotes," Science 270:1667–1671 (1995).
GenBank report, "*B. thuringiensis* insertion element IS240–B protein gene, complete cds," Locus BACIS2402, Accession No. M23741 J03315 (1989), with associatd report for Locus Bank BACIS2401, Accession No. M23740 J03315 (1989).
GenBank report, "Insertion sequence IS982 (From *Lactococcus lactis*) transposase gene, c9mplete cds," Locus INSTRANB, Accession No. L34754 (1996).
Gogarten et al., "Evolution of the vacuolar $H^+$–ATPase: Implications for the origin of eukaryotes," Proc. Natl. Acad. Sci. USA 86:6661–6665 (1989).

(List continued on next page.)

*Primary Examiner*—Dave T Nguyen
*Assistant Examiner*—Richard Schnizer
(74) *Attorney, Agent, or Firm*—Human Genome Sciences, Inc.

(57) ABSTRACT

The present application describes the complete 1.66-megabase pair genome sequence of an autotrophic archaeon, *Methanococcus jannaschii*, and its 58- and 16-kilobase pair extrachromosomal elements. Also described are 1738 predicted protein-coding genes.

31 Claims, 2 Drawing Sheets

OTHER PUBLICATIONS

Hall et al., "Molecular cloning and primary structure of squid (*loligo forbesi*) rhodopsin, a phospholipase C–directed G–protein linked receptor," Biochem. J. 274 (Pt. 1):35–40; GenBank Accession No. X56788,. Dec. 21, 1994.

Hamilton et al., "Structure of genes and an insertion element in the methane producing archaebacterium *Methanobrevibacter smithii*," Mol. Gen. Genet. 200:47–59 (1985).

Hartman et al., "Uridine and dolichyl diphosphate activated oligosaccharides are intermediates in the biosynthesis of the S–layer glycoprotein of *Methanonthermus fervidus*," Arch. Microbiol. 151:274–281 (1989).

Hillier et al., "The WashU–Merck EST Project," GenBank Accession No. H46528, Jul. 31, 1995, Washington University School of Medicine, USA.

Hillier et al., "The WashU–Merck EST Project," GenBank Accession No. R07848, Apr. 5, 1995, Washington University School of Medicine, USA.

Hillier et al., "Washington University *Caenorhabditis briggsae* EST Project," GenBank Accession No. R04180, Mar. 31, 1995, Washington University School of Medicine, USA.

Hillier et al., "The WashU–Merck EST Project," GenBank Accession No. R08145, Apr. 5, 1995, Washington University School of Medicine, USA.

Hillier et al., "The WashU–Merck EST Project," GenBank Accession No. R15715, Apr. 13, 1995, Washington University School of Medicine, USA.

Hillier et al., "The WashU–Merck EST Project," GenBank Accession No. N21111, Dec. 19, 1995, Washington University School of Medicine, USA.

Hillier et al., "The WashU–Merck EST Project," GenBank Accession No. R96366, Sep. 11, 1995, Washington University School of Medicine, USA.

Hirata et al., "Molecular structure of a gene, VMA1, encoding the catalytic subunit of $H^+$–Translocating adenosine triphosphatase from vacuolar membranes of *Saccharomyces cerevisiae*," J. Biol. Chem. 265(12):6726–6733 (1990).

Iwabe et al. "Evolutionary relationship of archaebacteria, eubacteria, and eukaryotes inferred from phylogenetic trees of duplicated genes," Proc. Natl. Acad. Sci. USA 86:9355–9359 (1989).

Jiang et al., "Structure and sequence of the rfb (0 antigen) gene cluster of Salmonella serovar typhimurium (strain LT2)," Molec. Microbiol. 5(3):697–713 (1991).

Jones et al., "*Methanococcus jannaschii* sp. nov., an extremely thermophilic methanogen from a submarine hydrothermal vent," Arch. Microbiol. 136:254–261 (1983).

Kaine et al., "Isolation and characterization of the 7S RNA gene from *Methanococcus voltae*," J. Bacteriol. 171(8):4261–4266 (1989).

Kalmokoff et al., "Relatedness of the flagellins from methanogens," Arch. Microbiol. 157:481–487 (1992).

Kane et al., "Protein splicing converts the yeast TFP1 gene product to the 69–kD subunit of the vacuolar H+–adenosine triphosphatase," Science 250:651–657 (1990).

Klenk et al., "Archaea and eukaryotes versus bacteria?," Current Biology 4(10):920–922 (1994).

Köpke et al., "Comparative studies of ribosomal proteins and their genes from *Methanococcus vannielii* and other organisms," Can J. Microbiol. 35:11–20 (1989).

Langer et al., "Transcription in archaea: Similarity to that in eucarya," Proc. Natl. Acad. Sci. USA 92:5768–5772 (1995).

Lanzendorfer et al., "Structure and function of the DNA–dependent RNA polymerase of Sulfolobus," System. Appl. Microbiol. 16:656–664 (1994).

Lechner et al., "Organization and nucleotide sequence of a transcriptional unit of *Methanococcus vannielii* comprising genes for protein synthesis elongation factors and ribosomal proteins," J. Mol. Evol. 29:20–27 (1989).

Logan et al., "Crystal structure of glycyl–tRNA synthetase from *Thermus thermophilus*," EMBO J. 14(17):4156–4167 (1995).

Lutkenhaus, J. "*Escherichia coli* cell division," Curr. Opin. Genet. Devel. 3:783–788 (1993).

McCombie et al., "*Caenorhabditis elegans* expressed sequence tags identify gene families and potential disease gene homologoues", Nature Genet. 1:124–131; GenBank Accession No. M79739, (1992).

McCombie et al., "*Caenorhabditis briggsae* cDNAs," GenBank Accession No. T01773, Nov. 10, 1992, The Institute for Genomic Research, Rockville, MD, USA.

Michel et al., "Comparison of fungal mitochondrial introns reveals extensive homologies in RNA secondary structure," Biochimie 64:867–881 (1982).

Mojica et al., "Long stretches of short tandem repeats are present in the largest replicons of the Archaea *Haloferax mediterranei* and *Haloferax volcanii* and could be involved in replicon partitioning,": Molec. Microbiol. 17(1):85–93 (1995).

Perler et al., "Intervening sequences in an Archaea DNA polymerase gene," Proc. Natl. Acad. Sci. USA 89:5577–5581 (1992).

Pietrokovski et al., "Conserved sequence features of inteins (protein introns) and their use in identifying new inteins and related proteins," Protein Science 3:2340–2350 (1994).

Poritz et al., "Human SRP RNA and *E. coli* 4.5wS RNA contain a highly homologous structural Domain," Cell 55:4–6 (1988).

Riley et al., "Functions of the gene products of *Escherichia coli*," Microbiol. Rev. 57(4):862–952.

Rothfield et al., "How do bacterial decide where to divide?," Cell 84:183–186 (1996).

Sandman et al., "HMf, a DNA–binding protein isolated from the hyperthermophilic archaeon *Methanothermus fervidus*, is most closely related to histones," Proc. Natl. Acad. Sci. USA 87:5788–5791 (1990).

Schön et al., "Misaminoacylation and transamidation are required for protein biosynthesis in *Lactobacillus bulgaricus*," Biochimi 70:391–394 (1988).

Sevier et al., "Monoclonal antibodies in clinical immunology," Clin. Chem. 27(11):1979–1806 (1981).

Uemori et al., "The hyperthermophilic Archaeon *Pyrodictium occultum* has two α–like DNA polymerase," J. Bacteriol. 177(8):2164–2177 (1995).

Wagar et al., "The glycyl–tRNA synthetase of the *Chlamydia trachomatis*," J. Bacteriol. 177(17):5179–5185 (1994).

Whitbread et al., "Cdc54 belongs to the Cdc45/Mcm3 family of proteins which are esential for initiation of eukaryotic DNA replication," Gene 155:113–117 (1995).

Woese et al. "Towards a natural system of organisms: Proposal for the domains archaea, bacteria, and eucarya," Proc. Natl. Acad. Sci. USQ 87:4576–4579 (1990).

Wood et al., "The acetyl–CoA pathway: a newly discovered pathway of autotriphic growth," TIBS 11:14–18 (1986).

Xu et al., "In vitro protein splicing of purified precursor and the identification of a branched intermediate," Cell 75:1371–1377 (1993).

Zhao et al., "An extremely thermophilic Methanococcus from a deep see hydrothermal vent and its plasmid," Arch. Microbiol. 150:178–183 (1988).

International Search Report for International Application No. PCT/US97/14900.

* cited by examiner

COMPLETE GENOME SEQUENCE OF THE METHANOGENIC ARCHAEON, *METHANOCOCCUS JANNASCHII*

This application is a Continuation of U.S. application Ser. No. 08/916,421, filed Aug. 22, 1997, which is hereby incorporated by reference; said U.S. application Ser. No. 08/916,421 claims priority of U.S. Provisional Application No. 60/024,428, filed Aug. 22, 1996, which is hereby incorporated by reference.

Part of the work performed during development of this invention utilized U.S. Government funds. The U.S. Government may have certain rights in the invention—DE-FC02-95ER61962; DE-FCO2-95ER61963; and NAGW 2554.

BACKGROUND OF THE INVENTION

Statement as to Rights to Inventions Made Under Federally-Sponsored Research and Development 1. Reference to a Sequence Listing Provided on Compact Disc This application refers to a "Sequence Listing", which is provided as an electronic document on two identical compact discs (CD-R), labeled "Copy 1" and "Copy 2." These compact discs each contain the electronic document, filename "PB275C1.ST25.txt" (2,259,883 bytes in size, created on Nov. 14, 2002), which is hereby incorporated in its entirety herein.

2. Field of the Invention

The present application discloses the complete 1.66-megabase pair genome sequence of an autotrophic archaeon, *Methanococcus jannaschii*, and its 58- and 16-kilobase pair extrachromosomal elements. Also identified are 1738 predicted protein-coding genes.

3. Related Background Art

The view of evolution in which all cellular organisms are in the first instance either prokaryotic or eukaryotic was challenged in 1977 by the finding that on the molecular level life comprises three primary groupings (Fox, G. E., et al., *Proc. Natl. Acad. Sci. USA* 74:4537 (1977); Woese, C. R. & Fox, G. E., *Proc. Natl. Acad. Sci. USA* 74:5088 (1977); Woese, C. R., et al., *Proc. Natl., Acad. Sci. USA* 87:4576 (1990)): the eukaryotes (Eukarya) and two unrelated groups of prokaryotes, Bacteria and a new group now called the Archaea. Although Bacteria and Archaea are both prokaryotes in a cytological sense, they differ profoundly in their molecular makeup (Fox, G. E., et al., *Proc. Natl. Acad. Sci. USA* 74:4537 (1977); Woese, C. R. & Fox, G. E., *Proc. Natl. Acad. Sci. USA* 74:5088 (1977); Woese, C. R., et al., *Proc. Natl. Acad. Sci. USA* 87:4576 (1990)). Several lines of molecular evidence even suggest a specific relationship between Archaea and Eukarya (Iwabe, N., et al., *Proc. Natl. Acad. Sci. USA* 86:9355 (1989); Gogarten J. P., et al., *Proc. Natl. Acad. Sci. USA* 86:6661 (1989); Brown, J. R. and Doolittle, W. F., *Proc. Natl. Acad. Sci. USA* 92:2441 (1995)).

The era of true comparative genomics has been ushered in by complete genome sequencing and analysis. We recently described the first two complete bacterial genome sequences, those of *Haemophilus influenzae* and *Mycoplasma genitalium* (Fleischmann, R. D., et al., *Science* 269:496 (1995); Fraser, C. M., et al., *Science* 270:397 (1995)). Large scale DNA sequencing efforts also have produced an extensive collection of sequence data from eukaryotes, including *Homo sapiens* (Adams, M. D., et al., *Nature* 377:3 (1995)) and *Saccharomyces cerevisiae* (Levy, J., *Yeast* 10:1689 (1994)).

*M. jannaschii* was originally isolated by J. A. Leigh from a sediment sample collected from the sea floor surface at the base of a 2600 m deep "white smoker" chimney located at 21° N on the East Pacific Rise (Jones, W., et al., *Arch. Microbiol.* 136:254 (1983)). *M. jannaschii* grows at pressures of up to more than 500 atm and over a temperature range of 48–94° C. with an optimum temperature near 85° C. (Jones, W., et al., *Arch. Microbiol.* 136:254 (1983)). The organism is autotrophic and a strict anaerobe; and, as the name implies, it produces methane. The dearth of archaeal nucleotide sequence data has hampered attempts to begin constructing a comprehensive comparative evolutionary framework for assessing the molecular basis of the origin and diversification of cellular life.

SUMMARY OF THE INVENTION

The present invention is based on whole-genome random sequencing of an autotrophic archaeon, *Methanococcus jannaschii*. The *M. jannaschii* genome consists of three physically distinct elements: (i) a large circular chromosome; (ii) a large circular extrachromosomal element (ECE); and (iii) a small circular extrachromosomal element (ECE). The nucleotide sequences generated, the *M. jannaschii* chromosome, the large ECE, and the small ECE, are respectively provided on pages 153–586 (SEQ ID NO:1), pages 586–601 (SEQ ID NO:2), and pages 602–606 (SEQ ID NO:3).

The present invention is further directed to isolated nucleic acid molecules comprising open reading frames (ORFs) encoding *M. jannaschii* proteins. The present invention also relates to variants of the nucleic acid molecules of the present invention, which encode portions, analogs or derivatives of *M. jannaschii* proteins. Further embodiments include isolated nucleic acid molecules comprising a polynucleotide having a nucleotide sequence at least 90% identical, and more preferably at least 95%, 96%, 97%, 98% or 99% identical, to the nucleotide sequence of a *M. jannaschii* ORF described herein.

The present invention also relates to recombinant vectors, which include the isolated nucleic acid molecules of the present invention, host cells containing the recombinant vectors, as well as methods for making such vectors and host cells for *M. jannaschii* protein production by recombinant techniques.

The invention further provides isolated polypeptides encoded by the *M. jannaschii* ORFs. It will be recognized that some amino acid sequences of the polypeptides described herein can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

In another aspect, the invention provides a peptide or polypeptide comprising an epitope-bearing portion of a polypeptide of the invention. The epitope-bearing portion is an immunogenic or antigenic epitope useful for raising antibodies.

DETAILED DESCRIPTION OF THE INVENTION

Figure 1:
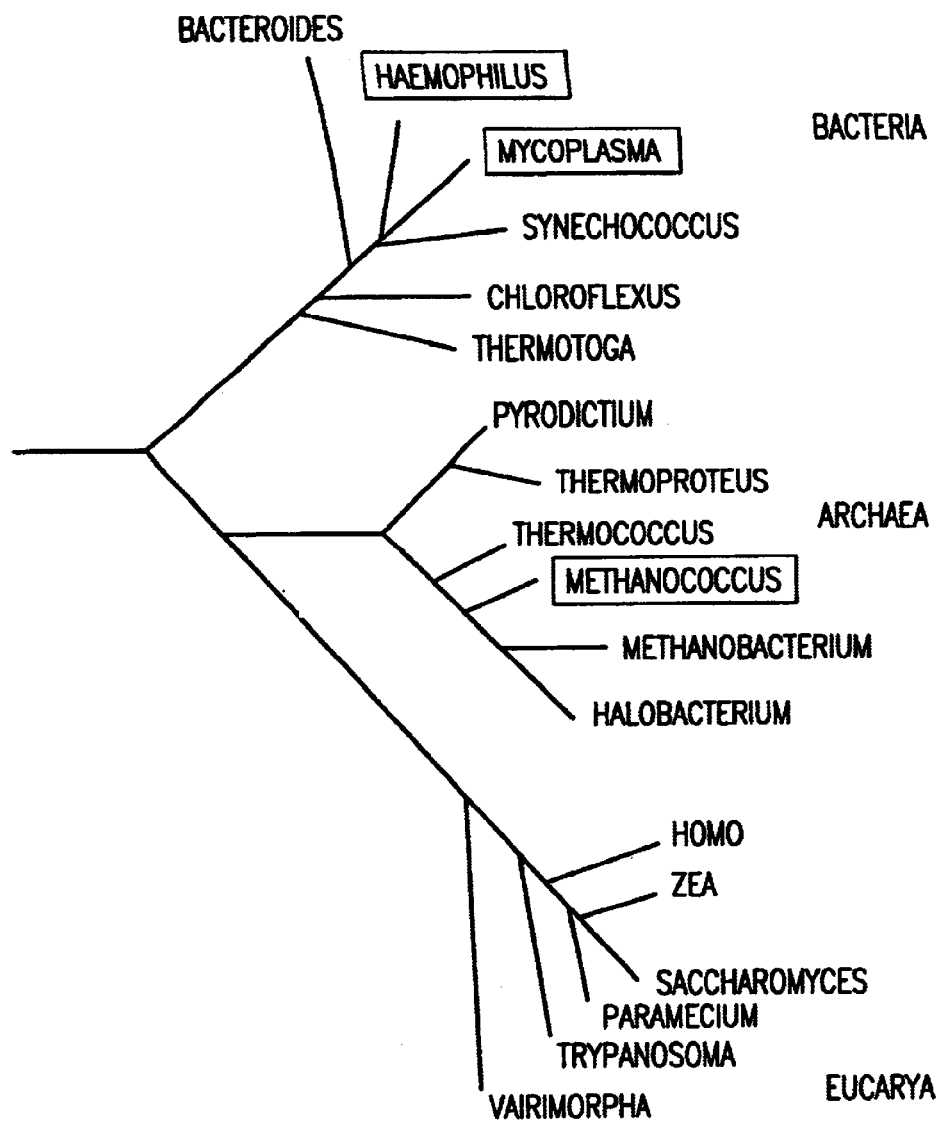
FIG. 1. A schematic showing the relationship of the three domains of life based on sequence data from the small subunit of rRNA (Fox, G. E., et al., Proc. Natl. Acad. Sci. USA 74:4537 (1977); Woese, C. R. & Fox, G. E., Proc. Natl. Acad. Sci. USA 74:5088 (1977); Woese, C. R., et al., Proc. Natl. Acad. Sci. USA 87:4576 (1990)).
Figure 2:
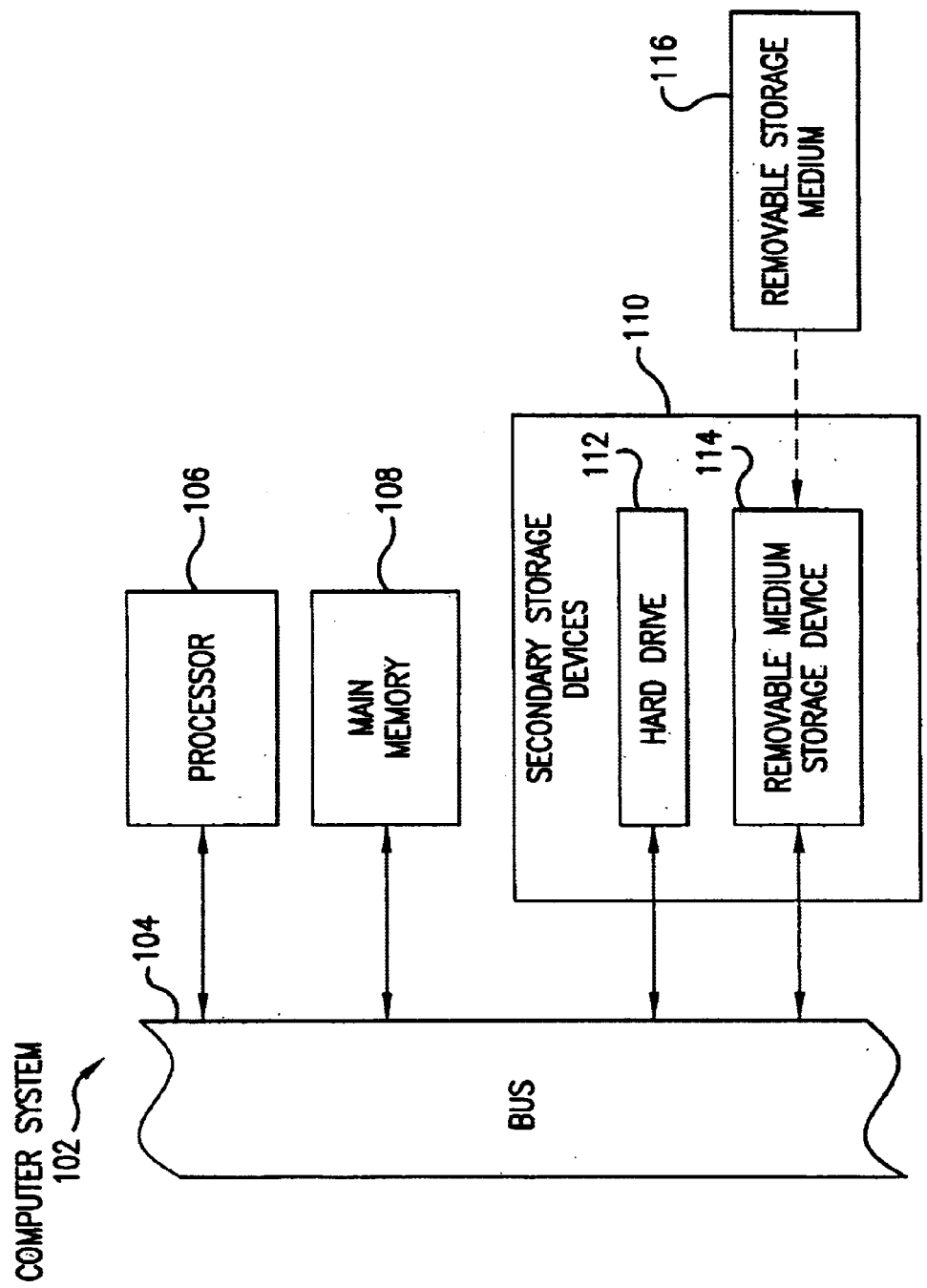
FIG. 2. Block diagram of a computer system 102 that can be used to implement the computer-based systems of present invention.

The present invention is based on whole-genome random sequencing of an autotrophic archaeon, Methanococcus jannaschii. The M. jannaschii genome consists of three physically distinct elements: (i) a large circular chromosome of 1,664,976 base pairs (bp) (shown on pages 153–586 and in SEQ ID NO:1), which contains 1682 predicted protein-coding regions and has a G+C content of 31.4%; (ii) a large circular extrachromosomal element (the large ECE) of 58,407 bp (shown on pages 586–601 and in SEQ ID NO:2), which contains 44 predicted protein-coding regions and has a G+C content of 28.2%; and (iii) a small circular extrachromosomal element (the small ECE) of 16,550 bp (shown on pages 602–606 and in SEQ ID NO:3), which contains 12 predicted protein-coding regions and has a G+C content of 28.8%.

The primary nucleotide sequences generated, the M. jannaschii chromosome, the large ECE, and the small ECE, are provided in SEQ ID NOs:1, 2, and 3, respectively. As used herein, the "primary sequence" refers to the nucleotide sequence represented by the IUPAC nomenclature system. The present invention provides the nucleotide sequences of SEQ ID NOs:1, 2, and 3, or a representative fragment thereof, in a form which can be readily used, analyzed, and interpreted by a skilled artisan.

As used herein; a "representative fragment" refers to M. jannaschii protein-encoding regions (also referred to herein as open reading frames), expression modulating fragments, uptake modulating fragments, and fragments that can be used to diagnose the presence of M. jannaschii in a sample. A non-limiting identification of such representative fragments is provided in Tables 2(a) and 3. As described in detail below, representative fragments of the present invention further include nucleic acid molecules having a nucleotide sequence at least 90% identical, preferably at least 95, 96%, 97%, 98%, or 99% identical, to an ORF identified in Table 2(a) or 3.

As indicated above, the nucleotide sequence information provided in SEQ ID NOs:1, 2 and 3 was obtained by sequencing the M. jannaschii genome using a megabase shotgun sequencing method. The sequences provided in SEQ ID NOs:1, 2 and 3 are highly accurate, although not necessarily a 100% perfect, representation of the nucleotide sequence of the M. jannaschii genome. As discussed in detail below, using the information provided in SEQ ID NOs:1, 2 and 3 and in Tables 2(a) and 3 together with routine cloning and sequencing methods, one of ordinary skill in the art would be able to clone and sequence all "representative fragments" of interest including open reading frames (ORFs) encoding a large variety of M. jannaschii proteins. In rare instances, this may reveal a nucleotide sequence error present in the nucleotide sequences disclosed in SEQ ID NOs:1, 2, and 3. Thus, once the present invention is made available (i.e., once the information in SEQ ID NOs:1, 2, and 3 and in Tables 2(a) and 3 have been made available), resolving a rare sequencing error would be well within the skill of the art. Nucleotide sequence editing software is publicly available. For example, Applied Biosystem's (AB) AutoAssembler™ can be used as an aid during visual inspection of nucleotide sequences.

Even if all of the rare sequencing errors were corrected, it is predicted that the resulting nucleotide sequences would still be at least about 99.9% identical to the reference nucleotide sequences in SEQ ID NOs:1, 2, and 3. Thus, the present invention further provides nucleotide sequences that are at least 99.9% identical to the nucleotide sequence of SEQ ID NO:1, 2, or 3 in a form which can be readily used; analyzed and interpreted by the skilled artisan. Methods for determining whether a nucleotide sequence is at least 99.9% identical to a reference nucleotide sequence of the present invention are described below.

Nucleic Acid Molecules

The present invention is directed to isolated nucleic acid fragments of the M. jannaschii genome. Such fragments include, but are not limited to, nucleic acid molecules encoding polypeptides (hereinafter open reading frames (ORFs)), nucleic acid molecules that modulate the expression of an operably linked ORF (hereinafter expression modulating fragments (EMFs)), nucleic acid molecules that mediate the uptake of a linked DNA fragment into a cell (hereinafter uptake modulating fragments (UMFs)), and nucleic acid molecules that can be used to diagnose the presence of M. jannaschii in a sample (hereinafter diagnostic fragments (DFs)).

By "isolated nucleic acid molecule(s)" is intended a nucleic acid molecule, DNA or RNA, that has been removed from its native environment. For example, recombinant DNA molecules contained in a vector are considered isolated for the purposes of the present invention. Further examples of isolated DNA molecules include recombinant DNA molecules maintained in heterologous host cells, purified (partially or substantially) DNA molecules in solution, and nucleic acid molecules produced synthetically. Isolated RNA molecules include in vitro RNA transcripts of the DNA molecules of the present invention.

In one embodiment, M. jannaschii DNA can be mechanically sheared to produce fragments about 15–20 kb in length, which can be used to generate a M. jannaschii DNA library by insertion into lambda clones as described in Example 1 below. Primers flanking an ORF described in Table 2(a) or 3 can then be generated using the nucleotide sequence information provided in SEQ ID NO:1, 2, or 3. The polymerase chain reaction (PCR) is then used to amplify and isolate the ORF from the lambda DNA library. PCR cloning is well known in the art. Thus, given SEQ ID NOs:1, 2, and 3, and Tables 2(a) and 3, it would be routine to isolate any ORF or other representative fragment of the *M. jannaschi* genome. Isolated nucleic acid molecules of the present invention include, but are not limited to, single stranded and double stranded DNA, and single stranded RNA, and complements thereof.

Tables 2(a), 2(b) and 3 describe ORFs in the *M. jannaschii* genome. In particular, Table 2(a) (pages 68–116 below) indicates the location of ORFs (i.e., the position) within the *M. jannaschii* genome that putatively encode the recited protein based on homology matching with protein sequences from the organism appearing in parentheticals (see the fourth column of Table 2(a)). The first column of Table 2(a) provides a name for each ORF. The second and third columns in Table 2(a) indicate an ORF's position in the nucleotide sequence provided in SEQ ID NO:1, 2 or 3. One of ordinary skill in the art will appreciate that the ORFs may be oriented in opposite directions in the *M. jannaschii* genome. This is reflected in columns 2 and 3. The fifth column of Table 2(a) indicates the percent identity of the protein sequence encoded by an ORF to the corresponding protein sequence from the organism appearing in parentheticals in the fourth column. The sixth column of Table 2(a) indicates the percent similarity of the protein sequence encoded by an ORF to the corresponding protein sequence from the organism appearing in parentheticals in the fourth column. The concepts of percent identity and percent similarity of two polypeptide sequences are well understood in the art and are described in more detail below. The eighth column in Table 2(a) indicates the length of the ORF in nucleotides. Each identified gene has been assigned a putative cellular role category adapted from Riley (Riley, M., *Microbiol. Rev.* 57:862 (1993)).

Table 2(b) (page 117 below) provides the single ORF identified by the present inventors that matches a previously published *M. jannaschii* gene. In particular, ORF MJ0479, which is 585 nucleotides in length and is positioned at nucleotides 1,050,508 to 1,049,948 in SEQ ID NO:1, shares 100% identity to the previously published *M. jannaschii* adenylate kinase gene.

Table 3 (pages 118–151 below) provides ORFs of the *M. jannaschii* genome that did not elicit a homology match with a known sequence from either *M. jannaschii* or another organism. As above, the first column in Table 3 provides the ORF name and the second and third columns indicate an ORF's position in SEQ ID NO:1, 2, or 3.

Table 4 (page 152 below) provides genes of *M. jannaschii* that contain inteins.

In the above-described Tables, there are three groups of ORF names. The one thousand six hundred and eighty two ORFs named "MJ-" (MJ0001-MJ1682) were identified on the *M. jannaschii* chromosome (SEQ ID NO:1). The forty four ORFs named "MJECL-" (MJECL01-MJECL44) were identified on the large ECE (SEQ ID NO:2). The twelve ORFs named "MJECS-" (MJECS01-MJES12) were identified on the small ECE (SEQ ID NO:3).

Further details concerning the algorithms and criteria used for homology searches are provided in the Examples below. A skilled artisan can readily identify ORFs in the *Methanococcus jannaschii* genome other than those listed in Tables 2(a), 2(b) and 3, such as ORFs that are overlapping or encoded by the opposite strand of an identified ORF in addition to those ascertainable using the computer-based systems of the present invention.

Isolated nucleic acid molecules of the present invention include DNA molecules having a nucleotide sequence substantially different than the nucleotide sequence of an ORF described in Table 2(a) or 3, but which, due to the degeneracy of the genetic code, still encode a *M. jannaschii* protein. The genetic code is well known in the art. Thus, it would be routine to generate such degenerate variants.

The present invention further relates to variants of the nucleic acid molecules of the present invention, which encode portions, analogs or derivatives of a *M. Jannaschii* protein encoded by an ORF described in Table 2(a) or 3. Non-naturally occurring variants may be produced using art-known mutagenesis techniques and include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the *M. jannaschii* protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical, to (a) the nucleotide sequence of an ORF described in Table 2(a) or 3, (b) the nucleotide sequence of an ORF described in Table 2(a) or 3, but lacking the codon for the N-terminal methionine residue, if present, or (c) a nucleotide sequence complementary to any of the nucleotide sequences in (a) or (b). By a polynucleotide having a nucleotide sequence at least, for example, 95% identical to the reference *M. jannaschii* ORF nucleotide sequence is intended that the nucleotide sequence of the polynucleotide is identical to the reference sequence except that the polynucleotide sequence may include up to five point mutations per each 100 nucleotides of the ORF sequence. In other words, to obtain a polynucleotide having a nucleotide sequence at least 95% identical to a reference ORF nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to the nucleotide sequence of a *M. jannaschii* ORF can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Preferred are nucleic acid molecules having sequences at least 90%, 95%, 96%, 97%, 98% or 99% identical to the nucleic acid sequence of a *M. jannaschii* ORF that encode a functional polypeptide. By a "functional polypeptide" is intended a polypeptide exhibiting activity similar, but not necessarily identical, to an activity of the protein encoded by the *M. jannaschii* ORF. For example, the *M. jannaschii* ORF MJ1434 encodes an endonuclease that degrades DNA. Thus, a "functional polypeptide" encoded by a nucleic acid molecule having a nucleotide sequence, for example, 95% identical to the nucleotide sequence of MJ1434, will also degrade DNA. As the skilled artisan will appreciate, assays for determining whether a particular polypeptide is "functional" will depend on which ORF is used as the reference sequence. Depending on the reference ORF, the assay chosen for measuring polypeptide activity will be readily apparent in light of the role categories provided in Table 2(a).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of a reference ORF will encode a functional polypeptide. In fact, since degenerate variants all encode the same amino acid sequence, this will be clear to the skilled artisan even without performing a comparison assay for protein activity. It will be further recognized in the art that, for such nucleic acid molecules that are not degenerate variants, a reasonable number will also encode a functional polypeptide. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

The present invention is further directed to fragments of the isolated nucleic acid molecules described herein. By a fragment of an isolated nucleic acid molecule having the nucleotide sequence of a *M. jannaschii* ORF is intended fragments at least about 15 nt, and more preferably at least about 20 nt, still more preferably at least about 30 nt, and even more preferably, at least about 40 nt in length that are useful as diagnostic probes and primers as discussed herein. Of course, larger fragments 50–500 nt in length are also useful according to the present invention as are fragments corresponding to most, if not all, of the nucleotide sequence of a *M. jannaschii* ORF. By a fragment at least 20 nt in length, for example, is intended fragments that include 20 or more contiguous bases from the nucleotide sequence of a *M. jannaschii* ORF. Since *M. jannaschii* ORFs are listed in Tables 2(a) and 3 and the genome sequence has been provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of a *M. jannaschii* protein. Methods for determining such epitope-bearing portions are described in detail below.

In another aspect, the invention provides an isolated nucleic acid molecule comprising a polynucleotide that hybridizes under stringent hybridization conditions to a portion of the polynucleotide in a nucleic acid molecule of the invention described above, for instance, an ORF described in Table 2(a) or 3. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide that hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., a *M. jannaschii* ORF), for instance, a portion 50–500 nt in length, or even to the entire length of the reference polynucleotide, are also useful as probes according to the present invention, as are polynucleotides corresponding to most, if not all, of a *M. jannaschii* ORF.

By "expression modulating fragment" (EMF), is intended a series of nucleotides that modulate the expression of an operably linked ORF or EMF. A sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments that induce the expression of an operably linked ORF in response to a specific regulatory factor or physiological event. EMF sequences can be identified within the *M. jannaschii* genome by their proximity to the ORFs described in Tables 2(a), 2(b), and 3. An intergenic segment, or a fragment of the intergenic segment, from about 10 to 200 nucleotides in length, taken 5' from any one of the ORFs of Tables 2(a), 2(b) or 3 will modulate the expression of an operably linked 3' ORF in a fashion similar to that found with the naturally linked ORF sequence. As used herein, an "intergenic segment" refers to the fragments of the *M. jannaschii* genome that are between two ORF(s) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF will modulate the expression of an operably linked marker sequence. A more detailed discussion of various marker sequences is provided below.

A sequence that is suspected as being an EMF is cloned in all three reading frames in one or more restriction sites upstream from the marker sequence in the EMF trap vector. The vector is then transformed into an appropriate host using known procedures and the phenotype of the transformed host in examined under appropriate conditions. As described above, an EMF will modulate the expression of an operably linked marker sequence.

By "uptake modulating fragment" (UMF), is intended a series of nucleotides that mediate the uptake of a linked DNA fragment into a cell. UMFs can be readily identified using known UMFs as a target sequence or target motif with the computer-based systems described below. The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

By a "diagnostic fragment" (DF), is intended a series of nucleotides that selectively hybridize to *M. jannaschii* sequences. DFs can be readily identified by identifying unique sequences within the *M. jannaschii* genome, or by generating and testing probes or amplification primers consisting of the DF sequence in an appropriate diagnostic format for amplification or hybridization selectivity.

Each of the ORFs of the *M. jannaschii* genome disclosed in Tables 2(a) and 3, and the EMF found 5' to the ORF, can be used in numerous ways as polynucleotide reagents. The sequences can be used as diagnostic probes or diagnostic amplification primers to detect the presence *M. jannaschii* in a sample. This is especially the case with the fragments or ORFs of Table 3, which will be highly selective for *M. jannaschii*.

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla. (1988)).

Triple helix- formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

Vectors and Host Cells

The present invention further provides recombinant constructs comprising one or more fragments of the *M. jannaschii* genome. The recombinant constructs of the present invention comprise a vector, such as a plasmid or viral vector, into which, for example, a *M. jannaschii* ORF is inserted. The vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention further provides host cells containing any one of the isolated fragments (preferably an ORF) of the *M. jannaschii* genome described herein. The host cell can be a higher eukaryotic host cell, such as a mammalian cell, a lower eukaryotic host cell, such as a yeast cell, or the can be a procaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)). Host cells containing, for example, a *M. jannaschii* ORF can be used conventionally to produce the encoded protein.

Polypeptides and Fragments

The invention further provides an isolated polypeptide encoded by a *M. jannaschii* ORF described in Tables 2(a) or 3, or a peptide or polypeptide comprising a portion of the isolated polypeptide. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues.

It will be recognized in the art that some amino acid sequence of the *M. jannaschii* polypeptide can be varied without significant affect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of a *M. jannaschii* protein encoded by an ORF described in Table 2(a) or 3 that show substantial protein activity. Methods for assaying such "functional polypeptides" for protein activity are described above. Variations include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on protein activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning amino acid changes that are likely to be phenotypically silent (i.e., are not likely to have a significant deleterious effect on function) can be found in Bowie, J. U., et al., "Deciphering the Message in Protein Sequences: Tolerance to Amino Acid Substitutions," *Science* 247:1306–1310 (1990).

The fragment, derivative, variant or analog of a *M. jannaschii* polypeptide encoded by an ORF described in Table 2(a) or 3, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as an IgG Fc fusion region peptide or leader or secretory sequence or a sequence which is employed for purification of the polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of a *M. jannaschii* ORF-encoded protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in a *M. jannaschii* ORF-encoded protein of the present invention that are essential for function can be identified by methods known in the art, such a s site-directed mutagenesis or alanine-scanning mutagenesis (Cunningham and Wells, *Science* 244:1081–1085 (1989)). The latter procedure introduces single alanine mutaions at every residue in the molecule.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that hive been purified, partially or substantially, from a recombinant host cell. For example, a recombinant produced version of a *M. jannaschii* ORF-encoded protein can be substantially purified by the one-step method described in Smith and Johnson, *Gene* 67.231–40 (1988).

The polypeptides of the present invention include the proteins encoded by (a) an ORF described in Table 2(a) or 3 or (b) an ORF described in Table 2(a) or 3, but minus the codon for the N-terminal methionine residue, if present, as well as polypeptides that have at least 90% similarity, more preferably at least 95% similarity, and still more preferably at least 96%, 97%, 98% or 99% similarity to a *M. jannaschii* ORF-encoded protein. Further polypeptides of the present invention include polypeptides at least 90% identical, more preferably at least 95% identical, still more preferably at least 96%, 97%, 98% or 99% identical to a *M. jannaschii* ORF-encoded protein.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482–489, 1981) to find the best segment of similarity between two sequences.

By a polypeptide having an amino acid sequence at least, for example, 95% "identical" to a reference amino acid sequence of a *M. jannaschii* ORF-encoded protein is intended that the amino acid sequence of the polypeptide is identical to the reference sequence except that the polypeptide sequence may include up to five amino acid alterations per each 100 amino acids of the reference sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide has an amino acid sequence at least 90%, 95%, 96%, 97%, 98% or 99% identical to the amino acid sequence of a *M. jannaschii* ORF-encoded protein can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As described in detail below, the polypeptides of the present invention can also be used to raise polyclonal and monoclonal antibodies, which are useful in assays for detecting *M. jannaschii* protein expression.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983). Antibodies that react with predetermined sites on proteins are described in *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HAI polypeptide chain, induced antibodies that reacted with the HAI protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al, supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomer which is a topographical equivalent of a ligand which is complementary to the ligand binding site of a particular receptor of interest. Similarly, U.S. Pat. No.

5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, the polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been demonstrated, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric protein or protein fragment alone (Fountoulakis et al., *J Biochem* 270:3958–3964 (1995)).

Protein Function

Each ORF described in Table 2(a) was assigned to biological role categories adapted from Riley, M., *Microbiology Reviews* 57(4):862 (1993)). This allows the skilled artisan to determine a function for each identified coding sequence. For example, a partial list of the *M. jannaschii* protein functions provided in Table 2(a) includes: methanogenesis, amino acid biosynthesis, cell division, detoxification, protein secretion, transformation, central intermediary metabolism, energy metabolism, degradation of DNA, DNA replication, restriction, modification, recombination and repair, transcription, RNA processing, translation, degradation of proteins, peptides and glycopeptides, ribosomal proteins, translation factors, transport, tRNA modification, and drug and analog sensitivity. A more detailed description of several of these functions is provided in Example 1 below.

Diagnostic Assays

The present invention further provides methods to identify the expression of an ORF of the present invention, or homolog thereof, in a test sample, using one of the DFs or antibodies of the present invention. Such methods involve incubating a test sample with one or more of the antibodies or one or more of the DFs of the present invention and assaying for binding of the DFs or antibodies to components within the test sample.

Conditions for incubating a DF or antibody with a test sample vary. Incubation conditions depend on the format employed in the assay, the detection methods employed, and the type and nature of the DF or antibody used in the assay. One skilled in the art will recognize that any one of the commonly available hybridization, amplification or immunological assay formats can readily be adapted to employ the DFs or antibodies of the present invention. Examples of such assays can be found in Chard, T., *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartmentalized kit to receive, in close confinement, one or more containers including comprising: (a) a first container comprising one of the DFs or antibodies of the present invention; and (b) one or more other containers comprising one or more of the following: wash reagents, reagents capable of detecting presence of a bound DF or antibody.

A compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or DF.

Types of detection reagents include labeled nucleic acid probes, labeled secondary antibodies, or in the alternative, if the primary antibody is labeled, the enzymatic, or antibody binding reagents that are capable of reacting with the labeled antibody. One skilled in the art will readily recognize that the disclosed DFs and antibodies of the present invention can be readily incorporated into one of the established kit formats that are well known in the art.

Screening Assay for Binding Agents

Using the isolated proteins described herein, the present invention further provides methods of obtaining and identifying agents that bind to a protein encoded by a *M. jannaschii* ORF or to a fragment thereof.

The method involves:

(a) contacting an agent with an isolated protein encoded by a M. jannaschii ORF, or an isolated fragment thereof; and (b) determining whether the agent binds to said protein or said fragment.

The agents screened in the above assay can be, but are not limited to, peptides, carbohydrates, vitamin derivatives, or other pharmaceutical agents. The agents can be selected and screened at random or rationally selected or designed using protein modeling techniques. For random screening, agents such as peptides, carbohydrates, pharmaceutical agents and the like are selected at random and are assayed for their ability to bind to the protein encoded by an ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides, In *Synthetic Peptides, A User's Guide*, W. H. Freeman, NY (1992), pp. 289–307, and Kaspczak et al., *Biochemistry* 28:9230–8 (1989), or pharmaceutical agents, or the like.

In addition to the foregoing, one class of agents of the present invention, can be used to control gene expression through binding to one of the ORFs or EMFs of the present invention. As described above, such agents can be randomly screened or rationally designed and selected. Targeting the ORF or EMF allows a skilled artisan to design sequence specific or element specific agents, modulating the expression of either a single ORF or multiple ORFs that rely on the same EMF for expression control.

One class of DNA binding agents are those that contain nucleotide base residues that hybridize or form a triple helix by binding to DNA or RNA. Such agents can be based on the classic phosphodiester, ribonucleic acid backbone, or can be a variety of sulfhydryl or polymeric derivatives having base attachment capacity.

Agents suitable for use in these methods usually contain 20 to 40 bases and are designed to be complementary to a region of the gene involved in transcription (triple helix—see Lee et al., *Nucl. Acids Res.* 6:3073 (1979); Cooney et al, *Science* 241:456 (1988); and Dervan et al., *Science* 251: 1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Computer Related Embodiments

The nucleotide sequence provided in SEQ ID NO:1, 2, or 3, a representative fragment thereof, or a nucleotide sequence at least 99.9% identical to the sequence provided in SEQ ID NO:1, 2, or 3, can be "provided" in a variety of mediums to facilitate use thereof. As used herein, provided refers to a manufacture, other than an isolated nucleic acid molecule, that contains a nucleotide sequence of the present invention, i.e., the nucleotide sequence provided in SEQ ID NO:1, 2, or 3, a representative fragment thereof, or a nucleotide sequence at least 99.9% identical to SEQ ID NO:1, 2, or 3. Such a manufacture provides the M. jannaschii genome or a subset thereof (e.g., a M. jannaschii open reading frame (ORF)) in a form that allows a skilled artisan to examine the manufacture using means not directly applicable to examining the M. jannaschii genome or a subset thereof as it exists in nature or in purified form.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently know methods for recording information on computer readable medium to generate manufactures comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NO:1, 2, or 3, a representative fragment thereof, or a nucleotide sequence at least 99.9% identical to SEQ ID NO:1, 2, or 3, in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403410 (1990)) and BLAZE (Brutiag et al., *Comp. Chem.* 17:203–207 (1993)) search algorithms on a Sybase system can be used to identify open reading frames (ORFs) within the *M. jannaschii* genome that contain homology to ORFs or proteins from other organisms. Such ORFs are protein-encoding fragments within the *M. jannaschii* genome and are useful in producing commercially important proteins such as enzymes used in methanogenesis, amino acid biosynthesis, metabolism, fermentation, transcription, translation, RNA processing, nucleic acid and protein degradation, protein modification, and DNA replication, restriction, modification, recombination, and repair. A comprehensive list of ORFs encoding commercially important *M. jannaschii* proteins is provided in Tables 2(a) and 3.

The present invention further provides systems, particularly computer-based systems, which contain the sequence information described herein. Such systems are designed to identify commercially important fragments of the *M. jannaschii* genome. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the *M. jannaschii* genome that match a particular target sequence or target motif. A variety of known algorithms are disclosed publicly and a variety of commercially available software for conducting search means are available and can be used in the computer-based systems of the present invention. Examples of such software include, but are not limited to, MacPattern (EMBL), BLASTN and BLASTX (NCBIA). A skilled artisan can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that during searches for commercially important fragments of the *M. jannaschii* genome, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzymic active sites and signal sequences. Nucleic acid target motifs include, but are not limited to, promoter sequences, hairpin structures and inducible expression elements (protein binding sequences).

Thus, the present invention further provides an input means for receiving a target sequence, a data storage means for storing the target sequence and the homologous *M. jannaschii* sequence identified using a search means as described above, and an output means for outputting the identified homologous *M. jannaschii* sequence. A variety of structural formats for the input and output means can be used to input and output information in the computer-based systems of the present invention. A preferred format for an output means ranks fragments of the *M. jannaschii* genome possessing varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments of the *M. jannaschii* genome. For example, implementing software which implement the BLAST and BLAZE algorithms (Altschul et al., *J. Mol. Biol.* 215:403–410 (1990)) can be used to identify open reading frames within the *M. jannaschii* genome. A skilled artisan can readily recognize that any one of the publicly available homology search programs can be used as the search means for the computer-based systems of the present invention.

One application of this embodiment is provided in FIG. 8. FIG. 8 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable medium storage device 114 once inserted in the removable medium storage device 114.

A nucleotide sequence of the present invention may be stored in a well known manner in the main memory 108, any of the secondary storage devices 110, and/or a removable storage medium 116. Software for accessing and processing the genomic sequence (such as search tools, comparing tools, etc.) reside in main memory 108 during execution.

Having generally described the invention, the same will be more readily understood by reference to the following examples, which are provided by way of illustration and are not intended as limiting.

EXPERIMENTAL

COMPLETE GENOME SEQUENCE OF THE METHANOGENIC ARCHAEON, *METHANOCOCCUS JANNASCHII*

EXAMPLE 1

A whole genome random sequencing method (Fleischmann, R. D., et al., *Science* 269:496 (1995); Fraser, C. M., et al., *Science* 270:397 (1995)) was used to obtain the complete genome sequence for *M. jannaschii*. A small insert plasmid library (2.5 Kbp average insert size) and a large insert lambda library (16 Kbp average insert size) were used as substrates for sequencing. The lambda library was used to form a genome scaffold and to verify the orientation and integrity of the contigs formed from the assembly of sequences from the plasmid library. All clones were sequenced from both ends to aid in ordering of contigs during the sequence assembly process. The average length of sequencing reads was 481 bp. A total of 36,718 sequences were assembled by means of the TIGR Assembler (Fleischmann, R. D., et al., Science 269:496 (1995); Fraser, C. M., et al., *Science* 270:397 (1995); Sutton G., et al, *Genome Sci. Tech.* 1:9 (1995)). Sequence and physical gaps were closed using a combination of strategies (Fleischmann, R. D., et al., *Science* 269:496 (1995); Fraser, C. M., et al., *Science* 270:397 (1995)). The colinearity of the in vivo genome to the genome sequence was confirmed by comparing restriction fragments from six, rare cutter, restriction enzymes (Aat II, BamHI, Bgl II, Kpn I, Sma I, and Sst II) to those predicted from the sequence data Additional confidence in the colinearity was provided by the genome scaffold produced by sequence pairs from 339 large-insert lambda clones, which covered 88% of the main chromosome. Open reading frames (ORFs) and predicted protein-coding regions were identified as described (Fleischmann, R. D., et al., *Science* 269:496 (1995); Fraser, C. M., et al., *Science* 270:397 (1995)) with some modification. In particular, the statistical prediction of *M. jannaschii* genes was performed with GeneMark (Borodovsky, M. & McIninch, *J. Comput. Chem.* 17:123 (1993)). Regular GeneMark uses nonhomogeneous Markov models derived from a training set of coding sequences and ordinary Markov models derived from a training set of noncoding sequences. Only a single 16S ribosomal RNA sequence of *M. jannaschii* was available in the public sequence databases before the whole genome sequence described here. Thus, the initial training set to determine parameters of a coding sequence Markov model was chosen as a set of ORFs>1000 nucleotides (nt). As an initial model for non-coding sequences, a zero-order Markov model with genome-specific nucleotide frequencies was used. The initial models were used at the first prediction step. The results of the first prediction were then used to compile a set of putative genes used at the second training step. Alternate rounds of training and predicting were continued until the set of predicted genes stabilized and the parameters of the final fourth-order model of coding sequences were derived. The regions predicted as noncoding were then used as a training set for a final model for noncoding regions. Cross-validaton simulations demonstrated that the GeneMark program trained as described above was able to correctly identify coding regions of at least 96 nt in 94% of the cases and noncoding regions of the same length in 96% of the cases. These values assume that the self-training method produced correct sequence annotation for compiled control sets. Comparison with the results obtained by searches against a nonredundant protein database (Fleischmann, R. D., et al., *Science* 269:496 (1995); Fraser, C. M., et al., *Science* 270:397 (1995)) demonstrated that almost all genes identified by sequence similarity were predicted by the GeneMark program as well. This observation provides additional confidence in genes predicted by GeneMark whose protein translations did not show significant similarity to known protein sequences. The predicted protein-coding regions were search against the Blocks database (Henikoff, S. & Henikoff, J. G., *Genomics* 19:97 (1994)] by means of BLIMPS (Wallace, J. C. & Henikoff, S., *CABIOS* 8:249 (1992)) to verify putative identifications and to identify potential functional motifs in predicted protein-coding regions that had no database match. Genes were assigned to known metabolic pathways. When a gene appeared to be missing from a pathway, the unassigned ORFs and the complete *M. jannaschii* genome sequence were searched with specific query sequences or motifs from the Blocks database. Hydrophobicity plots were performed on all predicted protein-coding regions by means of the Kyte-Doolittle algorithm (Kyte, J. & Doolittle, R. F., *J. Mol. Biol.* 157:105 (1982)) to identify potentially functionally relevant signatures in these sequences.

The *M. jannaschii* genome comprises three physically distinct elements: i) a large circular chromosome of 1,664, 976 base pairs (bp) (SEQ ID NO:1), which contains 1682 predicted protein-coding regions and has a G+C content of 31.4%; ii) a large circular extrachromosomal element (ECE) (Zhao, H., et al., *Arch. Microbiol.* 150:178 (1988)) of 58,407 bp (SEQ ID NO:2), which contains 44 predicted protein coding regions and has a G+C content of 28.2% (FIG. 3); and iii) a small circular ECE (Zhao, H., et al., *Arch. Microbiol.* 150:178 (1988)) of 16,550 bp (SEQ ID NO:3), which contains 12 predicted protein coding regions, and has a G+C content of 28.8% (FIG. 3). With respect to its shape, size, G+C content, and gene density the main chromosome resembles that of *H. influenzae*. However, here the resemblance stops.

Of the 1743 predicted protein-coding regions reported previously for *H. influenzae*, 78% had a match in the public sequence database (Fleischmann, R. D., et al., *Science* 269:496 (1995); Fraser, C. M., et al, *Science* 270:397 (1995)). Of these, 58% were matches to genes with reasonably well defined function, while 20% were matches to genes whose function was undefined. Similar observations were made for the *M. genitalium* genome (Fleischmann, R. D., et al., *Science* 269:496 (1995); Fraser, C. M., et al., *Science* 270:397 (1995)). Eighty-three percent of the predicted protein coding regions from *M. genitalium* have a counterpart in the *H. influenzae* genome. In contrast, only 38% of the predicted protein-coding regions from *M. jannaschii* match a gene in the database that could be assigned a putative cellular role with high confidence; 6% of the predicted protein-coding regions had matches to hypothetical proteins (FIG. 4; Tables 2–3). Approximately 100 genes in *M. jannaschii* had marginal similarity to genes or segments of genes from the public sequence databases and could not be assigned a putative cellular role with high confidence. Only 11% of the predicted protein-coding regions from *H. influenzae* and 17% of the predicted protein coding regions from *M. genitalium* matched a predicted protein coding region from *M. jannaschii*. Clearly the *M. jannaschii* genome, and undoubtedly, therefore, all archaeal genomes are remarkably unique, as the phylogenetic position of these organisms would suggest.

Energy production in *M. jannaschii* occurs via the reduction of $CO_2$ with $H_2$ to produce methane. Genes for all of the known enzymes and enzyme complexes associated with methanogenesis (DiMarco, A. A., et al., *Ann. Rev. Biochem.* 59:355 (1990)) were identified in *M. jannaschii*, the sequence and order of which are typical of methanogens. *M. jannaschii* appears to use both $H_2$ and formate as substrates for methanogenesis, but lacks the genes to use methanol or acetate. The ability to fix nitrogen has been demonstrated in a number of methanogens (Belay, N., et al., *Nature* 312:286 (1984)) and all of the genes necessary for this pathway have been identified in *M. jannaschii* (Tables 2–3). In addition to its anabolic pathways, several scavenging molecules have been identified in *M. jannaschii* that probably play a role in importing small organic compounds, such as amino acids, from the environment (Tables 2–3).

Three different pathways are known for the fixation of $CO_2$ into organic carbon: the non-cyclic, reductive acetyl-coenzyme A-carbon monoxide dehydrogenase pathway (Ljungdahl-Wood pathway), the reductive trichloroacetic acid (TCA) cycle, and the Calvin cycle. Methanogens fix carbon by the Ljungdahl-Wood pathway (Wood, H. G., et al., *TIBS* 11:14 (1986)), which is facilitated by the carbon monoxide dehydrogenease enzyme complex (CODH) (Blaat, M., *Antonie van Leewenhoek* 66:187 (1994)). The complete Ljungdahl-Wood pathway, encoded in the *M. jannaschii* genome, depends on the methyl carbon in methanogenesis; however, methanogenesis can occur independently of carbon fixation.

Although genes encoding two enzymes required for gluconeogenesis (glucopyruvate oxidoreductase and phosphoenolpyruvate synthase) were found in the *M. jannaschii* genome, genes encoding other key intermediates of gluconeogenesis (fructose bisphosphatase and fructose 1,6-bisphosphate aldolase) were not been identified. Glucose catabolism by glycolysis also requires the aldolase, as well as phosphofructokinase, an enzyme that also was not found in *M. jannaschii* and has not been detected in any of the Archaea. In addition, genes specific for the Entner-Doudoroff pathway, an alternative pathway used by some microbes for the catabolism of glucose, were not identified in the genomic sequence. The presence of a number of nearly complete metabolic pathways suggests that some key genes are not recognizable at the sequence level, although we cannot exclude the possibility that *M. jannaschii* may use alternative metabolic pathways.

In general, *M. jannaschii* genes that encode proteins involved in the transport of small inorganic ions into the cell are homologs of bacterial genes. The genome includes many representatives of the ABC transporter family, as well as genes for exporting heavy metals (e.g., the chromate-resistance protein) and other toxic compounds (e.g the nor A drug efflux pump locus).

More than 20 predicted protein-coding regions have sequence similarity to polysaccharide biosynthetic enzymes. These genes have only bacterial homologs or are most closely related to their bacterial counterparts. The identified polysaccharide biosynthetic genes in *M. jannaschii* include those for the interconversion of sugars, activation of sugars to nucleotide sugars, and glycosyltransferases for the polymerization of nucleotide sugars into oligo- and polysaccharides that are subsequently incorporated into surface structures (Hartmann, E. and König, H., *Arch Microbiol.* 151:274 (1989)). In an arrangement reminiscent of bacterial polysaccharide biosynthesis genes, many of the genes for *M. jannaschii* polysaccharide production are clustered together (Tables 2–3, FIG. 4). The G+C content in this region is <95% of that in the rest of the *M. jannaschii* genome. A similar observation was made in *Salmonella typhimurium* (Jiang, X. M., et al., *Mol. Microbiol.* 5:695 (1991)) in which the gene cluster for lipopolysaccharide 0 antigen has a significantly lower G+C ratio than the rest of the genome. In that case, the difference in G+C content was interpreted as meaning that the region originated by lateral transfer from another organism.

Of the three main multicomponent information processing systems (transcription, translation, and replication), translation appears the most universal in its overall makeup in that the basic translation machinery is similar in all three domains of life. *M. jannaschii* has two ribosomal RNA operons, designated A and B, and a separate 5S RNA gene that is associated with several transfer RNAs (tRNAs). Operon A has the organization, 16S—23S—5S, whereas operon B lacks the 5S component An alanine tRNA is situated in the spacer region between the 16S and 23S subunits in both operons. The majority of proteins associated with the ribosomal subunits (especially the small subunit) are present in both Bacteria and Eukaryotes. However, the relatively protein-rich eukaryotic ribosome contains additional ribosomal proteins not found in the bacterial ribosome. A smaller number of bacteria-specific ribosomal proteins exist as well. The *M. jannaschii* genome contains all ribosomal proteins that are common to eukaryotes and bacteria. It shows no homologs of the bacterial-specific ribosomal proteins, but does possess homologs of a number of the eukaryotic-specific ones. Homologs of all archaea-specific ribosomal proteins that have been reported to date (Lechner, K., et al., *J. Mol. Evol.* 29:20 (1989); Köpke, A. K. E. and Wittimann-Liebold, B., *Can. J. Microbiol.* 35:11 (1989)) are found in *M. jannaschii*.

As previously shown for other archaea (Iwabe, N., et al., *Proc. Natl. Acad. Sci. USA* 86:9355 (1989); Gogarten J. P., et al., *Proc. Natl. Acad. Sci. USA* 86:6661 (1989); Brown, J. R. and Doolittle, W. F., *Proc. Natl. Acad. Sci. USA* 92:2441 (1995)), the Methanococcus translation elongation factors EF-1α (EF-Tu in bacteria) and EF-2 (EF-G in bacteria) are most similar to their eukaryotic counterparts. In addition, the *M. jannaschii* genome contains 11 translation initiation factor genes. Three of these genes encode the subunits homologous to those of the eukaryotic IF-2, and are reported here in the Archaea for the first time. A fourth initiation factor gene that encodes a second IF-2 is also found in *M. jannaschii*. This additional IF-2 gene is most closely related to the yeast protein FUN12 which, in turn, appears to be a homolog of the bacterial IF-2. It is not known which of the two IF-2-like initiation factors identified in *M. jannaschii* plays a role in directing the initiator tRNA to the start site of the mRNA. The fifth identified initiation factor gene in *M. jannaschii* encodes IF-1A, which has no bacterial homolog. The sixth gene encodes the hypusine-containing initiation factor eIF-5a. Two subunits of the translation initiation factor eIF-2B were identified in *M. jannaschii*. Finally, three putative adenososine 5'-triphosphate (ATP)-dependent helicases were identified that belong to the eIF-4a family of translation initiation factors.

Thirty-seven tRNA genes were identified in the *M. jannaschii* genome. Almost all amino acids encoded by two codons have a single TRNA, except for glutamic acid, which has two. Both an initiator and an internal methionyl tRNA are present. The two pyrimidine-ending isoleucine codons are covered by a single tRNA, while the third (AUA) seems covered by a related tRNA having a CAU anticodon. A single tRNA appears to cover the three isoleucine codons. Those amino acids encoded by f our codons each have two tRNAs, one to cover the Y-, the other the R-ending, codons. Valine has a third tRNA, which is specific for the GUG codon; and alanine has three tRNAs (two of which are in the spacer regions separating the 16S and 23S subunits in the two ribosomal RNA operons). Leucine, serine and arginine, all of which have six codons, each posses three corresponding tRNAs. The genes for the internal methionine and tryptophan tRNAs contain introns in the region of their anti-codon loops.

A tRNA also exists for selenocysteine UGA codon). At least four genes in *M. jannaschii* contain internal stop codons that are potential selenocysteine codons: the α chain of formate dehydrogenase, coenzyme F420 reducin hydrognase, β-chain tungsten formyl methanofuran dehydrogenase, and a heterodisulfide reductase. Three genes with a putative role in selenocysteine metabolism were identified by their similarity to the sel genes from other organisms (Tables 2–3).

Recognizable homologs for four of the aminoacyl-tRNA synthetases (glutamine, asparagine, lysine, and cysteine) were not identified in the *M. jannaschii* genome. The absence of a glutaminyl-tRNA synthetase is not surprising in that a number of organisms, including at least one archaeon, have none (Wilcox, M., *Eur. J Biochem.* 11:405 (1969); Martin, N. C., et al., *J. Mol. Biol.* 101:285 (1976); Martin, N. C., et al., *Biochemistry* 16:4672 (1977); Schon, A., et al., *Biochimie* 70:391 (1988); Soll, D. and RajBhandary, U., Eds. *Am. Soc. for Microbiol.* (1995)). In these instances, glutaminyl tRNA charging involves a post-charging conversion mechanism whereby the tRNA is charged by the glutamyl-tRNA synthetase with glutamic acid, which then is enzymatically converted to glutamrine. A post-charging conversion is also involved in selenocysteine charging via the seryl-tRNA synthetase. A similar mechanism has been proposed for asparagine charging, but has never been demonstrated (Wilcox, M.,*Eur. J. Biochem.* 11:405 (1969); Martin, N. C., et al., *J. Mol. Biol.* 101:285 (1976); Martin, N. C., et al., *Biochemistry* 16:4672 (1977); Schon, A., et al., *Biochimie* 70:391 (1988); Soll, D. and RajBhandary, U., Eds. *Am. Soc. for Microbiol.* (1995)). The inability to find homologs of the lysine and cysteine aminoacyl-tRNA synthetases is surprising because bacterial and eukaryotic versions in each instance show clear homology.

Aminoacyl-tRNA synthetases of *M. jannaschii* and other archaea resemble eukaryoticsynthetases more closely than they resemble bacterial forms. The tryptophanyl synthetase is one of the more notable examples, because the *M. jannaschii* and eukaryotic version do not appear to be specifically related to the bacterial version (de Pouplana, R., et al., *Proc. Natl. Acad. Sci., USA* 93:166 (1996)). Two versions of the glycyl synthetase are known in bacteria, one that is very unlike the version found in Archaea and Eukaryote and one that is an obvious homolog of it (Wagner, E. A., et al., *J. Bacteriol.* 177:5179 (1995); Logan, D. T., et al., *EMBO J.* 14:4156 (1995)).

Eleven genes encoding subunits of the DNA-dependent RNA polymerase were identified in the *M. jannaschii* genome. The sequence similarity between the subunits and their homologs in *Sutfolobus acidocaldarius* supports the evolutionary unity of the archaeal polymerase complex (Woese, C. R. and Wolfe, R. S., Eds. *The Bacteria, vol. VIII* (Academic Press, NY, 1985); Langer, D., et al., *Proc. Natl. Acad. Sci.* 92:5768 (1995); Lanzendoerfer, M. et al., *System. Appl. Microbiol.* 16:656 (1994)). All of the subunits found in *M. jannaschii* show greater similarity to their eukaryotic counterparts than to the bacterial homologs. The genes encoding the five largest subunits (A', A", B', B", D) have homologs in all organisms. Six genes encode subunits shared only by Archaea and Eukaryotes (E, H, K, L, and N). The *M. jannaschii* homolog of the *S. acidocaldarius* subunit E is split into two genes designated E' and E". *Sulfobus acidocaldarius* also contains two additional small subunits of RNA polymerase, designated G and F, that have no counterparts in either Bacteria or Eukaryotes. No homolog of these subunits was identified in *M. jannaschii*.

The archaeal transciption initiation system is essentially the same as that found in Eukaryotes, and is radically different from the bacterial version (Klenk, H. P. and Doolittle, W. F., *Curr. Biol.* 4.920 (1994)). The central molecules in the former systems are the TATA-binding protein (TBP) and transcription factor B (TFIIB and TFIIIB in Eukaryotes, or simply TFB). In the eukaryotic systems, TBP and TFB are parts of larger complexes, and additional factors (such as TFIIA and TFIIF) are used in the transcription process. However, the *M. jannaschii* genome does not contain obvious homologs of TFIIA and TFIIF.

Several components of the replication machinery were identified in *M. jannaschii*. The *M. jannaschii* genome appears to encode a single DNA-dependent polymerase that is a member of the B family of polymerases (Bernard, A., et al.,*EMBO J.* 6:4219 (1987); Cullman, G., et al.,*Molec. Cell Biol.* 15:4661 (1995); Uemori, T., et al., *J. Bacteriol.* 117:2164 (1995); Delarue, M., et al., *Prot. Engineer.* 3:461

(1990); Gavin, K. A., et al., *Science* 270:1667 (1995)). The polymerase shares sequence similarity and three motifs with other family B polymerases, including eukaryotic α, γ, and ε polymerases, bacterial polymerase II, and several archaeal polymerases. However, it is not homologous to bacterial polymerase I and has no homologs in *H. influenzae* or *M. genitalium*.

Primer recognition by the polymerase takes place through a structure-specific DNA binding complex, the replication factor complex (rfc) (Bernard, A., et al., *EMBO J.* 6:4219 (1987); Cullman, G., et al., *Molec. Cell Biol.* 15:4661 (1995); Uemori, T., et al., *J. Bacteriol.* 117:2164 (1995); Delarue, M., et al., *Prot. Engineer.* 3:461 (1990); Gavin, K. A., et al., *Science* 270:1667 (1995)). In humans and yeast, the rfc is composed of five proteins: a large subunit and four small subunits that have an associated adenosine triphosphatase (ATPase) activity stimulated by proliferating cell nuclear antigen (PCNA). Two genes in *M. jannaschii* are putative members of a eukaryotic-like replication factor complex. One of the genes in *M. jannaschii* is a putative homolog of the large subunit of the rfc, whereas the second is a putative homolog of one of the small subunits. Among Eukaryotes, the rfc proteins share sequence similarity in eight signature domains (Bernard, A., et al., *EMBO J.* 6:4219 (1987); Cullman, G., et al., *Molec. Cell Biol.* 15:4661 (1995); Uemori, T., et al., *J. Bacteriol.* 117:2164 (1995); Delarue, M., et al., *Prot. Engineer.* 3:461 (1990); Gavin, K. A., et al., *Science* 270:1667 (1995)). Domain I is conserved only in the large subunit among Eukaryotes and is similar in sequence to DNA ligases. This domain is missing in the large-subunit homolog in *M. jannaschii*. The remaining domains in the two *M. jannaschii* genes are well-conserved relative to the eukaryotic homologs. Two features of the sequence similarity in these domains are of particular interest. First, domain II (an ATPase domain) of the small-subunit homolog is split between two highly conserved amino acids (lysine and threonine) by an intervening sequence of unknown function. Second, the sequence of domain VI has regions that are useful for distinguishing between bacterial and eukaryotic rfc proteins (Bernard, A., et al., *EMBO J.* 6:4219 (1987); Cullman, G., et al., *Molec. Cell Biol.* 15:4661 (1995); Uemori, T., et al., *J. Bacteriol.* 117:2164 (1995); Delarue, M., et al., *Prot. Engineer.* 3:461 (1990); Gavin, K. A., et al., *Science* 270:1667 (1995)); the rfc sequence for *M. jannaschii* shares the characteristic eukaryotic signature in this domain.

We have attempted to identify an origin of replication by searching the *M. jannaschii* genome sequence with a variety of bacterial and eukaryotic replication-origin consensus sequences. Searches with oriC, ColE1, and autonomously replicating sequences from yeast (Bernard, A., et al., *EMBO J.* 6:4219 (1987); Cullman, G., et al., *Molec. Cell Biol.* 15:4661 (1995); Uemori, T., et al., *J. Bacteriol.* 117:2164 (1995); Delarue, M., et al., *Prot. Engineer.* 3:461 (1990); Gavin, K. A., et al., *Science* 270:1667 (1995)) did not identify an origin of replication. With respect to the related cellular processes of replication initiation and cell division, the *M. jannaschii* genome contains two genes that are putative homologs of Cdc54, a yeast protein that belongs to a family of putative DNA replication initiation proteins (Whitbred, L. A. and Dalton, S., *Gene* 155:113 (1995)). A third potential regulator of cell division in *M. jannaschii* is 55% similar at the amino acid level to pelota, a Drosophila protein involved in the regulation of the early phases of meiotic and mitotic cell division (Eberhart, C. G. and Wasserman, S. A., *Development* 121:3477 (1995)).

In contrast to the putative rfc complex and the initiation of DNA replication, the cell division proteins from *M. jannaschii* most resemble their bactiial counterparts (Rothfield, L. I. and Zhao, C. R., *Cell* 84:183 (1996); Lutkenhaus, J., *Curr. Opp. Gen. Devel.* 3:783 (1993)). Two genes similar to that encoding FtsZ, a ubiquitous bacterial protein, are found in *M. jannaschii*. FtsZ is a polymer-forming, guanosine triphosphate (GTP)-hydrolyzing protein with tubulin-like elements; it is localized to the site of septation and forms a constricting ring between the dividing cells. One gene similar to FtsJ, a bacterial cell division protein of undetermined function, also is found in *M. jannaschii*. Three additional genes (MinC, MinD, and MinE) function in concert in Bacteria to determine the site of septation during cell division. In *M. jannaschii*, three MinD-like genes were identified, but none for MinC or MinE. Neither spindle-associated proteins characteristic of eukaryotic cell division nor bacterial mechanocherical enzymes necessary for partitioning the condensed chromosomes were detected in the *M. jannaschii* genome. Taken together, these observations raise the possibility that cell division in *M. jannaschii* might occur via a mechanism specific for the Archaea.

The structural and functional conservation of the signal peptide of secreted proteins in Archaea, Bacteria, and Eukaryotes suggests that the basic mechanisms of membrane targeting and translocation may be similar among all three domains of life. The secretory machinery of *M. jannaschii* appears a rudimentary apparatus relative to that of bacterial and eukaryotic systems and consists of (i) a signal peptidase (SP) that cleaves the signal peptide of translocating proteins, (ii) a preprotein translocase that is the major constituent of the membrane-localized translocation channel, (iii) a ribonucleoprotein complex (signal recognition particle, SRP) that binds to the signal peptide and guides nascent proteins to the cell membrane, and (iv) a docking protein that acts as a receptor for the SRP. The 7S RNA component of the SRP from *M. jannaschii* shows a highly conserved structural domain shared by other Archaea, Bacteria, and Eukaryotes (Kaine, B. P. and Merkel, V. L., *J. Bacteriol.* 171:4261 (1989); Poritz, M. A. et al., *Cell* 55:4 (1988)). However, the predicted secondary structure of the 7S RNA SRP component in Archaea is more like that found in Eukaryotes than in Bacteria (Kaine, B. P. and Merkel, V. L., *J. Bacteriol.* 171:4261 (1989); Poritz, M. A. et al., *Cell* 55:4 (1988)). The SP and docking proteins from *M. jannaschii* are most similar to their eukaryotic counterparts; the translocase is most similar to the SecY translocation-associated protein in *Escherichia coli*.

A second distinct signal peptide is found in the flagellin genes of *M. jannaschii*. Alignment of flagellin genes from *M. voltae* (Faguy, D. M., et al., *Can. J. Microbiol.* 40:67 (1994); Kalmokoff, M. L., et al., *Arch. Microbiol.* 157:481 (1992)) and *M. jannaschii* reveals a highly conserved $NAH_2$-terminus (31 of the first 50 residues are identical in all of the mature flagellins). The peptide sequence of the *M.*

*jannaschii* flagellin indicates that the protein is cleaved after the canonical Gly-12 position, and it is proposed to be similar to type-IV pilins of Bacteria (Faguy, D. M., et al., *Can. J. Microbiol.* 40:67 (1994); Kalmokoff, M. L., et al., *Arch. Microbiol.* 157:481 (1992)).

Five histone genes are present in the *M. jannaschii* genome—three on the main chromosome and two on the large ECE. These genes are homologs of eukaryotic histones (H2a, H2b, H3, and H4) and of the eukaryotic transcription-related CAAT-binding factor CBF-A (Sandman, K., et al., *Proc. Natl. Acad. Sci. USA* 87:5788 (1990)). The similarity between archaeal and eukaryotic histones suggests that the two groups of organisms resemble one another in the roles histones play both in genome supercoiling dynamics and in gene expression. The five *M. jannaschii* histone genes show greatest similarity among themselves even though a histone sequence is available from the closely related species, *Methanococcus voltae*. This intraspecific similarity suggests that the gene duplications that produced the five histone genes occurred on the *M. jannaschii* lineage per se.

Self-splicing portions of a peptide sequence that generally encode a DNA endonuclease activity are called inteins, in analogy to introns (Kane, P. M., et al., *Science* 250:651 (1990); Hirata, R., et al., *J. Biol. Chem.* 265:6726 (1990); Cooper, A. and Stevens, T., *TIBS* 20:351 (1995); Xu, M. Q., et al., *Cell* 75:1371 (1993); Perler et al., *Proc. Natl. Acad. Sci. USA* 89:5577 (1992); Cooper et al., *EMBO J.* 225.75 (1993); Michel et al., *Biochimie* 64:867 (1992); Pietrokovski S., *Prot. Sci.* 3:2340 (1994). Most inteins in the *M. jannaschii* genome were identified by (i) similarity of the bounding exteins to other proteins, (ii) similarity of the inteins to those previously described, (iii) presence of the dodecapeptide endonuclease motifs, and (iv) canonical intein-exteinjunction sequences. In two instances (MJ0832 and MJ0043), the similarity to other database sequences did not unambiguously define the NH$_2$-terminal extein-intein junction, so it was necessary to rely on consensus sequences to select the putative site. The inteins in MJ1042 and MJ0542 have previously uricharacterized COOH-terminal splice junctions, GNC and FNC, respectively).

The sequences remaining after an intein is excised are called exteins, in analogy to exons. Exteins are spliced together after the excision of one or more inteins to form functional proteins. The biological significance and role of inteins are not clearly understood (Kane, P. M., et al., *Science* 250:651 (1990); Hirata, R., et al., *J. Biol. Chem.* 265:6726 (1990); Cooper, A. and Stevens, T., *TIBS* 20:351 (1995); Xu, M. Q., et al., *Cell* 75:1371 (1993); Perler et al., *Proc. Natl. Acad. Sci. USA* 89:5577 (1992); Cooper et al., *EMBO J.* 12:2575 (1993); Michel et al., *Biochimie* 64:867 (1992); Pietrokovski S., *Prot. Sci.* 3:2340 (1994)). Fourteen genes in the *M. jannaschii* genome contain 18 putative inteins, a significant increase in the approximately 10 intein-containing genes that have been described (Kane, P. M., et al., *Science* 250:651 (1990); Hirata, R., et al., *J. Biol. Chem.* 265:6726 (1990); Cooper, A. and Stevens, T., *TIBS* 20:351 (1995); Xu, M. Q., et al., *Cell* 75:1371 (1993); Perler et al., *Proc. Natl. Acad. Sci. USA* 89:5577 (1992); Cooper et al., *EMBO J.* 12:2575 (1993); Michel et al., *Biochimie* 64:867 (1992); Pietrokovski S., *Prot. Sci.* 3:2340 (1994)) (Table 4).

The only previously described inteins in the Archaea are in the DNA polymerase genes of the Thermococcales (Kane, P. M., et al., *Science* 250:651 (1990); Hirata, R., et al., *J. Biol. Chem.* 265:6726 (1990); Cooper, A. and Stevens, T., *TIBS* 20:351 (1995); Xu, M. Q., et al., *Cell* 75:1371 (1993); Perler et al., *Proc. Natl. Acad. Sci. USA* 89:5577 (1992); Cooper et al., *EMBO J.* 12:2575 (1993); Michel et al., *Biochimie* 64:867 (1992); Pietrokovski S., *Prot. Sci.* 3:2340 (1994)). The *M. jannaschi* DNA polymerase gene has two inteins in the same locations as those in Pyrococcus sp. strain KOD1. In this case, the exteins exhibit 46% amino acid identity, whereas intein 2 of the two organisms has only 33% identity. This divergence suggests that intein 2 has not been recently (laterally) transferred between the Thermococcales and *M. jannaschii*. In contrast, the intein 1 sequences are 56% identical, more than that of the gene containing them, and comparable to the divergence of inteins within the Thermococcales. This high degree of sequence similarity might be the result of an intein transfer more recent than the splitting of these species. The large number of inteins found in *M. jannaschii* led us to question whether these inteins have been increasing in number by moving within the genome. If this were so, we would expect to find some pairs of inteins that are particularly similar. Comparisons of these and other available intein sequences showed that the closest relationships are those noted above linking the DNA polymerase inteins to correspondingly positioned elements in the Thermococcales. Within *M. jannaschii*, the highest identity observed was 33% for a 380-bp portion of two inteins. This finding suggests that the diversification of the inteins predates the divergence of the *M. jannaschii* and Pyrococcus DNA polymerases.

Three families of repeated genetic elements were identified in the *M. jannaschii* genome. Within two of the families, at least two members were identified as ORFs with a limited degree of sequence similarity to bacterial transposases. Members of the first family, designated ISAMJ1, are repeated 10 times on the main chromosome and once on the large ECE (FIG. 5). There is no sequence similarity between the IS elements in *M. jannaschii* and the ISM1 mobile element described previously for *Methanobrevibacter smithii* (Hamilton, P. T. et al., *Mol. Gen. Genet.* 200:47 (1985)). Two members of this family were identified as ORFs and are 27% identical (at the amino acid sequence level) to a transposase from *Bacillus thuringiensis* (IS240; GenBank accession number M23741). Relative to these two members, the remaining members of the ISAMJ1 family are missing an internal region of several hundred nucleotides (FIG. 5). With one exception, all members of this family end with 16-bp terminal inverted repeats typical of insertion sequences. One member is missing the terminal repeat at its 5' end. The second family consists of two ORFs that are identical across 928 bp. The ORFs are 23% identical at the amino acid sequence level to the COOH-terminus of a transposase from *Lactococcus lactis* (IS982; GenBank accession number L34754). Neither of the members of the second family contains terminal inverted repeats.

Eighteen copies of the third family of repeated genetic structures (FIG. 6) are distributed fairly evenly around the *M. jannaschii* genome (FIG. 4). Unlike the genetic elements described above, none of the components of this repeat unit appears to have coding potential: The repeat structure is composed of a long segment followed by one to 25 tandem repetitions of a short segment. The short segments are separated by sequence that is unique within and among the complete repeat structure. Three similar types of short segments were identified; however, the type of short repeat is consistent within each repeat structure, except for variation of the last short segment in six repeat structures. Similar tandem repeats of short segments have been observed in Bacteria and other Archaea (Mojica, F. J. M., et al., *Mol. Micro.* 17:85 (1995)) and have been hypothesized to participate in chromosome partitioning during cell division.

The 16-kbp ECE from *M. jannaschii* contains 12 ORFs, none of which had a significant full-length match to any published sequence (FIG. 3). The 58-kbp ECE contains 44 predicted protein-coding regions, 5 of which had matches to genes in the database. Two of the genes are putative archaeal histones, one is a sporulation-related protein (SOJ protein), and two are type I restriction modification enzymes. There are several instances in which predicted protein-coding regions or repeated genetic elements on the large ECE have similar counterparts on the main chromosome of *M. jannaschii* (FIG. 3). The degree of nucleotide sequence similarity between genes present on both the ECE and the main chromosome ranges from 70 to 90%, suggesting that there has been relatively recent exchange of at least some genetic material between the large ECE and the main chromosome.

All the predicted protein-coding regions from *M. jannaschii* were searched against each other in order to identify families of paralogous genes (genes related by gene duplication, not speciation). The initial criterion for grouping paralogs was >30% amino acid sequence identity over 50 consecutive amino acid residues. Groups of predicted protein-coding regions were then aligned and inspected individually to ensure that the sequence similarity extended over most of their lengths. This curatorial process resulted in the identification of more than 100 gene families, half of which have no database matches. The largest identified gene family (16 members) (FIG. 7) contains almost 1% of the total predicted protein-coding regions in *M. jannaschii*.

Despite the availability for comparison of two complete bacterial genomes and several hundred megabase pairs of eukaryotic sequence data, the majority of genes in *M. jannaschii* cannot be identified on the basis of sequence similarity. Previous evidence for the shared common ancestry of the Archaeal and Eukaryotic was based on a small set gene sequences (Iwabe, N., et al., *Proc. Natl. Acad. Sci. USA* 86:9355 (1989); Gogarten J. P., et al., *Proc. Natl. Acad. Sci. USA* 86:6661 (1989); Brown, J. R. and Doolittle, W. F., *Proc. Natl. Acad. Sci. USA* 92:2441 (1995)). The complete genome of *M. jannaschii* allows us to move beyond a "gene by gene" approach to one that encompasses the larger picture of metabolic capacity and cellular systems. The anabolic genes of *M. jannaschii* (especially those related to energy production and nitrogen fixation) reveal an ancient metabolic world shared largely by Bacteria and Archaea. That many basic autotrophic pathways appear to have a common evolutionary origin suggests that the most recent universal common ancestor to all three domains of extant life had the capacity for autotrophy. The Archaea and Bacteria also share structural and organizational features that the most recent universal prokaryotic ancestors also likely possessed, such as circular genomes and genes organized as operons. In contrast, the cellular information-processing and secretion systems in *M. jannaschii* demonstrate the common ancestry of Eukaryotes and Archaea. Although there are components of these systems are present in all three domains, their apparent refinement over time-especially transcription and translation-indicate that the Archaea and Eukaryotes share a common evolutionary trajectory independent of the lineage of Bacteria.

EXAMPLE 2

Preparation of PCR Primers and Amplification of DNA

Various fragments of the *Methanococcus jannaschii* genome, such as those disclosed in Tables 2(a), 2(b) and 3 can be used, in accordance with the present invention, to prepare PCR primers. The PCR primers are preferably at least 15 bases, and more preferably at least 18 bases in length. When selecting a primer sequence, it is preferred that the primer pairs have approximately the same G/C ratio, so that melting temperatures are approximately the same. The PCR primers are useful during PCR cloning of the ORFs described herein.

EXAMPLE 3

Gene expression from DNA Sequences Corresponding to ORFs

A fragment of the *Methanococcus jannaschii* genome (preferably, a protein-encoding sequence) provided in Tables 2(a), 2(b) or 3 is introduced into an expression vector using conventional technology (techniques to transfer cloned sequences into expression vectors that direct protein translation in mammalian, yeast, insect or bacterial expression systems are well known in the art). Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism, as explained by Hatfield et al, U.S. Pat. No. 5,082,767, which is hereby incorporated by reference.

The following is provided as one exemplary method to generate polypeptide(s) from a cloned ORF of the Methanococcus genome whose sequence is provided in SEQ ID NOS:1, 2 and 3. A poly A sequence can be added to the construct by, for example, splicing out the poly A sequence from pSGS (Stratagene) using Bg/I and Sa/I restriction endonuclease enzymes and incorporating it into the mammalian expression vector pXT1 (Stratagene) for use in eukaryotic expression systems. pXT1 contains the LTRs and a portion of the gag gene from Moloney Murine Leukemia Virus. The position of the LTRs in the construct allow efficient stable transfection. The vector includes the Herpes Simplex thymidine kinase promoter and the selectable neomycin gene. The Methanococcus DNA is obtained by PCR from the bacterial vector using oligonucleotide primers complementary to the Methanococcus DNA and containing restriction endonuclease sequences for PstI incorporated into the 5' primer and Bg/II at the 5' end of the corresponding Methanococcus DNA 3' primer, taking care to ensure that the Methanococcus DNA is positioned such that its followed with the poly A sequence. The purified fragment obtained from the resulting PCR reaction is digested with PstI, blunt ended with an exonuclease, digested with Bg/II, purified and ligated to pXT1, now containing a poly A sequence and digested Bg/II.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). The protein is preferably released into the supernatant. However if the protein has membrane binding domains, the protein may additionally be retained within the cell or expression may be restricted to the cell surface.

Since it may be necessary to purify and locate the transfected product, synthetic 15-mer peptides synthesized from the predicted Methanococcus DNA isequence are injected into mice to generate antibody to the polypeptide encoded by the Methanococcus DNA.

If antibody production is not possible, the Methanococcus DNA sequence is additionally incorporated into eukaryotic expression vectors and expressed as a chimeric with, for example, β-globin. Antibody to β-globin is used to purify the chimeric. Corresponding protease cleavage sites engineered between the β-globin gene and the Methanococcus DNA are then used to separate the two polypeptide fragments from one another after translation. One useful expression vector for generating β-globin chimerics is pSG5 (Stratagene). This vector encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are available from the technical assistance representatives from Stratagene, Life Technologies, Inc., or Promega. Polypeptides may additionally be produced from either construct using in vitro translation systems such as In vitro Express™ Translation Kit (Stratagene).

EXAMPLE 4

E. coli Expression of a M. jannaschii ORF and protein purification

A M. jannaschii ORF described in Table 2(a), 2(b), or 3 is selected and amplified using PCR oligonucleotide primers designed from the nucleotide sequences flanking the selected ORF and/or from portions of the ORF's $NH_2$- or COOH-terminus. Additional nucleotides containing restriction sites to facilitate cloning are added to the 5' and 3' sequences, respectively.

The restriction sites are selected to be convenient to restriction sites in the bacterial expression vector pD10 (pQE9), which is used for bacterial expression. (Qiagen, Inc. 9259 Eton Avenue, Chatsworth, Calif., 91311). [pD10]pQE9 encodes ampicillin antibiotic resistance ("Amp") and contains a bacterial origin of replication ("ori"), an IPTG inducible promoter, a ribosome binding site ("RBS"), a 6-His tag and restriction enzyme sites.

The amplified M. jannaschii DNA and the vector pQE9 both are digested with SalI and XbaI and the digested DNAs are then ligated together. Insertion of the M. jannaschii DNA into the restricted pQE9 vector places the M. jannaschii coding region downstream of and operably linked to the vector's IPTG-inducible promoter and in-frame with an initiating AUG appropriately positioned for translation of the M. jannaschii protein.

The ligation mixture is transformed into competent E. coli cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kan"), is used in carrying out the illustrative example described herein. This strain, which is only one of many that are suitable for expressing M. jannaschii protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis. Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin followed by sterile filtration. The sterile filtered protein preparation is stored in 2×PBS at a concentration of 95 µ/ml.

EXAMPLE 5

Cloning and Expression of a M. jannaschii protein in a Baculovirus 25 Expression. System A M. jannaschii ORF described in Table 2(a), 2(b), or 3 is selected and amplified as above. The amplified DNA is isolated from a 1% agarose gel using a commercially available kit ("Gene clean," BIO 101 Inc., La Jolla, Calif.). The DNA then is digested with XbaI and again purified on a 1% agarose gel. This DNA is designated herein as F2.

The vector pA2-GP is used to express the M. jannaschii protein in the baculovirus expression system as described in Summers et al., A Manual of Methods for Baculovirus Vectors and Insect Cell Culture Procedures, Texas Agricultural Experimental Station Bulletin No. 1555 (1987). The pA2-GP expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site from the simian virus 40 ("SV40") is used for efficient polyadenylation. For an easy selection of recombinant virus, the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIMI provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31–39, among others.

The plasmid is digested with the restriction enzyme XbaI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the *M. jannaschii* gene by digesting DNA from individual colonies using XbaI and then analyzing the digestion product by gel electrophoresis. The sequence of the cloned fragment is confirmed by DNA sequencing. This plasmid is designated herein pBac*M. jannaschii*.

5 µg of the plasmid pBac*M. jannaschii* is co-transfected with 1.0 µg of a commercially available linearized baculovirus DNA ("BaculoGold™ baculovirus DNA", Phanningen, San Diego, Calif.), using the lipofection method described by Felgner et al., *Proc. Natl. Acad. Sci. USA* 84: 7413–7417 (1987). 1 µg of BaculoGold™ virus DNA and 5 µg of the plasmid pBac*M. jannaschii* are mixed in a sterile well of a microtiter plate containing 50 µl of serum-free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatant of these culture dishes are harvested and then they are stored at 4° C. A clone containing properly inserted hESSB I, II and III is identified by DNA analysis including restriction mapping and sequencing. This is designated herein as V-*M. jannaschii*.

Sf9 cells are grown in Grace's medium supplemented with 10% heat-inactivated FBS. The cells are infected with the recombinant baculovirus V-*M. jannaschii* at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 µCi of $^{35}$S-methionine and 5 µCi $^{35}$S-cysteine (available from Amersham) are added. The cells are further incubated for 16 hours and then they are harvested by centrifugation, lysed and the labeled proteins are visualized by SDS-PAGE and autoradiography.

EXAMPLE 6

Cloning and Expression in Mammalian Cells

Most of the vectors used for the transient expression of a *M. jannaschii* gene in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein-coding sequence, and signals required for the termination of trancription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkat cells, mouse NIH3T3 and C127 cells, Cos 1, Cos 7 and CV1, African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem J. 227:277–279 (1991); Bebbington et al., Bio/Technology 10:169–175 (1992)). Using these markers, the mammalian cells are grown in selective medium and the cells with the highest resistance are selected. These cell lines contain the amplified genes(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al, Molecular and Cellular Biology, 438–447 (March, 1985)) plus a fragment of the CMV-enhancer (Boshart et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 6(a)

Cloning and Expression in COS Cells

The expression plasmid, pM. jannaschii HA, is made by cloning a cDNA encoding a M. jannaschii protein into the expression vector pcDNAI/Amp (which can be obtained from Invitrogen, Inc.).

The expression vector pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the M. jannaschii protein and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The PCR amplified DNA fragment (generated as described above) and the vector, pcDNAI/Amp, are digested with HindIII and XhoI and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the M. jannaschii protein-encoding fragment.

For expression of recombinant M. jannaschii, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of M. jannaschii protein by the vector.

Expression of the M. jannaschii HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

EXAMPLE 6(b)

Cloning and Expression in CHO Cells

The vector pC1 is used for the expression of a M. jannaschii protein. —Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schirnke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR)

of the Rouse Sarcoma Virus (Cullen, et al., Molecular and Cellular Biology, March 1985:4384470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, PvuII, and NruI. Behind these cloning sites the plasmid contains translational stop codons in all three reading flames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying the gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The *M. jannaschii* protein-encoding sequence is is amplified using PCR oligonucleotide primers as described above. An efficient signal for initiation of translation in eukaryotic cells, as described by Kozak, M., J. Mol. Biol. 196:947–950 (1987) is appropriately located in the vector portion of the construct. The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-cells

Chinese hamster ovary cells lacking an active DHFR enzyme are used for transfection. 5 µg of the expression plasmid C1 are cotransfected with 0.5 µg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 7

Production of an Antibody to a *Methanococcus jannaschii* Protein

Substantially pure *M. jannaschii* protein or polypeptide is isolated from the transfected or transformed cells described above using an art-known method. The protein can also be chemically synthesized. Concentration of protein in the final preparation is adjusted, for example, by concentration on an Amicon filter device, to the level of a few micrograms/ml. Monoclonal or polyclonal antibody to the protein can then be prepared as follows:

Monoclonal Antibody Production by Hybridoma Fusion

Monoclonal antibody to epitopes of any of the peptides identified and isolated as described can be prepared from murine hybridomas according to the -classical method of Kohler, G. and Milstein, C., *Nature* 256:495 (1975) or modifications of the methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the'system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and modified methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2 (1989).

Polyclonal Antibody Production by Immunization

Polyclonal antiserum containing antibodies to heterogenous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than other molecules and may require the use of carriers and adjuvant. Also, host animals vary in response to site of inoculations and dose, with both inadequate or excessive doses of antigen resulting in low titer antisera Small doses (ng level) of antigen administered at multiple intradermal sites appears to be most reliable. An effective immunization protocol for rabbits can be found in Vaitukaitis, J. et al., *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall (See Ouchterlony, O. et al., Chap. 19 in: *Handbook of Experimental Immunology*, Wier, D., ed, Blackwell (1973)). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology*, second edition, Rose and Friedman, (eds.), Amer. Soc. For Microbio., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample.

TABLE 1A

Amino acid biosynthesis

Aromatic amino acid family

| | | | | | | |
|---|---|---|---|---|---|---|
| MJ1454 | 47830 | 48390 | 3-dehydroquinate dehydratase {*Escherichia coli*} | 32.6 | 54.0 | 561 |
| MJ0502 | 1029204 | 1027915 | 5-enolpyruvylshikimate 3-phosphate synthase {*Haemophilus influenzae*} | 38.2 | 60.0 | 1290 |
| MJ1075 | 456842 | 458158 | anthranilate synthase, subunit I {*Clostridium thermocellum*} | 52.7 | 72.1 | 1317 |
| MJ0234 | 1247181 | 1246243 | anthranilate synthase, subunit II' {*Thermotoga maritima*} | 44.1 | 64.3 | 939 |
| MJ0238 | 1242410 | 1241916 | anthranilate synthase, subunit II" {*Thermotoga maritima*} | 52.6 | 75.0 | 495 |
| MJ0246 | 1238364 | 1238660 | chorismate mutase subunit A {*Erwinia herbicola*} | 37.4 | 59.4 | 297 |
| MJ0612 | 929781 | 928723 | chorismate mutase subunit B {*Escherichia coli*} | 33.2 | 56.2 | 1059 |
| MJ1175 | 357469 | 358572 | chorismate synthase {Synechocystis sp} | 48.8 | 66.5 | 1104 |
| MJ0918 | 621924 | 622682 | indole-3-glycerol phosphate synthase {*Halobacterium volcanii*} | 42.7 | 67.7 | 759 |
| MJ0451 | 1068501 | 1067845 | N-phosphoribosyl anthranilate isomerase {*Haloferax volcanii*} | 41.9 | 62.5 | 657 |
| MJ0637 | 904569 | 905264 | prephenate dehydratase {*Lactococcus lactis*} | 39.3 | 61.7 | 696 |
| MJ1084 | 449533 | 448757 | shikimate 5-dehydrogenase {*Escherichia coli*} | 38.9 | 57.4 | 777 |
| MJ1038 | 502619 | 501777 | tryptophan synthase, subunit alpha {*Methanobacterium thermoautotrophicum*} | 49.8 | 69.3 | 843 |
| MJ1037 | 503929 | 502808 | tryptophan synthase, subunit beta {*Acinetobacter calcoaceticus*} | 62.2 | 78.7 | 1122 |

Aspartate family

| | | | | | | |
|---|---|---|---|---|---|---|
| MJ1116 | 414120 | 415679 | asparagine synthetase {*Escherichia coli*} | 34.0 | 54.3 | 1560 |
| MJ1056 | 476613 | 476170 | asparagine synthetase {*Bacillus subtilis*} | 33.0 | 54.6 | 444 |
| MJ1391 | 132691 | 133833 | aspartate aminotransferase {*Sulfolobus solfataricus*} | 31.0 | 52.2 | 1143 |
| MJ0684 | 859565 | 860632 | aspartate aminotransferase {*Sulfolobus solfataricus*} | 37.8 | 63.1 | 1068 |
| MJ0001 | 1469369 | 1470142 | aspartate aminotransferase {*Sulfolobus solfataricus*} | 39.2 | 63.8 | 774 |
| MJ0205 | 1273947 | 1274951 | aspartate-semialdehyde dehydrogenase {*Leptospira interrogans*} | 50.4 | 67.2 | 1005 |
| MJ0571 | 963902 | 962544 | aspartokinase I {*Serratia marcescens*} | 37.0 | 56.7 | 1359 |
| MJ1473 | 26812 | 27558 | cobalamin-independent methionine synthase {*Methanobacterium thermoautotrophicum*} | 47.7 | 65.3 | 747 |
| MJ1097 | 433957 | 435159 | diaminopimelate decarboxylase {*Haemophilus influenzae*} | 43.2 | 66.6 | 1203 |
| MJ1119 | 412913 | 412029 | diaminopimelate epimerase {*Haemophilus influenzae*} | 36.2 | 56.6 | 885 |
| MJ0422 | 1090629 | 1091441 | dihydrodipicolinate reductase {*Haemophilus influenzae*} | 45.0 | 64.4 | 813 |
| MJ0244 | 1239093 | 1239776 | dihydrodipicolinate synthase {*Haemophilus influenzae*} | 46.6 | 64.4 | 684 |
| MJ1003 | 540278 | 539106 | homoaconitase {*Saccharomyces cerevisiae*} | 35.7 | 56.9 | 1173 |
| MJ1602 | 1563296 | 1562289 | homoserine dehydrogenase {*Bacillus subtilis*} | 40.4 | 63.2 | 1008 |
| MJ1104 | 427241 | 428128 | homoserine kinase {*Haemophilus influenzae*} | 30.1 | 53.9 | 888 |
| MJ0020 | 1450056 | 1451210 | L-asparaginase I {*Haemophilus influenzae*} | 34.8 | 53.1 | 1155 |
| MJ0457 | 1064285 | 1063176 | succinyl-diaminopimelate desuccinylase {*Haemophilus influenzae*} | 27.0 | 45.8 | 1110 |
| MJ1465 | 36982 | 38157 | threoninesynthase {*Bacillus subtilis*} | 51.2 | 71.1 | 1176 |

Glutamate family

| | | | | | | |
|---|---|---|---|---|---|---|
| MJ0069 | 1406333 | 1405455 | acetylglutamate kinase {*Bacillus stearothermophilus*} | 44.4 | 65.7 | 879 |
| MJ0791 | 757315 | 758637 | argininosuccinate lyase {*Campylobacter jejuni*} | 41.3 | 65.6 | 1323 |
| MJ0429 | 1087105 | 1086023 | argininosuccinate synthase {*Methanococcus vannielii*} | 70.2 | 86.8 | 1083 |
| MJ0186 | 1287178 | 1288140 | glutamate N-acetyltransferase {*Bacillus stearothermophilus*} | 47.4 | 63.1 | 963 |
| MJ1351 | 172535 | 174007 | glutamate synthase (NADPH), subunit alpha {*Escherichia coli*} | 40.5 | 54.0 | 1473 |
| MJ1346 | 179417 | 178068 | glutamine synthetase {*Methanococcus voltae*} | 70.5 | 84.7 | 1350 |
| MJ1096 | 435486 | 436508 | N-acetyl gamma-glutamyl-phosphate reductase {*Bacillus subtilis*} | 40.4 | 63.6 | 1023 |
| MJ0721 | 817148 | 816045 | N-acetylornithine aminotransferase {Anabaena sp.} | 46.7 | 67.0 | 1104 |
| MJ0881 | 664952 | 665845 | ornithine carbamoyltransferase {*Halobacterium halobium*} | 43.0 | 69.6 | 894 |

Pyruvate family

| | | | | | | |
|---|---|---|---|---|---|---|
| MJ0503 | 1027812 | 1026610 | 2-isopropylmalate synthase {*Lactococcus lactis*} | 44.4 | 61.1 | 1203 |
| MJ1392 | 131826 | 130633 | 2-isopropylmalate synthase {Anabaena sp.} | 43.0 | 63.1 | 1194 |
| MJ1271 | 256614 | 256216 | 3-isopropylmalate dehydratase {*Salmonella typhimurium*} | 44.1 | 62.0 | 399 |
| MJ1277 | 249421 | 249807 | 3-isopropylmalate dehydratase {*Clostridium pasteurianum*} | 49.5 | 70.2 | 387 |
| MJ0663 | 884580 | 883129 | acetolactate synthase, large subunit {*Porphyra umbilicalis*} | 34.5 | 54.6 | 1452 |
| MJ0277 | 1207735 | 1209507 | acetolactate synthase, large subunit {*Bacillus subtilis*} | 50.2 | 69.7 | 1773 |
| MJ0161 | 1307199 | 1307702 | acetolactate synthase, small subunit {*Bacillus subtilis*} | 49.4 | 74.1 | 504 |
| MJ1008 | 533323 | 534132 | branched-chain amino acid aminotransferase {*Escherichia coli*} | 42.6 | 59.0 | 810 |
| MJ1276 | 250052 | 251710 | dihydroxy-acid dehydratase {*Lactococcus lactis*} | 44.6 | 65.1 | 1659 |
| MJ1195 | 333450 | 335003 | isopropylmalate synthase {*Haemophilus influenzae*} | 42.9 | 63.7 | 1554 |
| MJ1543 | 1615932 | 1614931 | ketol-acid reductoisomerase {*Bacillus subtilis*} | 53.7 | 77.0 | 1002 |

Serine family

| | | | | | | |
|---|---|---|---|---|---|---|
| MJ1597 | 1568671 | 1567445 | glycine hydroxymethyltransferase {*Methanobacterium thermoautotrophicum*} | 69.8 | 80.7 | 1227 |
| MJ1018 | 523454 | 524806 | phosphoglycerate dehydrogenase {*Bacillus subtilis*} | 42.7 | 65.4 | 1353 |

TABLE 1A-continued

| | | | | | | |
|---|---|---|---|---|---|---|
| MJ1594 | 1571545 | 1571039 | phosphoserine phosphatase {*Haemophilus influenzae*} | 40.4 | 62.7 | 507 |
| MJ0959 | 580672 | 581778 | serine aminotransferase {*Methanobacterium thermoformicicum*} | 54.5 | 74.9 | 1107 |
| Histidine family | | | | | | |
| MJ1204 | 324063 | 324878 | ATP phosphoribosyltransferase {*Escherichia coli*} | 34.0 | 57.3 | 816 |
| MJ1456 | 46532 | 45354 | histidinol dehydrogenase {*Lactococcus lactis*} | 47.6 | 67.5 | 1179 |
| MJ0955 | 586179 | 585073 | histidinol-phosphate aminotransferase {*Bacillus subtilis*} | 37.7 | 60.8 | 1107 |
| MJ0698 | 848921 | 848364 | imidazoleglycerol-phosphate dehydrogenase {*Methanobacterium thermoautotrophicum*} | 51.7 | 71.2 | 558 |
| MJ0506 | 1024803 | 1025237 | imidazoleglycerol-phosphate synthase (amidotransferase) {*Lactococcus lactis*} | 45.6 | 62.1 | 435 |
| MJ0411 | 1101451 | 1100636 | imidazoleglycerol-phosphate synthase (cyclase) {*Azospirillum brasilense*} | 61.5 | 78.8 | 816 |
| MJ1430 | 71328 | 71047 | phosphoribosyl AMP cyclohydrolase {*Methanococcus vannielii*} | 70.0 | 86.3 | 282 |
| MJ0302 | 1186990 | 1187208 | phosphoribosyl-ATP pyrophosphohydrolase {*Azotobacter chroococcum*} | 54.1 | 68.9 | 219 |
| MJ1532 | 1628155 | 1627745 | phosphoribosylformimino-5-aminoimidazole carboxamide ribotide isomerase {*Methanococcus thermolithotrophicus*} | 51.9 | 81.1 | 411 |
| Biosynthesis of cofactors, prosthetic groups, and carriers | | | | | | |
| MJ0603 | 937289 | 938566 | glutamate-1-semialdehyde aminotransferase {*Bacillus subtilis*} | 51.7 | 70.6 | 1278 |
| MJ0569 | 966316 | 967137 | porphobilinogen deaminase {*Bacillus subtilis*} | 41.2 | 61.4 | 822 |
| MJ0493 | 1035991 | 1036839 | quinolinate phosphoribosyltransferase {*Escherichia coli*} | 39.3 | 61.6 | 849 |
| MJ0407 | 1105699 | 1104965 | quinolinate synthetase {*Cyanophora paradoxa*} | 37.2 | 58.8 | 735 |
| MJ1388 | 136484 | 135309 | S-adenosylhomocysteine hydrolase {*Sulfolobus solfataricus*} | 61.7 | 78.5 | 1176 |
| Biotin | | | | | | |
| MJ1297 | 227704 | 227021 | 6-carboxyhexanoate-CoA ligase {*Bacillus sphaericus*} | 42.2 | 62.2 | 684 |
| MJ1298 | 227005 | 225890 | 8-amino-7-oxononanoate synthase {*Bacillus sphaericus*} | 44.4 | 64.8 | 1116 |
| MJ1300 | 225025 | 223709 | adenosylmethionine-8-amino-7-oxononanoate aminotransferase {*Bacillus sphaericus*} | 39.9 | 64.2 | 1317 |
| MJ1619 | 1543130 | 1543552 | bifunctional protein {*Haemophilus influenzae*} | 25.7 | 54.9 | 423 |
| MJ1296 | 228286 | 228843 | biotin synthetase {*Bacillus sphaericus*} | 38.2 | 62.5 | 558 |
| MJ1299 | 225741 | 225100 | dethiobiotin synthetase {*Bacillus sphaericus*} | 37.0 | 59.0 | 642 |
| Heme and porphyrin | | | | | | |
| MJ1438 | 66330 | 65833 | cobalamin (5'-phosphate) synthase {*Escherichia coli*} | 26.1 | 48.7 | 498 |
| MJ0552 | 983686 | 984417 | cobalamin biosynthesis J protein {*Salmonella typhimurium*} | 26.7 | 51.2 | 732 |
| MJ1314 | 212528 | 211842 | cobalamin biosynthesis protein D {*Pseudomonas denitrificans*} | 38.0 | 61.0 | 687 |
| MJ0022 | 1448163 | 1447273 | cobalamin biosynthesis protein D {*Salmonella typhimurium*} | 35.5 | 61.1 | 891 |
| MJ1569 | 1592308 | 1591700 | cobalamin biosynthesis protein M {*Salmonella typhimurium*} | 29.5 | 54.7 | 609 |
| MJ1091 | 442661 | 443239 | cobalamin biosynthesis protein M {*Salmonella typhimurium*} | 53.7 | 74.4 | 579 |
| MJ0908 | 635150 | 631647 | cobalamin biosynthesis protein N {*Pseudomonas denitrificans*} | 37.5 | 57.6 | 3504 |
| MJ0484 | 1046784 | 1045324 | cobyric acid synthase {*Methanococcus voltae*} | 73.7 | 89.8 | 1461 |
| MJ1421 | 85381 | 86352 | cobyrinic acid a,c-diamide synthase {*Salmonella typhimurium*} | 32.1 | 55.0 | 972 |
| MJ0143 | 1332080 | 1330965 | glutamyl-tRNA reductase {*Methanobacterium thermoautotrophicum*} | 47.8 | 66.9 | 1116 |
| MJ0643 | 899800 | 898910 | porphobilinogen synthase {*Methanothermus sociabilis*} | 62.5 | 79.9 | 891 |
| MJ0930 | 612059 | 611430 | precorrin isomerase {*Salmonella typhimurium*} | 38.7 | 62.0 | 630 |
| MJ0771 | 780420 | 779932 | precorrin-2 methyltransferase {*Salmonella typhimurium*} | 30.4 | 55.9 | 489 |
| MJ0813 | 734876 | 735547 | precorrin-3 methylase {*Salmonella typhimurium*} | 44.2 | 68.4 | 672 |
| MJ1578 | 1583277 | 1582501 | precorrin-3 methylase {*Salmonella typhimurium*} | 54.6 | 76.5 | 777 |
| MJ1522 | 1637017 | 1636385 | precorrin-6Y methylase {*Salmonella typhimurium*} | 30.6 | 52.3 | 633 |
| MJ0391 | 1116729 | 1117202 | precorrin-8W decarboxylase {*Salmonella typhimurium*} | 23.9 | 49.1 | 474 |
| MJ0965 | 573234 | 572509 | uroporphyrin-III C-methyltransferase {*Bacillus megaterium*} | 54.7 | 72.5 | 726 |
| MJ0994 | 549022 | 549444 | uroporphyrinogen III synthase {*Bacillus subtilis*} | 27.8 | 49.4 | 423 |
| Menaquinone and ubiquinone | | | | | | |
| MJ1645 | 1509624 | 1508923 | coenzyme PQQ synthesis protein III {*Haemophilus influenzae*} | 32.2 | 53.3 | 702 |
| Molybdopterin | | | | | | |
| MJ0824 | 725986 | 726762 | molybdenum cofactor biosynthesis moaA protein {*Haemophilus influenzae*} | 30.0 | 57.3 | 777 |
| MJ0167 | 1301836 | 1302162 | molybdenum cofactor biosynthesis moaB protein {*Escherichia coli*} | 46.4 | 69.6 | 327 |
| MJ1135 | 396359 | 396781 | molybdenum cofactor biosynthesis moaC protein {*Haemophilus influenzae*} | 49.2 | 70.9 | 423 |
| MJ0886 | 654158 | 656017 | molybdenum cofactor biosynthesis moeA protein {*Escherichia coli*} | 34.5 | 55.2 | 1860 |
| MJ0666 | 879771 | 880943 | molybdenum cofactor biosynthesis moeA protein {*Haemophiius influenzae*} | 33.6 | 56.4 | 1173 |
| MJ1663 | 1491265 | 1490831 | molybdopterin-guanine dinucleotide biosynthesis protein A {*Escherichia coli*} | 27.7 | 48.0 | 435 |
| MJ1324 | 197777 | 197076 | molybdopterin-guanine dinucleotide biosynthesis protein B {*Escherichia coli*} | 32.2 | 57.7 | 702 |
| Pantothenate | | | | | | |
| MJ0913 | 626982 | 627779 | pantothenate metabolism flavoprotein {*Haemophilus influenzae*} | 34.1 | 55.7 | 798 |
| Riboflavin | | | | | | |
| MJ0055 | 1416688 | 1417278 | GTP cyclohydrolase II {*Bacillus subtilis*} | 35.8 | 56.0 | 591 |
| MJ0671 | 874773 | 875396 | riboflavin-specific deaminase {*Actinobacillus pleuropneumoniae*} | 43.0 | 65.3 | 624 |
| Thioredoxin, glutaredoxin, and glutathione | | | | | | |
| MJ1536 | 1622694 | 1623533 | thioredoxin reductase {*Mycoplasma genitalium*} | 38.5 | 58.0 | 840 |
| MJ0530 | 1005917 | 1005420 | thioredoxin-2 {*Saccharomyces cerevisiae*} | 33.0 | 63.3 | 498 |
| MJ0307 | 1184114 | 1184332 | thioredoxin/glutaredoxin {*Methanobacterium thermoautotrophicum*} | 48.7 | 69.5 | 219 |

TABLE 1A-continued

Thiamine

| | | | | | | |
|---|---|---|---|---|---|---|
| MJ1026 | 514172 | 515440 | thiamine biosynthesis protein {*Bacillus subtilis*} | 45.0 | 66.1 | 1269 |
| MJ0601 | 940113 | 939400 | thiamine biosynthetic enzyme {*Zea mays*} | 35.1 | 53.0 | 714 |

Pyridine nucleotides

| | | | | | | |
|---|---|---|---|---|---|---|
| MJ1352 | 170567 | 171163 | NH(3)-dependent NAD+ synthetase {*Mycoplasma genitalium*} | 47.5 | 63.8 | 597 |

Cell envelope

Membranes, lipoproteins, and porins

| | | | | | | |
|---|---|---|---|---|---|---|
| MJ0544 | 989805 | 990443 | dolichyl-phosphate mannose synthase {*Trypanosoma brucei*} | 35.1 | 57.1 | 639 |
| MJ1057 | 475508 | 474981 | glycosyl transferase {*Neisseria gonorrhoeae*} | 25.8 | 50.0 | 528 |
| MJ0611 | 931098 | 930679 | membrane protein {Saccharum sp.} | 50.0 | 57.2 | 420 |
| MJ0827 | 724322 | 723900 | membrane protein {*Homo sapiens*} | 44.9 | 67.0 | 423 |

Murein sacculus and peptidoglycan

| | | | | | | |
|---|---|---|---|---|---|---|
| MJ1160 | 371691 | 370390 | amidase {*Moraxella catarrhalis*} | 24.6 | 36.1 | 1302 |
| MJ0204 | 1276277 | 1275219 | amidophosphoribosyltransferase {*Bacillus subtillis*} | 52.0 | 72.9 | 1059 |

Surface polysaccharides, lipopolysaccharides and antigens

| | | | | | | |
|---|---|---|---|---|---|---|
| MJ0924 | 617598 | 618035 | capsular polysaccharide biosynthesis protein {*Staphylococcus aureus*} | 31.3 | 46.9 | 438 |
| MJ1061 | 469649 | 470293 | capsular polysaccharide biosynthesis protein D {*Staphylococcus aureus*} | 56.3 | 72.2 | 645 |
| MJ1055 | 478643 | 477735 | capsular polysaccharide biosynthesis protein I {*Staphylococcus aureus*} | 50.7 | 74.4 | 909 |
| MJ1059 | 472326 | 471904 | capsular polysaccharide biosynthsis protein M {*Staphylococcus aureus*} | 34.4 | 55.0 | 423 |
| MJ1607 | 1555624 | 1554455 | LPS biosynthesis related rfbu-protein {*Haemophilus influenzae*} | 33.4 | 57.6 | 1170 |
| MJ1113 | 417528 | 418352 | N-acetylglucosamine-1-phosphate transferase {*Sulfolobus acidocaldarius*} | 29.9 | 57.9 | 825 |
| MJ0399 | 1110873 | 1112204 | phosphomannomutase {*Vibrio cholerae*} | 37.0 | 57.8 | 1332 |
| MJ1068 | 462901 | 464265 | putative O-antigen transporter {*Shigella flexneri*} | 24.5 | 46.6 | 1365 |
| MJ1066 | 464369 | 465430 | spore coat polysaccharide biosynthesis protein C {*Bacillus subtillis*} | 55.3 | 75.8 | 1062 |
| MJ1065 | 465444 | 466454 | spore coat polysaccharide biosynthesis protein E {*Bacillus subtilis*} | 37.9 | 59.0 | 1011 |
| MJ1063 | 467331 | 467828 | spore coat polysaccharide biosynthesis protein F {*Bacillus subtillis*} | 36.0 | 55.4 | 498 |
| MJ1062 | 467870 | 469279 | spore coat polysaccharide biosynthesis protein G {*Bacillus subtillis*} | 32.0 | 54.5 | 1410 |
| MJ0211 | 1269601 | 1268732 | UDP-glucose 4-epimerase {*Streptococcus thermophilus*} | 35.1 | 54.8 | 870 |
| MJ1054 | 481027 | 478712 | UDP-glucose dehydrogenase {*Xanthomonas campestris*} | 42.8 | 63.4 | 2316 |
| MJ0428 | 1087456 | 1088655 | UDP-N-acetyl-D-mannosaminuronic acid dehydrogenase {*Escherichia coli*} | 45.1 | 68.2 | 1200 |

Surface structures

| | | | | | | |
|---|---|---|---|---|---|---|
| MJ0891 | 650616 | 650005 | flagellin 31 {*Methanococcus voltae*} | 55.4 | 71.6 | 612 |
| MJ0892 | 649880 | 649269 | flagellin 32 {*Methanococcus voltae*} | 61.1 | 78.4 | 612 |
| MJ0893 | 649163 | 648516 | flagellin 33 {*Methanococcus voltae*} | 59.1 | 78.7 | 648 |

Cellular processes

Cell division

| | | | | | | |
|---|---|---|---|---|---|---|
| MJ1489 | 10595 | 8721 | cell division control protein {*Saccharomyces cerevisiae*} | 34.8 | 57.7 | 1875 |
| MJ0363 | 1142460 | 1140220 | cell division control protein 21 {*Schizosaccharomyces pombe*} | 30.0 | 51.4 | 2241 |
| MJ1156 | 375317 | 377947 | cell division control protein CDC48 {*Saccharomyces cerevisiae*} | 51.9 | 71.7 | 2631 |
| MJ0169 | 1300988 | 1300329 | cell division inhibitor {*Bacillus subtillis*} | 28.8 | 51.2 | 660 |
| MJ0579 | 957291 | 958088 | cell division inhibitor {*Bacillus subtillis*} | 31.8 | 53.2 | 798 |
| MJ0547 | 988025 | 988732 | cell division inhibitor {*Bacillus subtillis*} | 32.8 | 57.7 | 708 |
| MJ0084 | 1393471 | 1392869 | cell division inhibitor minD {*Escherichia coli*} | 32.1 | 50.4 | 603 |
| MJ0174 | 1295971 | 1294976 | cell division protein {*Drosophila melanogaster*} | 28.4 | 54.6 | 996 |
| MJ0370 | 1135876 | 1134956 | cell division protein ftsZ {Anabaena 7120} | 50.7 | 71.7 | 921 |
| MJ1376 | 147975 | 147343 | cell division protein J {*Haemophilus influenzae*} | 39.8 | 58.5 | 633 |
| MJ0622 | 920029 | 921168 | cell division protein Z {*Haloferax volcanii*} | 51.0 | 71.7 | 1140 |
| MJ0148 | 1326798 | 1327538 | centromere/microtubule-binding protein {*Saccharomyces cerevisiae*} | 42.7 | 64.7 | 741 |
| MJ1647 | 1508164 | 1507907 | DNA binding protein {*Methanococcus voltae*} | 54.7 | 80.3 | 258 |
| MJ1643 | 1513857 | 1510351 | P115 protein {*Mycoplasma hyorhinis*} | 30.3 | 55.4 | 3507 |

Chaperones

| | | | | | | |
|---|---|---|---|---|---|---|
| MJ0999 | 543921 | 545471 | chaperonin {*Methanopyrus kandleri*} | 73.5 | 87.6 | 1551 |
| MJ0285 | 1202058 | 1202459 | heat shock protein {*Clostridium acetobutylicum*} | 29.0 | 44.6 | 402 |
| MJ0278 | 1207276 | 1207548 | rotamase, peptidyl-prolyl cis-trans isomerase {*Haemophilus influenzae*} | 40.7 | 60.5 | 273 |
| MJ0825 | 725091 | 725765 | rotamase, peptidyl-prolyl cis-trans isomerase {*Pseudomonas fluorescens*} | 31.8 | 60.8 | 675 |

Detoxification

| | | | | | | |
|---|---|---|---|---|---|---|
| MJ0736 | 804803 | 805453 | alkyl hydroperoxide reductase {*Sulfolobus solfataricus*} | 66.1 | 84.8 | 651 |
| MJ1541 | 1618786 | 1619868 | N-ethylammeline chlorohydrolase {*Rhodococcus rubropertinctus*} | 29.2 | 56.3 | 1083 |

Protein and peptide secretion

| | | | | | | |
|---|---|---|---|---|---|---|
| MJ0478 | 1051985 | 1056078 | preprotein translocase secY {*Methanococcus vannielii*} | 70.9 | 88.8 | 1308 |
| MJ0111 | 1365253 | 1364216 | protein-export membrane protein {*Streptomyces coelicolor*} | 25.9 | 51.7 | 1038 |
| MJ1253 | 276673 | 277377 | protein-export membrane protein {*Escherichia coli*} | 30.5 | 57.0 | 705 |
| MJ0260 | 1226090 | 1226644 | signal peptidase {*Canis familiaris*} | 32.6 | 54.5 | 555 |
| MJ0101 | 1376106 | 1377308 | signal recognition particle protein {*Haemophilus influenzae*} | 42.0 | 61.6 | 1203 |
| MJ0291 | 1198470 | 1197244 | signal recognition particle protein {*Sulfolobus acidocaldarius*} | 48.3 | 69.4 | 1227 |

TABLE 1A-continued

Transformation

| | | | | | | |
|---|---|---|---|---|---|---|
| MJ0781 | 768702 | 770798 | klbA protein {Plasmid RK2} | 34.6 | 54.9 | 2097 |
| MJ0940 | 602402 | 601929 | transformation sensitive protein {Homo sapiens} | 35.0 | 53.9 | 474 |

Cellular processes

| | | | | | | |
|---|---|---|---|---|---|---|
| MJECL17 | 20110 | 19889 | archaeal histone {Pyrococcus sp.} | 58.8 | 81.0 | 221 |
| MJECL29 | 36456 | 26220 | archaeal histone {Pyrococcus sp.} | 64.2 | 83.6 | 236 |
| MJ1258 | 271686 | 271486 | archaeal histone {Pyrococcus sp.} | 71.7 | 83.6 | 201 |
| MJ0168 | 1301348 | 1301548 | archaeal histone {Pyrococcus sp.} | 67.2 | 86.6 | 201 |
| MJ0932 | 610153 | 609953 | archaeal histone {Pyrococcus sp.} | 67.2 | 86.6 | 201 |

Central intermediary metabolism

Amino sugars

| | | | | | | |
|---|---|---|---|---|---|---|
| MJ1420 | 90244 | 86939 | glutamine-fructose-6-phosphate transaminase {Escherichia coli} | 41.2 | 61.5 | 3306 |

Degradation of polysaccharides

| | | | | | | |
|---|---|---|---|---|---|---|
| MJ1611 | 1550816 | 1549542 | alpha-amylase {Pyrococcus furiosus} | 27.0 | 50.5 | 1275 |
| MJ0555 | 981500 | 980529 | endoglucanase {Homo sapiens} | 44.1 | 66.8 | 972 |
| MJ1610 | 1551992 | 1550967 | glucoamylase {Clostridium sp} | 28.0 | 49.2 | 1026 |

Other

| | | | | | | |
|---|---|---|---|---|---|---|
| MJ1656 | 1498675 | 1497965 | 2-hydroxyhepta-2,4-diene-1,7-dioate isomerase {Escherichia coli} | 40.2 | 61.6 | 711 |
| MJ0406 | 1106800 | 1105907 | ribokinase {Escherichia coli} | 23.2 | 46.3 | 894 |
| MJ0309 | 1182259 | 1183077 | ureohydrolase {Methanothermus fervidus} | 40.9 | 60.7 | 819 |

Phosphorus compounds

| | | | | | | |
|---|---|---|---|---|---|---|
| MJ0963 | 575418 | 577049 | N-methylhydantoinase {Arthrobacter sp.} | 32.6 | 53.0 | 1632 |
| MJ0964 | 573516 | 575345 | N-methylhydantoinase {Arthrobacter sp.} | 37.7 | 56.4 | 1830 |

Polyamine biosynthesis

| | | | | | | |
|---|---|---|---|---|---|---|
| MJ0535 | 1001006 | 1002031 | acetylpolyamine aminohydrolase {D01044 Mycoplana} | 33.3 | 48.6 | 1026 |
| MJ0313 | 1179250 | 1179801 | spermidine synthase {Homo sapiens} | 32.3 | 57.7 | 552 |

Polysaccharides-(cytoplasmic)

| | | | | | | |
|---|---|---|---|---|---|---|
| MJ1606 | 1555858 | 1551354 | glycogen synthase {Hordeum vulgare} | 33.7 | 58.3 | 1497 |

Nitrogen metabolism

| | | | | | | |
|---|---|---|---|---|---|---|
| MJ1187 | 345237 | 344335 | ADP-ribosylglycohydrolase (draG) {Rhodospirillum rubrum} | 29.8 | 50.8 | 903 |
| MJ0713 | 824113 | 826278 | hydrogenase accessory protein {Azotobacter chroococcum} | 33.8 | 54.8 | 2166 |
| MJ0214 | 1267658 | 1267314 | hydrogenase accessory protein {Azotobacter chroococcum} | 30.7 | 56.5 | 345 |
| MJ0676 | 869311 | 870276 | hydrogenase expression/formation protein {Rhizobium leguminosarum} | 46.1 | 65.3 | 966 |
| MJ0442 | 1075480 | 1076028 | hydrogenase expression/formation protein B {Rhizobium leguminosarum} | 44.6 | 64.0 | 549 |
| MJ0200 | 1279494 | 1279739 | hydrogenase expression/formation protein C {Azotobacter vinelandii} | 40.0 | 68.8 | 246 |
| MJ0993 | 549539 | 550525 | hydrogenase expression/formation protein D {Alcaligenes eutrophus} | 44.7 | 63.5 | 987 |
| MJ0631 | 914544 | 914089 | hydrogenase maturation protease {Escherichia coli} | 33.9 | 58.9 | 456 |
| MJ1093 | 441468 | 440584 | nifB protein {Anabaena sp} | 43.1 | 67.2 | 885 |
| MJ0879 | 667622 | 666984 | nitrogenase reductase {Methanococcus voltae} | 77.2 | 89.1 | 639 |
| MJ0685 | 859442 | 858696 | nitrogenase reductase related protein {Clostridium pasteurianum} | 31.7 | 49.6 | 747 |
| MJ1051 | 483344 | 484411 | nodulation factor production protein {Bradyrhizobium japonicum} | 32.1 | 51.1 | 1068 |
| MJ1058 | 473947 | 473141 | nodulation factor production protein {Bradyrhizobium japonicum} | 37.7 | 58.0 | 807 |

Carbon Fixation

| | | | | | | |
|---|---|---|---|---|---|---|
| MJ0152 | 1325036 | 1322820 | carbon monoxide dehydrogenase, alpha subunit {Clostridium thermoaceticum} | 42.1 | 65.6 | 2217 |
| MJ0153 | 1322553 | 1320256 | carbon monoxide dehydrogenase, alpha subunit {Methanothrix soehngenii} | 47.9 | 67.3 | 2298 |
| MJ0156 | 1319256 | 1317883 | carbon monoxide dehydrogenase, alpha subunit {Clostridium thermoaceticum} | 47.8 | 69.5 | 1374 |
| MJ0728 | 809951 | 811783 | carbon monoxide dehydrogenase, beta subunit {Rhodospirillum rubrum} | 35.9 | 55.0 | 1833 |
| MJ0112 | 1362285 | 1363667 | corrinoid/iron sulfur protein, large subunit {Clostridium thermoaceticum} | 32.9 | 55.1 | 1383 |
| MJ0113 | 1361128 | 1362030 | corrinoid/iron sulfur protein, small subunit {Clostridium thermoaceticum} | 37.7 | 58.8 | 903 |
| MJ1235 | 292453 | 293673 | ribulose bisphosphate carboxylase, large subunit {Synechococcus sp} | 42.4 | 60.3 | 1221 |

Energy metabolism

Aerobic

| | | | | | | |
|---|---|---|---|---|---|---|
| MJ0649 | 896262 | 894919 | NADH oxidase {Enterococcus faecalis} | 28.0 | 50.4 | 1344 |
| MJ0520 | 1011104 | 1011892 | NADH-ubiquinone oxidoreductase, subunit 1 {Paracentrotus lividus} | 29.5 | 53.9 | 789 |

Anaerobic

| | | | | | | |
|---|---|---|---|---|---|---|
| MJ0092 | 1385748 | 1384282 | fumarate reductase {Thermoplasma acidophilum} | 40.2 | 57.0 | 1467 |

ATP-proton motive force interconversion

| | | | | | | |
|---|---|---|---|---|---|---|
| MJ0217 | 1263468 | 1265171 | ATP synthase, subunit A {Enterococcus hirae} | 60.3 | 76.6 | 1704 |
| MJ0216 | 1265356 | 1266615 | ATP synthase, subunit B {Methanosarcina barkeri} | 69.4 | 84.5 | 1260 |
| MJ0219 | 1261985 | 1263040 | ATP synthase, subunit C {Haloferax volcanii} | 28.1 | 50.0 | 1056 |
| MJ0615 | 926124 | 926663 | ATP synthase, subunit D {Enterococcus hirae} | 34.8 | 56.8 | 540 |
| MJ0220 | 1261297 | 1261737 | ATP synthase, subunit E {Methanosarcina mazeii} | 29.0 | 50.0 | 441 |

TABLE 1A-continued

| | | | | | | |
|---|---|---|---|---|---|---|
| MJ0218 | 1263054 | 1263347 | ATP synthase, subunit F {*Haloferax volcanii*} | 21.5 | 52.1 | 294 |
| MJ0222 | 1258252 | 1260294 | ATP synthase, subunit I {*Enterococcus hirae*} | 27.6 | 52.2 | 2043 |
| MJ0221 | 1260641 | 1261060 | ATP synthase, subunit K {*Enterococcus hirae*} | 34.6 | 59.8 | 420 |
| Electron transport | | | | | | |
| MJ1446 | 57416 | 56646 | cytochrome-c3 hydrogenase, gamma chain {*Pyrococcus furiosus*} | 40.1 | 52.4 | 771 |
| MJ0741 | 803000 | 803320 | desulfoferrodoxin {*Desulfovibrio vulgaris*} | 44.0 | 59.4 | 321 |
| MJ0578 | 958094 | 958900 | ferredoxin {*Clostridium sticklandii*} | 49.1 | 56.9 | 807 |
| MJ0061 | 1411998 | 1411759 | ferredoxin {*Methanococcus thermolithotrophicus*} | 42.9 | 59.0 | 240 |
| MJ0722 | 815808 | 816038 | ferredoxin {*Methanobacterium thermoautotrophicum*} | 42.3 | 60.6 | 231 |
| MJ0099 | 1379076 | 1379456 | ferredoxin {*Desulfovibrio desulfuricans*} | 40.0 | 62.0 | 381 |
| MJ0199 | 1279976 | 1279791 | ferredoxin {*Methanococcus thermolithotrophicus*} | 74.6 | 84.8 | 186 |
| MJ0533 | 1003408 | 1003575 | ferredoxin 2[4Fe—4S] homolog {*Methanosarcina thermophila*} | 36.9 | 54.4 | 168 |
| MJ0624 | 918981 | 918808 | ferredoxin 2[4Fe=4S] {*Methanosarcina thermophila*} | 48.0 | 68.0 | 174 |
| MJ0267 | 1217567 | 1218463 | ferredoxin oxidoreductase, alpha subunit {*Klebsiella pneumoniae*} | 29.4 | 50.2 | 897 |
| MJ0276 | 1209645 | 1210727 | ferredoxin oxidoreductase, alpha subunit {*Halobacterium halobium*} | 44.5 | 63.0 | 1083 |
| MJ0266 | 1218644 | 1219387 | ferredoxin oxidoreductase, beta subunit {*Klebsiella pneumoniae*} | 32.6 | 51.0 | 744 |
| MJ0537 | 998693 | 999424 | ferredoxin oxidoreductase, beta subunit {*Halobacteriuin halobiuin*} | 41.3 | 61.1 | 732 |
| MJ0268 | 1217015 | 1217272 | ferredoxin oxidoreductase, delta subunit {*Pyrococcus furiosus*} | 58.9 | 71.8 | 258 |
| MJ0536 | 999441 | 999980 | ferredoxin oxidoreductase, gamma subunit {*Pyrococcus furiosus*} | 32.0 | 50.9 | 540 |
| MJ0269 | 1216601 | 1216993 | ferredoxin oxidoreductase, gamma subunit {*Pyrococcus furiosus*} | 55.6 | 74.7 | 393 |
| MJ0732 | 806970 | 808100 | flavoprotein {*Methanobacterium thermoautotrophicum*} | 40.4 | 62.3 | 1131 |
| MJ1192 | 339066 | 338095 | methylviologen-reducing hydrogenase, alpha chain {*Methanococcus voltae*} | 75.0 | 88.6 | 972 |
| MJ1191 | 340221 | 339385 | methylviologen-reducing hydrogenase, gamma chain {*Methanococcus voltae*} | 71.5 | 83.3 | 837 |
| MJ1362 | 160414 | 161055 | NADH deydrogenase, subunit 1 {*Mitochondrion Oncorhynchus*} | 23.1 | 50.0 | 642 |
| MJ0514 | 1016474 | 1017223 | polyferredoxin {*Methanococcus voltae*} | 36.7 | 52.5 | 750 |
| MJ0934 | 608147 | 607521 | polyferredoxin {*Methanothermus fervidus*} | 40.9 | 54.3 | 627 |
| MJ1303 | 220214 | 221701 | polyferredoxin {*Methanobacterium thermoautotrophicum*} | 39.5 | 56.1 | 1488 |
| MJ1193 | 337655 | 336591 | polyferredoxin {*Methanococcus voltae*} | 61.7 | 74.5 | 1065 |
| MJ1227 | 301853 | 301257 | pyruvate formate-lyase activating enzyme {*Clostridium pasteurianum*} | 31.4 | 50.0 | 597 |
| MJ0735 | 805546 | 805785 | rubredoxin {*Clostridium thermosaccharolyticum*} | 59.7 | 77.0 | 240 |
| MJ0740 | 803522 | 803659 | rubredoxin {*Clostridium thermosaccharolyticum*} | 64.5 | 84.5 | 138 |
| Fermentation | | | | | | |
| MJ0007 | 1463447 | 1462359 | 2-hydroxyglutaryl-CoA dehydratase, subunit beta {*Acidaminococcus fermentans*} | 22.6 | 48.2 | 1089 |
| Gluconeogenesis | | | | | | |
| MJ1479 | 22527 | 21358 | alanine aminotransferase 2 {*Panicum miliaceum*} | 30.1 | 50.0 | 1170 |
| MJ0542 | 991264 | 994794 | phosphoenolpyruvate synthase {*Pyrococcus furiosus*} | 60.3 | 78.3 | 3531 |
| Glycolysis | | | | | | |
| MJ1482 | 18946 | 18044 | 2-phosphoglycerate kinase {*Methanothermus fervidus*} | 47.1 | 70.9 | 903 |
| MJ0641 | 901393 | 902325 | 3-phosphoglycerate kinase {*Methanothermus fervidus*} | 58.2 | 78.1 | 933 |
| MJ0232 | 1248239 | 1249432 | enolase {*Bacillus subtilis*} | 57.7 | 78.2 | 1194 |
| MJ1605 | 1557395 | 1558597 | glucose-6-phosphate isomerase {*Bacillus stearothermophilus*} | 32.3 | 54.6 | 1203 |
| MJ1146 | 386093 | 387055 | glyceraldehyde 3-phosphate dehydrogenase {*Methanothermus fervidus*} | 59.5 | 77.6 | 963 |
| MJ0490 | 1038560 | 1037697 | lactate dehydrogenase {*Thermotoga maritima*} | 39.9 | 63.2 | 864 |
| MJ1411 | 100555 | 99167 | NADP-dependent glyceraldehyde-3-phosphate dehydrogenase {L15191 Streptococcus} | 39.2 | 59.6 | 1389 |
| MJ0108 | 1367951 | 1366716 | pyruvate, kinase {*Bacillus stearothermophilus*} | 39.1 | 60.5 | 1236 |
| MJ1528 | 1631071 | 1631589 | triosephosphate isomerase {*Mycoplasma genitalium*} | 29.0 | 49.1 | 519 |
| Pentose phosphate pathway | | | | | | |
| MJ0680 | 865484 | 866083 | pentose-5-phosphate-3-epimerase {*Solanum tuberosum*} | 44.2 | 62.5 | 600 |
| MJ1603 | 1560724 | 1560047 | ribose 5-phosphate isomerase {*Mus musculus*} | 42.0 | 63.4 | 678 |
| MJ0960 | 580121 | 580576 | transaldolase {*Bacillus subtilis*} | 60.7 | 79.5 | 456 |
| MJ0681 | 864603 | 865355 | transketolase' {*Homo sapiens*} | 43.7 | 58.5 | 753 |
| MJ0679 | 866375 | 867073 | transketolase" {*Homo sapiens*} | 36.0 | 61.3 | 699 |
| Pyruvate dehydrogenase | | | | | | |
| MJ0636 | 906464 | 905292 | dihydrolipoamide dehydrogenase {*Haloferax volcanii*} | 28.9 | 51.0 | 1173 |
| Sugars | | | | | | |
| MJ1418 | 91211 | 90669 | fuculose-1-phosphate aldolase {*Haemophilus influenzae*} | 29.1 | 48.7 | 543 |
| TCA cycle | | | | | | |
| MJ0499 | 1031331 | 1032530 | aconitase {*Saccharomyces cerevisiae*} | 29.7 | 49.8 | 1200 |
| MJ1294 | 229770 | 230381 | fumarate hydratase, class I' {*Bacillus stearothermophilus*} | 35.1 | 55.7 | 612 |
| MJ0617 | 925239 | 924778 | fumarate hydratase, class I" {*Bacillus stearothermophilus*} | 43.8 | 66.0 | 462 |
| MJ1596 | 1568967 | 1569998 | isocitrate dehydrogenase {*Thermus aquaticus*} | 42.9 | 61.4 | 1032 |
| MJ0720 | 817433 | 818431 | isocitrate dehydrogenase (NADP) {*Thermus aquaticus*} | 48.0 | 64.7 | 999 |
| MJ1425 | 77051 | 76299 | malate dehydrogenase {*Methanothermus fervidus*} | 61.3 | 77.6 | 753 |
| MJ0033 | 1438609 | 1437116 | succinate dehydrogenase, flavoprotein subunit {*Escherichia coli*} | 41.8 | 58.1 | 1494 |
| MJ1246 | 282664 | 283449 | succinyl-CoA synthetase, alpha subunit {*Escherichia coli*} | 59.6 | 74.8 | 786 |
| MJ0210 | 1271318 | 1270227 | succinyl-CoA synthetase, beta subunit {*Thermus aquaticus*} | 48.8 | 68.7 | 1092 |
| Methanogenesis | | | | | | |
| MJ0253 | 1232773 | 1232405 | 8-hydroxy-5-deazaflavin-reducing hydrogenase, delta subunit {*Methanobacterium thermoautotrophicum*} | 47.1 | 71.0 | 369 |

TABLE 1A-continued

| MJ1035 | 505234 | 506022 | coenzyme F420-dependent N5,N10-methylene-tetrahydromethanopterin dehydrogenase {*Methanobacterium thermoautotrophicum*} | 66.5 | 79.8 | 789 |
|---|---|---|---|---|---|---|
| MJ0727 | 811895 | 812725 | coenzyme F420-reducing hydrogenase, alpha subunit {*Methanobacterium thermoautotrophicum*} | 26.8 | 45.8 | 831 |
| MJ0029 | 1442517 | 1441279 | coenzyme F420-reducing hydrogenase, alpha subunit {*Methanococcus voltae*} | 50.3 | 66.1 | 1239 |
| MJ0030 | 1441022 | 1440558 | coenzyme F420-reducing hydrogenase, alpha subunit {*Methanococcus voltae*} | 66.5 | 83.3 | 465 |
| MJ1349 | 175566 | 176222 | coenzyme F420-reducing hydrogenase, beta subunit {*Methanococcus voltae*} | 36.6 | 55.7 | 657 |
| MJ0725 | 813779 | 814453 | coenzyme F420-reducing hydrogenase, beta subunit {*Methanobacterium thermoautotrophicum*} | 41.0 | 62.0 | 675 |
| MJ0870 | 677657 | 679372 | coenzyme, F420-reducing hydrogenase, beta subunit {*Methanobacterium thermoautotrophicum*} | 42.7 | 63.2 | 1716 |
| MJ0032 | 1439835 | 1438990 | coenzyme F420-reducing hydrogenase, beta subunit {*Methanococcus voltae*} | 72.0 | 85.5 | 846 |
| MJ0726 | 812987 | 813499 | coenzyme F420-reducing hydrogenase, gamma subunit {*Methanococcus voltae*} | 42.7 | 59.4 | 513 |
| MJ0031 | 1440505 | 1439873 | coenzyme F420-reducing hydrogenase, gamma subunit {*Methanococcus voltae*} | 75.5 | 87.3 | 633 |
| MJ0295 | 1192687 | 1193304 | formate dehydrogenase (fdhD) {*Wolinella succinogenes*} | 35.6 | 57.7 | 618 |
| MJ0006 | 1463887 | 1465020 | formate dehydrogenase, alpha subunit {*Methanobacterium formicicum*} | 41.6 | 61.1 | 1134 |
| MJ1353 | 168767 | 170344 | formate dehydrogenase, alpha subunit {*Methanobacterium formicicum*} | 54.2 | 70.9 | 1578 |
| MJ0005 | 1465405 | 1466247 | formate dehydrogenase, beta subunit {*Methanobacterium formicicum*} | 49.5 | 72.1 | 843 |
| MJ0155 | 1319767 | 1319315 | formate dehydrogenase, iron-sulfur subunit {*Wolinella succinogenes*} | 41.7 | 56.9 | 453 |
| MJ0264 | 1220122 | 1220433 | formate hydrogenlyase, subunit 2 {*Escherichia coli*} | 42.9 | 59.8 | 312 |
| MJ0265 | 1219502 | 1219930 | formate hydrogenlyase, subunit 2 {*Escherichia coli*} | 45.5 | 61.0 | 429 |
| MJ0515 | 1013710 | 1014735 | formate hydrogenlyase, subunit 5 {*Escherichia coli*} | 31.0 | 51.1 | 1026 |
| MJ1027 | 514001 | 512871 | formate hydrogenlyase, subunit 5 {*Escherichia coli*} | 34.3 | 53.3 | 1131 |
| MJ1363 | 159614 | 160018 | formate hydrogenlyase, subunit 7 {*Escherichia coli*} | 38.4 | 60.9 | 405 |
| MJ0516 | 1013157 | 1013600 | formate hydrogenlyase, subunit 7 {*Escherichia coli*} | 48.8 | 65.6 | 444 |
| MJ0318 | 1175065 | 1175823 | formylmethanofuran:tetrahydromethanopterin formyltransferase {*Methanobacterium thermoautotrophicum*} | 68.6 | 84.5 | 759 |
| MJ1338 | 185930 | 185007 | H(2)-dependent methylenetetrahydromethanopterin dehydrogenase related protein {*Methanobacterium thermoautotrophicum*} | 29.1 | 50.5 | 924 |
| MJ0715 | 823334 | 822423 | H2-forming N5,N10-methylene-tetrahydromethanopterin dehydrogenase-related protein {*Methanococcus voltae*} | 29.9 | 52.5 | 912 |
| MJ0784 | 765279 | 764272 | H2-forming N5,N10-methylene-tetrahydromethanopterin dehydrogenease {*Methanococcus voltae*} | 73.6 | 85.5 | 1008 |
| MJ1190 | 342199 | 341003 | heterodisulfide reductase, subunit A {*Methanobacterium thermoautotrophicum*} | 58.0 | 75.2 | 1197 |
| MJ0743 | 801736 | 802422 | heterodisulfide reductase, subunit B {*Methandbacterium thermoautotrophicum*} | 59.3 | 79.0 | 687 |
| MJ0863 | 684944 | 685798 | heterodisulfide reductase, subunit B {*Methanobacterium thermoautotrophicum*} | 63.2 | 80.2 | 855 |
| MJ0744 | 801103 | 801489 | heterodisulfide reductase, subunit C {*Methanobacterium thermoautotrophicum*} | 53.4 | 68.4 | 387 |
| MJ0864 | 684283 | 684840 | heterodisulfide reductase, subunit C {*Methanobacterium thermoautotrophicum*} | 52.6 | 69.9 | 558 |
| MJ0118 | 1357167 | 1356667 | methyl coenzyme M reductase II operon, protein D {*Methanothermus fervidus*} | 53.2 | 77.5 | 501 |
| MJ0083 | 1395319 | 1393880 | methyl coenzyme M reductase II, alpha subunit {*Methanothermus fervidus*} | 89.8 | 95.5 | 1440 |
| MJ0081 | 1397700 | 1396351 | methyl coenzyme M reductase II, beta subunit {*Methanothermus fervidus*} | 79.7 | 89.4 | 1350 |
| MJ0082 | 1396335 | 1395538 | methyl coenzyme M reductase II, gamma subunit {*Methanothermus fervidus*} | 83.0 | 92.1 | 798 |
| MJ0844 | 702037 | 701465 | methyl coenzyme M reductase operon, protein C {*Methanococcus vannielii*} | 82.5 | 92.6 | 573 |
| MJ0843 | 702395 | 702069 | methyl coenzyme M reductase operon, protein D {*Methanococcus voltae*} | 58.0 | 81.4 | 327 |
| MJ1662 | 1491537 | 1493201 | methyl coenzyme M reductase system, component A2 {*Methanobacterium thermoauotrophicum*} | 37.1 | 60.1 | 1665 |
| MJ1242 | 284878 | 286338 | methyl coenzyme M reductase system, component A2 {*Methanobacterium thermoautotrophicum*} | 60.9 | 77.8 | 1461 |
| MJ0846 | 700322 | 698880 | methyl coenzyme M reductase, alpha subunit {*Methanococcus voltae*} | 86.1 | 92.1 | 1443 |
| MJ0842 | 703907 | 702576 | methyl coenzyme M reductase, beta subunit {*Methanococcus vannielii*} | 75.3 | 87.4 | 1332 |
| MJ0845 | 701389 | 700673 | methyl coenzyme M reductase, gamma subunit {*Methanococcus vannielii*} | 78.7 | 91.3 | 717 |
| MJ1636 | 1520054 | 1519128 | N5,N10-methenyl-tetrahydromethanopterin cyclohydrolase {*Methanobacterium thermdautotrophicum*} | 69.6 | 82.3 | 927 |
| MJ1534 | 1625526 | 1624534 | N5,N10-methylene tetrahydromethanopterin reductase {*Methanobacterium thermoautotrophicum*} | 66.2 | 79.7 | 993 |
| MJ0850 | 696203 | 695895 | N5-methyl-tetrahydromethanopterin:coenzyme M methyltransferase {*Methanobacterium thermoautotrophicum*} | 36.6 | 59.8 | 309 |
| MJ0849 | 696884 | 696216 | N5-methyl-tetrahydromethanopterin:coenzyme M methyltransferase {*Methanobacterium thermoautotrophicum*} | 41.8 | 62.3 | 669 |
| MJ0852 | 695117 | 694914 | N5-methyl-tetrahydromethanopterin:coenzyme M methyltransferase {*Methanobacterium thermoautotrophicum*} | 37.1 | 64.6 | 204 |
| MJ0851 | 695866 | 695138 | N5-methyl-tetrahydromethanopterin:coenzyme M methyltransferase {*Methanobacterium thermoautotrophicum*} | 55.2 | 73.5 | 729 |
| MJ0847 | 698519 | 697749 | N5-methyl-tetrahydromethanopterin:coenzyme M methyltransferase {*Methanobacterium thermoautotrophicum*} | 58.3 | 76.4 | 771 |
| MJ0854 | 694607 | 693651 | N5-methyl-tetrahydromethanopterin:coenzyme M methyltransferase {*Methanobacterium thermoautotrophicum*} | 62.1 | 77.5 | 957 |
| MJ0848 | 697696 | 697043 | N5-methyl-tetrahydromethanopterin:coenzyme M methyltransferase {*Methanobacterium thermoautotrophicum*} | 63.5 | 77.8 | 654 |
| MJ0853 | 694857 | 694639 | N5-methyl-tetrahydromethanopterin:coenzyme M methyltransferase G {*Methanobacterium thermoautotrophicum*} | 51.1 | 76.6 | 219 |
| MJ1169 | 363822 | 362122 | tungsten formylmethanofuran dehydrogenase, subunit A {*Methanobacterium thermoautotrophicum*} | 69.4 | 81.5 | 1701 |
| MJ1194 | 336096 | 335260 | tungsten formylmethanofuran dehydrogenase, subunit B {*Methanobacterium thermoautotrophicum*} | 71.1 | 84.0 | 837 |
| MJ1171 | 361740 | 360973 | tungsten formylmethanofuran dehydrogenase, subunit C {*Methanobacterium thermoautotrophicum*} | 52.7 | 67.7 | 768 |
| MJ0658 | 887575 | 886886 | tungsten formylmethanofuran dehydrogenase, subunit C related protein {*Methanobacterium thermoautotrophicum*} | 35.4 | 53.4 | 690 |

TABLE 1A-continued

| | | | | | | |
|---|---|---|---|---|---|---|
| MJ1168 | 364202 | 363852 | tungsten formylmethanofuran dehydrogenase, subunit D {*Methanobacterium thermoautotrophicum*} | 55.2 | 74.8 | 351 |
| MJ1165 | 366038 | 365637 | tungsten formylmethanofuran dehydrogenase, subunit E {*Methanobacterium thermoautotrophicum*} | 38.3 | 61.1 | 402 |
| MJ1166 | 365484 | 364567 | tungsten formylmethanofuran dehydrogenase, subunit F {*Methanobacterium thermoautotrophicum*} | 47.6 | 67.4 | 918 |
| MJ1167 | 364516 | 364271 | tungsten formylmethanofuran dehydrogenase, subunit G {*Methanobacterium thermoautotrophicum*} | 43.1 | 58.5 | 246 |
| Fatty acid and phospholipid metabolism | | | | | | |
| MJ0705 | 840072 | 838927 | 3-hydroxy-3-methylglutaryl coenzyme A reductase {*Haloferax volcanii*} | 49.8 | 67.3 | 1146 |
| MJ1546 | 1612371 | 1611697 | acyl carrier protein synthase {*Pyrococcus furiosus*} | 63.1 | 78.0 | 675 |
| MJ0860 | 688696 | 689499 | bifunctional short chain isoprenyl diphosphate synthase {*Methanobacterium thermoautotrophicum*} | 49.5 | 71.7 | 804 |
| MJ1229 | 299478 | 300644 | biotin carboxylase {Anabaena sp} | 58.9 | 76.2 | 1167 |
| MJ1212 | 316229 | 316786 | CDP-diacylglycerol-serine O-phosphatidyltransferase {*Bacillus subtilis*} | 45.5 | 63.7 | 558 |
| MJ1504 | 1661217 | 1662188 | lipopolysaccharide biosynthesis protein (bp1D) {*Bordetella pertussis*} | 44.3 | 63.1 | 972 |
| MJ1087 | 446091 | 445231 | melvalonate kinase {*Schizosaccharomyces pombe*} | 31.5 | 53.7 | 861 |
| MJ1549 | 1610772 | 1609735 | nonspecific lipid-transfer protein {*Pyrococcus furiosus*} | 46.9 | 66.0 | 1038 |
| Purines, pyrimidines, nucleosides, and nucleotides | | | | | | |
| 2'-Deoxyribonucleotide metabolism | | | | | | |
| MJ0832 | 719820 | 714604 | anaerobic ribonucleoside-triphosphate reductase {*Escherichia coli*} | 28.1 | 49.9 | 5217 |
| MJ0430 | 1085497 | 1086009 | deoxycytidine triphosphate deaminase {*Desulfurolobus ambivalens*} | 40.4 | 61.5 | 513 |
| MJ1102 | 429115 | 428648 | deoxycytidine triphosphate deaminase, putative {*Desulfurolobus ambivalens*} | 32.1 | 53.2 | 468 |
| MJ0511 | 1019410 | 1020075 | deoxyuridylate hydroxymethylase {*Methanobacterium thermoautotrophicum*} | 39.4 | 59.6 | 666 |
| MJ0937 | 606252 | 604921 | glycinamide ribonucleotide synthetase {*Homo sapiens*} | 37.1 | 55.0 | 1332 |
| Purine ribonucleotide biosynthesis | | | | | | |
| MJ0929 | 613484 | 612135 | adenylosuccinate lyase {*Bacillus subtilis*} | 42.6 | 67.4 | 1350 |
| MJ0561 | 976592 | 975741 | adenylosuccinate synthetase {*Haemophilus influenzae*} | 41.0 | 59.1 | 852 |
| MJ1575 | 1586386 | 1585823 | GMP synthetase {*Borrelia burgdorferi*} | 41.4 | 66.7 | 564 |
| MJ1131 | 399509 | 400264 | GMP synthetase {*Haemophilus influenzae*} | 52.0 | 72.3 | 756 |
| MJ1616 | 1545605 | 1544271 | inosine-5-monophosphate dehydrogenase {*Pyrococcus furiosus*} | 61.8 | 80.4 | 1335 |
| MJ1265 | 262116 | 262436 | nucleoside diphosphate kinase {*Haemophilus influenzae*} | 51.5 | 68.3 | 321 |
| MJ0616 | 925486 | 925941 | phosphoribosylaminoimidazole carboxylase {*Methanobrevibacter smithii*} | 56.3 | 76.2 | 456 |
| MJ1592 | 1572482 | 1572009 | phosphoribosylaminoimidazolesuccinocarboxamide synthase {*Bacillus subtilis*} | 51.0 | 69.1 | 474 |
| MJ0203 | 1277597 | 1276734 | phosphoribosylformylglycinamidine cyclo-ligase {*Bacillus subtilis*} | 42.7 | 64.4 | 864 |
| MJ1648 | 1507541 | 1507071 | phosphoribosylformylglycinamidine synthase I {*Bacillus subtilis*} | 52.9 | 71.5 | 471 |
| MJ1264 | 262585 | 264714 | phosphoribosylformylglycinamidine synthase II {*Bacillus subtilis*} | 43.3 | 65.1 | 2130 |
| MJ1486 | 13611 | 14633 | phosphoribosylglycinamide formyltransferase 2 {*Bacillus subtilis*} | 61.8 | 75.9 | 1023 |
| MJ1366 | 155580 | 156431 | ribose-phosphate pyrophosphokinase {*Haemophilus influenzae*} | 34.1 | 55.5 | 852 |
| Pyrimidine ribonucleotide biosynthesis | | | | | | |
| MJ1581 | 1581578 | 1580661 | aspartate carbamoyltransferase catalytic chain {*Escherichia coli*} | 50.0 | 70.7 | 918 |
| MJ1406 | 104548 | 104183 | aspartate carbamoyltransferase regulatory chain {*Escherichia coli*} | 39.1 | 65.1 | 366 |
| MJ1378 | 145461 | 144037 | carbamoyl-phosphate synthase, large chain {*Bacillus subtilis*} | 59.7 | 80.0 | 1425 |
| MJ1381 | 143097 | 141328 | carbamoyl-phosphate synthase, pyrimidine-specific, large subunit {*Bacillus caldolyticus*} | 54.7 | 75.7 | 1770 |
| MJ1019 | 523003 | 522041 | carbamoyl-phosphate synthase, small chain {*Bacillus subtilis*} | 49.6 | 69.1 | 963 |
| MJ1174 | 358774 | 360279 | CTP synthase {*Haemophilus influenzae*} | 56.7 | 74.0 | 1506 |
| MJ0656 | 888785 | 888306 | cytidylate kinase {*Bacillus subtilis*} | 31.9 | 59.5 | 480 |
| MJ1490 | 8032 | 6764 | dihydroorotase {*Bacillus caldolyticus*} | 34.5 | 56.3 | 1269 |
| MJ0654 | 889442 | 890284 | dihydroorotase dehydrogenase {*Bacillus subtilis*} | 43.1 | 66.6 | 843 |
| MJ0293 | 1196756 | 1196196 | thymidylate kinase {*Schizosaccharomyces pombe*} | 31.2 | 58.7 | 561 |
| MJ1109 | 421875 | 421348 | uridine 5'-monophosphate synthase {*Dictyostelium discoideum*} | 38.4 | 64.6 | 528 |
| MJ1259 | 271220 | 270543 | uridylate kinase {*Haemophilus influenzae*} | 27.5 | 48.7 | 678 |
| Salvage of nucleosides and nucleotides | | | | | | |
| MJ1459 | 43987 | 42413 | adenine deaminase {*Bacillus subtilis*} | 35.9 | 61.7 | 1575 |
| MJ1655 | 1499440 | 1499075 | adenine phosphoribosyltransferase {*Haemophilus influenzae*} | 35.8 | 62.5 | 366 |
| MJ0060 | 1412894 | 1412139 | methylthioadenosine phosphorylase {*Homo sapiens*} | 41.3 | 63.2 | 756 |
| MJ0667 | 879550 | 878150 | thymidine phosphorylase {*Mycoplasma genitalium*} | 30.5 | 52.2 | 1401 |
| Sugar-nucleotide biosynthesis and conversions | | | | | | |
| MJ1101 | 430386 | 429235 | glucose-1-phosphate thymidylyltransferase {*Streptomyces griseus*} | 32.0 | 56.0 | 1152 |
| MJ1334 | 188314 | 189084 | UDP-glucose pyrophosphorylase {*Mycoplasma genitalium*} | 42.7 | 63.6 | 771 |
| Regulatory functions | | | | | | |
| MJ0800 | 748410 | 747352 | activator of (R)-2-hydroxyglutaryl-CoA dehydratase {*Acidaminococcus fermentans*} | 31.8 | 51.2 | 1059 |
| MJ0004 | 1466944 | 1466255 | activator of (R)-2-hydroxyglutaryl-CoA dehydratase {*Acidaminococcus fermentans*} | 39.0 | 61.1 | 690 |
| MJ1344 | 180975 | 181229 | nitrogen regulatory protein P-II {*Haemophilus influenzae*} | 56.5 | 73.0 | 255 |

TABLE 1A-continued

| | | | | | | |
|---|---|---|---|---|---|---|
| MJ0059 | 1413301 | 1413047 | nitrogen regulatory protein P-II {*Haemophilus influenzae*} | 56.5 | 75.3 | 255 |
| MJ0300 | 1188832 | 1188194 | putative transcriptional regulator {*Bacillus subtilis*} | 27.8 | 50.3 | 639 |
| MJ0151 | 1325766 | 1325323 | putative transcriptional regulator {*Pyrococcus furiosus*} | 51.0 | 65.0 | 444 |
| MJ0723 | 815573 | 815190 | putative transcriptional regulator {*Pyrococcus furiosus*} | 51.2 | 82.3 | 384 |

Replication

Degradation of DNA

| | | | | | | |
|---|---|---|---|---|---|---|
| MJ1434 | 68536 | 68048 | endonuclease III {*Bacillus subtilis*} | 28.7 | 58.1 | 489 |
| MJ0613 | 927393 | 928424 | endonuclease III {*Bacillus subtilis*} | 41.3 | 66.3 | 1032 |
| MJ1439 | 65786 | 65208 | thermonuclease precursor {*Staphylococcus hyicus*} | 36.8 | 64.1 | 579 |

DNA replication, restriction, modification, recombination, and repair

| | | | | | | |
|---|---|---|---|---|---|---|
| MJ1029 | 510633 | 509875 | dimethyladenosine transferase {*Bacillus subtilis*} | 38.4 | 58.8 | 759 |
| MJ0104 | 1373055 | 1371130 | DNA helicase, putative {*Homo sapiens*} | 35.2 | 56.7 | 1926 |
| MJ0171 | 1297428 | 1299053 | DNA ligase {*Desulfurolobus ambivalens*} | 35.8 | 62.4 | 1626 |
| MJ0869 | 680404 | 679445 | DNA repair protein {*Saccharomyces cerevisiae*} | 44.6 | 62.2 | 960 |
| MJ1444 | 58945 | 58052 | DNA repair protein RAD2 {*Homo sapiens*} | 37.3 | 63.5 | 894 |
| MJ0254 | 1232179 | 1231757 | DNA repair protein RAD51 {*Homo sapiens*} | 32.5 | 58.4 | 423 |
| MJ0961 | 579580 | 577424 | DNA replication initiator protein {*Xenopus laevis*} | 28.1 | 40.0 | 2157 |
| MJ1652 | 1503610 | 1501559 | DNA topoisomerase I {*Mycoplasma genitalium*} | 34.0 | 55.0 | 2052 |
| MJ0885 | 656470 | 660960 | DNA-dependent DNA polymerase family B {Pyrococcus sp.} | 47.3 | 68.0 | 4491 |
| MJ1529 | 1630880 | 1630413 | methylated DNA protein cysteine methyltransferase {*Haemophilus influenzae*} | 35.9 | 66.4 | 468 |
| MJ1498 | 1548 | 715 | modification methylase {*Haemophilus parainfluenzae*} | 31.6 | 52.2 | 834 |
| MJ0598 | 942522 | 941860 | modification methylase {*Haemophilus influenzae*} | 32.4 | 53.8 | 663 |
| MJ1328 | 193775 | 192987 | modification methylase {*Haemophilus influenzae*} | 31.1 | 56.1 | 789 |
| MJ0563 | 974521 | 975309 | modification methylase {*Methanobacterium thermoformicicum*} | 34.7 | 56.2 | 789 |
| MJ1200 | 326214 | 327248 | modification methylase {*Desulfovibrio desulfuricans*} | 39.7 | 56.7 | 1035 |
| MJ0985 | 555045 | 555896 | modification methylase {*Methanobacterium thermoformicicum*} | 54.5 | 73.0 | 852 |
| MJ1149 | 383742 | 384248 | mutator mutT protein {*Escherichia coli*} | 40.3 | 63.9 | 507 |
| MJ0942 | 600802 | 598916 | probable ATP dependent helicase {*Haemophilus influenzae*} | 31.9 | 54.7 | 1887 |
| MJ0247 | 1237945 | 1237322 | proliferating-cell nuclear antigen {*Saccharomyces cerevisiae*} | 31.5 | 54.3 | 624 |
| MJ0026 | 1444598 | 1445224 | proliferating-cell nucleolar antigen, 120 kDa {*Homo sapiens*} | 48.1 | 66.1 | 627 |
| MJ1422 | 79304 | 84727 | replication factor C {*Homo sapiens*} | 45.2 | 64.6 | 5424 |
| MJ0884 | 662042 | 660969 | replication factor C, large subunit {*Homo sapiens*} | 32.5 | 49.2 | 1074 |
| MJ1220 | 308420 | 310102 | restriction modification enzyme, subunit M1 {*Mycoplasma pulmonis*} | 32.9 | 54.4 | 1683 |
| MJ0132 | 1345009 | 1345548 | restriction modification enzyme, subunit M1 {*Mycoplasma pulmonis*} | 37.3 | 61.1 | 540 |
| MJ0130 | 1346511 | 1347179 | restriction modification system S subunit {*Spiroplasma citri*} | 29.3 | 59.2 | 669 |
| MJ1512 | 1653580 | 1648742 | reverse gyrase {*Sulfolobus acidocaldarius*} | 41.8 | 62.4 | 4839 |
| MJ0135 | 1341301 | 1341939 | ribonuclease HII (rnhB) {*Escherichia coli*} | 45.2 | 64.6 | 639 |
| MJECL42 | 55944 | 54271 | type I restriction enyzme ECOR124/3 I M protein {*Haemophilus influenzae*} | 39.7 | 61.4 | 1673 |
| MJ0124 | 1349371 | 1352847 | type I restriction enzyme {*Haemophilus influenzae*} | 31.1 | 52.2 | 3477 |
| MJ1214 | 313714 | 315828 | type I restriction enzyme {*Haemophilus influenzae*} | 29.5 | 52.2 | 2115 |
| MJECL40 | 52581 | 49456 | type I restriction enzyme {*Haemophilus influenzae*} | 36.2 | 59.9 | 3125 |
| MJ1531 | 1629137 | 1628493 | type I restriction enzyme CfrI, specificity subunit {*Citrobacter freundii*} | 38.4 | 57.9 | 645 |
| MJ1218 | 310547 | 311776 | type I restriction-modification enzyme, S subunit {*Escherichia coli*} | 29.7 | 49.7 | 1230 |
| MJ0984 | 556397 | 555909 | type II restriction enzyme {*Methanobacterium thermoformicicum*} | 45.9 | 67.2 | 489 |
| MJ0600 | 940932 | 940315 | type II restriction enzyme DPNII {*Streptococcus pneumoniae*} | 46.0 | 67.4 | 618 |

Transcription

DNA-dependent RNA polymerases

| | | | | | | |
|---|---|---|---|---|---|---|
| MJ1042 | 497715 | 493732 | DNA-dependent RNA polymerase, subunit A' {*Methanococcus vannielii*} | 74.5 | 88.1 | 3984 |
| MJ1043 | 493546 | 491078 | DNA-dependent RNA polymerase, subunit A" {*Methanococcus vannielii*} | 66.7 | 83.5 | 2469 |
| MJ1041 | 499305 | 497866 | DNA-dependent RNA polymerase, subunit B' {*Methanococcus vannielii*} | 76.3 | 91.3 | 1440 |
| MJ1040 | 501124 | 499862 | DNA-dependent RNA polymerase, subunit B" {*Methanococcus vannielii*} | 72.7 | 87.4 | 1263 |
| MJ0192 | 1283621 | 1283148 | DNA-dependent RNA polymerase, subunit D {*Arabidopsis thaliana*} | 39.5 | 58.6 | 474 |
| MJ0397 | 1113901 | 1114371 | DNA-dependent RNA polymerase, subunit E' {*Sulfolobus acidocaldarius*} | 47.9 | 70.8 | 471 |
| MJ0396 | 1114384 | 1114560 | DNA-dependent RNA polymerase, subunit E" {*Sulfolobus acidocaldarius*} | 35.9 | 62.3 | 177 |
| MJ1039 | 501599 | 501366 | DNA-dependent RNA polymerase, subunit H {*Methanococcus vannielii*} | 49.4 | 78.7 | 234 |
| MJ1390 | 134111 | 134350 | DNA-dependent RNA polymerase, subunit I {*Sulfolobus acidocaldarius*} | -0.9 | -0.9 | 240 |
| MJ0197 | 1281417 | 1281247 | DNA-dependent RNA polymerase, subunit K {*Haloarcula marismortui*} | 43.5 | 65.3 | 171 |
| MJ0387 | 1119216 | 1119512 | DNA-dependent PNA polymerase, subunit L {*Sulfolobus acidocaldarius*} | 35.6 | 63.4 | 297 |
| MJ0196 | 1281779 | 1281561 | DNA-dependent RNA polymerase, subunit N {*Haloarcula marismortui*} | 53.8 | 83.4 | 219 |

Transcription factors

| | | | | | | |
|---|---|---|---|---|---|---|
| MJ0941 | 601867 | 600923 | putative transcription initiation factor IIIC {*Saccharomyces cerevisiae*} | 20.1 | 44.1 | 945 |
| MJ1045 | 490363 | 489848 | putative transcription termination-antitermination factor nusA {*Methanococcus vannielii*} | 47.9 | 73.7 | 516 |
| MJ0372 | 1134509 | 1134123 | putative transcription termination-antitermination factor nusG {*Homo sapiens*} | 38.6 | 63.8 | 387 |
| MJ0507 | 1024170 | 1024631 | TATA-binding transcription initiation factor {*Thermococcus celer*} | 51.4 | 74.0 | 462 |
| MJ0782 | 766586 | 768592 | transcription initiation factor IIB {*Pyrococcus woesei*} | 63.8 | 77.6 | 2007 |
| MJ1148 | 384277 | 384567 | transcription-associated protein, ('TFIIS') {*Thermococcus celer*} | 56.4 | 69.0 | 291 |

RNA processing

| | | | | | | |
|---|---|---|---|---|---|---|
| MJ0697 | 849814 | 849125 | fibrillarin-like pre-rRNA processing protein {*Methanococcus vannielii*} | 75.3 | 88.3 | 690 |

TABLE 1A-continued

Translation

| | | | | | | |
|---|---|---|---|---|---|---|
| MJ0160 | 1308036 | 1309265 | PET112 protein {*Saccharomyces cerevisiae*} | 32.3 | 53.7 | 1230 |

Amino acyl tRNA synthetases

| | | | | | | |
|---|---|---|---|---|---|---|
| MJ0564 | 971657 | 974149 | alanyl-tRNA synthetase (alaRS) {*Haemophilus influenzae*} | 28.0 | 53.1 | 2493 |
| MJ0237 | 1244137 | 1242641 | arginyl-tRNA synthetase {*Mycobacterium leprae*} | 31.3 | 52.7 | 1497 |
| MJ1555 | 1605935 | 1604679 | aspartyl-tRNA synthetase {*Pyrococcus sp.*} | 57.8 | 75.6 | 1257 |
| MJ1377 | 145796 | 147325 | glutamyl-tRNA synthetase {*Methanobacterium thermoautotrophicum*} | 51.7 | 73.6 | 1530 |
| MJ0228 | 1253254 | 1251524 | glycyl tRNA synthetase {*Schizosaccharomyces pombe*} | 45.8 | 65.2 | 1731 |
| MJ1000 | 543634 | 542396 | histidyl-tRNA synthetase {*Streptococcus equisimilis*} | 35.5 | 56.3 | 1239 |
| MJ0947 | 591914 | 594817 | isoleucyl-tRNA synthetase {*Methanobacterium thermoautotrophicum*} | 52.1 | 70.0 | 2904 |
| MJ0633 | 912642 | 910015 | leucyl-tRNA synthetase {*Saccharomyces cerevisiae*} | 34.4 | 54.9 | 2628 |
| MJ1263 | 266697 | 264745 | methionyl-tRNA synthetase {*Haemophilus influenzae*} | 35.6 | 56.0 | 1953 |
| MJ0487 | 1041343 | 1039994 | phenylalanyl-tRNA synthetase, subunit alpha {*Saccharomyces cerevisiae*} | 41.0 | 64.0 | 1350 |
| MJ1108 | 423555 | 425198 | phenylalanyl-tRNA synthetase, subunit beta {*Saccharomyces cerevisiae*} | 31.6 | 55.4 | 1644 |
| MJ1238 | 287985 | 289172 | prolyl-tRNA synthetase {*Homo sapiens*} | 39.3 | 59.5 | 1188 |
| MJ1197 | 332116 | 330257 | threonyl-tRNA synthetase {*Synechocystis sp.*} | 29.1 | 52.1 | 1860 |
| MJ1415 | 96418 | 95369 | tryptophanyl-tRNA synthetase {*Schizosaccharomyces pombe*} | 30.5 | 55.3 | 1050 |
| MJ0389 | 1118380 | 1117616 | tyrosyl-tRNA synthetase {*Homo sapiens*} | 39.9 | 63.7 | 765 |
| MJ1007 | 536642 | 534186 | valyl-tRNA synthetase {*Bacillus stearothermophilus*} | 36.1 | 56.6 | 2457 |

Degradation of proteins, peptides, and glycopeptides

| | | | | | | |
|---|---|---|---|---|---|---|
| MJ1176 | 356300 | 357370 | ATP-dependent 26S protease regulatory subunit 4 {*Homo sapiens*} | 51.0 | 74.1 | 1071 |
| MJ1494 | 4302 | 5123 | ATP-dependent 26S protease regulatory subunit 8 {*Methanobacterium thermoautotrophicum*} | 58.6 | 78.2 | 822 |
| MJ1417 | 93716 | 91932 | ATP-dependent protease La {*Bacillus brevis*} | 32.8 | 54.3 | 1785 |
| MJ0090 | 1387867 | 1386755 | collagenase {*Porphyromonas gingivalis*} | 32.6 | 35.2 | 1113 |
| MJ1130 | 400455 | 401969 | O-sialoglycoprotein endopeptidase {*Saccharomyces cerevisiae*} | 50.6 | 67.9 | 1515 |
| MJ0651 | 891988 | 892842 | protease IV {*Haemophilus influenzae*} | 35.0 | 56.2 | 855 |
| MJ0591 | 947601 | 946861 | proteasome, subunit alpha {*Methanosarcina thermophila*} | 57.5 | 78.8 | 741 |
| MJ1237 | 289440 | 289967 | proteasome, subunit beta {*Methanosarcina thermophila*} | 47.5 | 68.2 | 528 |
| MJ0806 | 742381 | 743364 | xaa-pro dipeptidase {*Lactobacillus delbrueckii*} | 36.1 | 65.2 | 984 |
| MJ0996 | 547987 | 546635 | Zn protease {*Haemophilus influenzae*} | 33.9 | 55.0 | 1353 |

Protein modification

| | | | | | | |
|---|---|---|---|---|---|---|
| MJ0814 | 733804 | 734793 | deoxyhypusine synthase {*Homo sapiens*} | 50.0 | 70.7 | 990 |
| MJ1274 | 253925 | 254653 | diphthine synthase {*Saccharomyces cerevisiae*} | 40.7 | 61.5 | 729 |
| MJ0172 | 1296723 | 1297175 | L-isoaspartyl protein carboxyl methyltransferase {*Escherichia coli*} | 47.6 | 59.4 | 453 |
| MJ1329 | 192979 | 192098 | methionine aminopeptidase {*Saccharomyces cerevisiae*} | 36.2 | 55.1 | 882 |
| MJ1530 | 1630123 | 1629764 | N-terminal acetyltransferase complex, subunit ARD1 {*Homo sapiens*} | 39.7 | 55.7 | 360 |
| MJ1591 | 1573833 | 1573072 | selenium donor protein {*Homo sapiens*} | 34.3 | 57.1 | 762 |

Ribosomal proteins: synthesis and modification

| | | | | | | |
|---|---|---|---|---|---|---|
| MJ0509 | 1022576 | 1023502 | acidic ribosomal protein P0 (L10E) {*Methanococcus vannielii*} | 63.2 | 82.1 | 927 |
| MJ0242 | 1240163 | 1240228 | ribosomal protein HG12 {*Catus (cat)*} | 63.7 | 81.9 | 66 |
| MJ1203 | 325110 | 325460 | ribosomal protein HS6-type {*Haloarcula marismortui*} | 47.0 | 71.4 | 351 |
| MJ0510 | 1021912 | 1022460 | ribosomal protein L1 {*Methanococcus vannielii*} | 64.5 | 80.3 | 549 |
| MJ0373 | 1133926 | 1133540 | ribosomal protein L11 {*Sulfolobus solfataricus*} | 47.2 | 72.4 | 387 |
| MJ0508 | 1023632 | 1023937 | ribosomal protein L12 {*Methanococcus vannielii*} | 72.8 | 80.9 | 306 |
| MJ0194 | 1282568 | 1282260 | ribosomal protein L13 {*Haloarcula marismortui*} | 44.9 | 66.4 | 309 |
| MJ0466 | 1058694 | 1058452 | ribosomal protein L14 {*Methanococcus vannielii*} | 78.8 | 92.5 | 243 |
| MJ0657 | 888216 | 887977 | ribosomal protein L14B {*Saccharomyces cerevisiae*} | 36.4 | 59.8 | 240 |
| MJ0477 | 1052625 | 1052302 | ribosomal protein L15 {*Methanococcus vannielii*} | 62.7 | 79.5 | 324 |
| MJ0983 | 556982 | 557290 | ribosomal protein L15B {*Thermoplasma acidophilum*} | 62.3 | 78.6 | 309 |
| MJ0474 | 1054523 | 1053939 | ribosomal protein L18 {*Methanococcus vannielii*} | 73.3 | 84.3 | 585 |
| MJ0473 | 1054978 | 1054559 | ribosomal protein L19 {*Methanococcus vannielii*} | 67.0 | 86.4 | 420 |
| MJ0179 | 1291786 | 1291052 | ribosomal protein L2 {*Methanococcus vannielii*} | 74.0 | 87.0 | 735 |
| MJ0040 | 1431958 | 1432260 | ribosomal protein L21 {*Haloarcula marismortui*} | 54.5 | 62.3 | 303 |
| MJ0460 | 1061493 | 1061089 | ribosomal protein L22 {*Haloarcula marismortui*} | 40.7 | 61.7 | 405 |
| MJ0178 | 1292097 | 1291840 | ribosomal protein L23 {*Methanococcus vannielii*} | 69.8 | 91.9 | 258 |
| MJ0467 | 1058340 | 1058062 | ribosomal protein L24 {*Methanococcus vannielii*} | 70.5 | 83.0 | 279 |
| MJ1201 | 325929 | 326078 | ribosomal protein L24E {*Haloarcula marismortui*} | 54.6 | 66.7 | 150 |
| MJ0462 | 1060388 | 1060212 | ribosomal protein L29 {*Halobacterium halobium*} | 51.0 | 69.9 | 177 |
| MJ0193 | 1283076 | 1282705 | ribosomal protein L29E {*Haloarcula marismortui*} | 48.7 | 68.7 | 372 |
| MJ0176 | 1293794 | 1292934 | ribosomal protein L3 {*Haloarcula marismortui*} | 45.2 | 63.9 | 861 |
| MJ1044 | 490704 | 490399 | ribosomal protein L30 {*Methanococcus vannielii*} | 63.9 | 84.1 | 306 |
| MJ0049 | 1421907 | 1422152 | ribosomal protein L31{*Nicotiana glutinosa*} | 40.9 | 66.2 | 246 |
| MJ0472 | 1055464 | 1055063 | ribosomal protein L32 {*Methanococcus vannielii*} | 58.0 | 77.4 | 402 |
| MJ0655 | 889197 | 888931 | ribosomal protein L34 {*Aedes albopictus*} | 36.8 | 58.3 | 267 |
| MJ0098 | 1380525 | 1380686 | ribosomal protein L37 {*Leishmania infantum,*} | 50.0 | 67.4 | 162 |
| MJ0593 | 945958 | 945683 | ribosomal protein L37a {*Homo sapiens*} | 44.6 | 58.7 | 276 |
| MJ0177 | 1292889 | 1292134 | ribosomal protein L4 (human) {*Haloarcula marismortui*} | 49.4 | 66.3 | 756 |
| MJ0707 | 838122 | 838229 | ribosomal protein L40 {*Saccharomyces cerevisiae*} | 57.6 | 66.7 | 108 |
| MJ0249 | 1236729 | 1236448 | ribosomal protein L44 {*Haloarcula marismortui*} | 38.8 | 58.1 | 282 |
| MJ0689 | 854995 | 855150 | ribosomal protein L46 {*Sulfolobus solfataricus,*} | 52.0 | 70.0 | 156 |
| MJ0469 | 1057259 | 1056723 | ribosomal protein L5 {*Methanococcus vannielii*} | 72.5 | 84.5 | 537 |
| MJ0471 | 1056071 | 1055526 | ribosomal protein L6 {*Methanococcus vannielii*} | 66.5 | 82.5 | 546 |
| MJ0476 | 1053137 | 1052745 | ribosomal protein L7 {*Methanococcus vannielii*} | 70.3 | 88.6 | 393 |

TABLE 1A-continued

| | | | | | | | |
|---|---|---|---|---|---|---|---|
| MJ0595 | 944670 | 944473 | ribosomal protein LX {*Sulfolobus acidocaldarius*} | | 38.9 | 66.7 | 198 |
| MJ0322 | 1172916 | 1173218 | ribosomal protein S10 {*Pyrococcus woesei*} | | 67.0 | 91.0 | 303 |
| MJ0191 | 1283956 | 1283735 | ribosomal protein S11 {*Haloarcula marismortui*} | | 67.2 | 80.0 | 222 |
| MJ1046 | 489559 | 489260 | ribosomal protein S12 {*Methanococcus vannielii*} | | 87.0 | 96.0 | 300 |
| MJ0036 | 1434801 | 1434352 | ribosomal protein S13 {*Brugia pahangi*,} | | 49.4 | 71.0 | 450 |
| MJ1474 | 26554 | 26054 | ribosomal protein S15A {*Brassica napus*} | | 21.7 | 48.2 | 501 |
| MJ0465 | 1059233 | 1058883 | ribosomal protein S17 {*Methanococcus vannielii*} | | 71.6 | 82.4 | 351 |
| MJ0245 | 1238750 | 1238896 | ribosomal protein S17B {*Saccharomyces cerevisiae*} | | 55.4 | 80.9 | 147 |
| MJ0189 | 1285220 | 1284771 | ribosomal protein S18 {*Arabidopsis thaliana*} | | 42.3 | 68.5 | 450 |
| MJ0180 | 1290861 | 1290508 | ribosomal protein S19 {*Haloarcula marismortui*} | | 56.9 | 73.3 | 354 |
| MJ0692 | 853669 | 854046 | ribosomal protein S19S {*Ascaris suum*} | | 49.6 | 67.0 | 378 |
| MJ0394 | 1115064 | 1115366 | ribosomal protein S24 {*Haloarcula marismortui*} | | 42.6 | 64.4 | 303 |
| MJ0250 | 1236377 | 1236192 | ribosomal protein S27 {*Saccharomyces cerevisiae*} | | 42.6 | 53.8 | 186 |
| MJ0393 | 1115369 | 1115548 | ribosomal protein S27A {*Caenorhabditis elegans*} | | 58.4 | 68.8 | 180 |
| MJ0461 | 1061060 | 1060437 | ribosomal protein S3 {*Haloarcula marismortui*} | | 49.1 | 72.1 | 624 |
| MJ1202 | 325575 | 325808 | ribosomal protein S33 {*Kluyveromyces lactis*} | | 62.1 | 81.1 | 234 |
| MJ0980 | 558761 | 559252 | ribosomal protein S3a {*Catharanthus roseus*} | | 29.8 | 52.1 | 492 |
| MJ0190 | 1284710 | 1284150 | ribosomal protein S4 {*Sulfolobus acidocaldarius*} | | 51.3 | 68.4 | 561 |
| MJ0468 | 1057935 | 1057318 | ribosomal protein S4E {*Methanococcus vannielii*} | | 70.9 | 84.5 | 618 |
| MJ0475 | 1053877 | 1053275 | ribosomal protein S5 {*Methanococcus vannielii*} | | 75.7 | 88.6 | 603 |
| MJ1260 | 270075 | 269683 | ribosomal protein S6 {*Homo sapiens*} | | 36.2 | 58.0 | 393 |
| MJ0620 | 922671 | 921799 | ribosomal protein S6 modification protein {*Haemophilus influenzae*} | | 34.4 | 57.3 | 873 |
| MJ1001 | 542227 | 541487 | ribosomal protein S6 modification protein II {*Haemophilus influenzae*} | | 24.8 | 47.4 | 741 |
| MJ1047 | 489046 | 488627 | ribosomal protein S7 {*Methanococcus vannielii*} | | 65.8 | 83.6 | 420 |
| MJ0470 | 1056445 | 1056113 | ribosomal protein S8 {*Methanococcus vannielii*} | | 71.2 | 89.2 | 333 |
| MJ0673 | 873106 | 872720 | ribosomal protein S8E {*Haloarcula marismortui*} | | 50.0 | 69.7 | 387 |
| MJ0195 | 1282118 | 1281840 | ribosomal protein S9 {*Haloarcula marismortui*} | | 50.0 | 75.0 | 279 |
| tRNA modification | | | | | | | |
| MJ0946 | 595006 | 596040 | N2,N2-dimethylguanosine tRNA methyltransferase {*Saccharomyces cerevisiae*} | | 31.6 | 56.0 | 1035 |
| MJ1675 | 1478684 | 1477755 | pseudouridylate synthase I {*Haemophilus influenzae*} | | 33.5 | 57.2 | 930 |
| MJ0436 | 1081116 | 1082732 | queuine tRNA ribosyltransferase {*Escherichia coli*} | | 30.4 | 47.6 | 1617 |
| Translation factors | | | | | | | |
| MJ0829 | 723534 | 722260 | peptide chain release factor, eRF, subunit 1 {*Xenopus laevis*} | | 33.0 | 57.3 | 1275 |
| MJ1505 | 1659133 | 1661085 | putative ATP-dependent RNA helicase, eIF-4A family {*Saccharomyces cerevisiae*} | | 30.8 | 51.9 | 1953 |
| MJ1574 | 1587062 | 1588927 | putative ATP-dependent RNA helicase, eIF-4A family {*Bacillus subtilis*} | | 33.1 | 56.0 | 1866 |
| MJ0669 | 876636 | 877637 | putative ATP-dependent RNA helicase, eIF-4A family {*Bacillus subtilis*} | | 44.5 | 65.8 | 1002 |
| MJ0495 | 1035432 | 1034644 | putative translation factor, EF-TU/1 alpha family {*Thermus aquaticus*} | | 36.9 | 55.9 | 1389 |
| MJ0262 | 1225060 | 1221653 | putative translation initiation factor, FUN12/bIF-2 family {*Saccharomyces cerevisiae*} | | 39.3 | 61.5 | 3408 |
| MJ0324 | 1171724 | 1172830 | translation elongation factor, EF-1 alpha {*Methanococcus vannielii*} | | 78.9 | 90.8 | 1107 |
| MJ1048 | 488471 | 486336 | translation elongation factor, EF-2 {*Methanococcus vannielii*} | | 74.8 | 88.5 | 2136 |
| MJ0445 | 1073262 | 1073483 | translation initiation factor, eIF-1A {*Thermoplasma acidophilum*} | | 52.8 | 70.3 | 222 |
| MJ0117 | 1357516 | 1358196 | translation initiation factor, eIF-2, subunit alpha {*Saccharomyces cerevisiae*} | | 32.2 | 56.5 | 681 |
| MJ0097 | 1380885 | 1381313 | translation initiation factor, eIF-2, subunit beta {*Drosophila melanogaster*} | | 32.1 | 60.4 | 429 |
| MJ1261 | 269396 | 268164 | translation initiation factor, eIF-2, subunit gamma {*Homo sapiens*} | | 52.6 | 71.9 | 1233 |
| MJ0454 | 1066217 | 1067065 | translation initiation factor, eIF-2B, subunit alpha {*Saccharomyces cerevisiae*} | | 37.9 | 56.4 | 849 |
| MJ0122 | 1353264 | 1354127 | translation initiation factor, eIP-2B, subunit delta {*Mus musculus*} | | 29.4 | 54.6 | 864 |
| MJ1228 | 300895 | 301236 | translation initiation factor, eIF-5a {*Sulfolobus acidocaldarius*} | | 50.0 | 69.7 | 342 |
| Transport and binding proteins | | | | | | | |
| MJ0719 | 818577 | 820289 | ABC transporter ATP-binding protein {*Saccharomyces cerevisiae*} | | 49.6 | 66.9 | 1713 |
| MJ1023 | 518606 | 517821 | ABC transporter ATP-binding protein {*Bacillus firmus*} | | 49.2 | 72.4 | 786 |
| MJ1572 | 1590114 | 1589518 | ABC transporter ATP-binding protein {*Mycoplasma genitalium*} | | 50.0 | 87.5 | 597 |
| MJ0035 | 1435236 | 1435829 | ABC transporter subunit {*Cyanelle Cyanophora*} | | 33.9 | 58.1 | 594 |
| MJ1508 | 1656015 | 1655446 | ABC transporter, probable ATP-binding subunit {*Haemophilus influenzae*} | | 45.7 | 68.3 | 570 |
| MJ1332 | 189987 | 191117 | GTP-binding protein {*Saccharomyces cerevisiae*} | | 38.7 | 59.8 | 1131 |
| MJ1326 | 196392 | 195292 | GTP-binding protein {*Schizosaccharomyces pombe*} | | 51.4 | 71.5 | 1101 |
| MJ1408 | 103449 | 102430 | GTP-binding protein, GTP1/OBG-family {*Saccharomyces cerevisiae*} | | 30.5 | 58.4 | 1020 |
| MJ1464 | 39865 | 38858 | hypothetical GTP-binding protein (SP:P40010) {*Saccharomyces cerevisiae*} | | 32.0 | 55.5 | 1008 |
| MJ1033 | 507274 | 506324 | magnesium and cobalt transport protein {*Haemophilus influenzae*} | | 42.2 | 57.9 | 951 |
| MJ0091 | 1386551 | 1385751 | Na+/Ca+ exchanger protein {*Escherichia coli*} | | 32.3 | 58.6 | 801 |
| MJ0283 | 1204330 | 1203563 | nucleotide-binding protein {*Homo sapiens*} | | 47.5 | 68.0 | 768 |
| Amino acids; peptides and amines | | | | | | | |
| MJ0609 | 933328 | 934587 | amino acid transporter {*Arabidopsis thaliana*} | | 21.9 | 48.7 | 1260 |
| MJ1343 | 181359 | 182519 | ammonium transport protein AMT1 {*Arabidopsis thaliana*} | | 35.6 | 53.3 | 1161 |
| MJ0058 | 1413598 | 1414770 | ammonium transporter {*Escherichia coli*} | | 34.2 | 52.2 | 1173 |
| MJ1269 | 258901 | 257993 | branched-chain amino acid transport protein livH {*Escherichia coli*} | | 30.8 | 54.6 | 909 |
| MJ1266 | 261404 | 260577 | branched-chain amino acid transport protein livJ {*Escherichia coli*} | | 28.8 | 55.2 | 828 |
| MJ1270 | 257896 | 256934 | branched-chain amino acid transport protein livM {*Escherichia coli*} | | 28.7 | 52.2 | 963 |
| MJ1196 | 332430 | 333311 | cationic amino acid transporter MCAT-2 {*Mus musculus*} | | 24.6 | 50.6 | 882 |
| MJ0304 | 1185908 | 1186333 | ferripyochelin binding protein {*Pseudomonas aeruginosa*} | | 55.6 | 74.7 | 426 |
| MJ0796 | 752786 | 752118 | glutamine transport ATP-binding protein Q {*Escherichia coli*} | | 47.9 | 67.2 | 669 |
| MJ1267 | 260465 | 259707 | high-affinity branched-chain amino acid transport ATP-binding protein {*Pseudomonas aeruginosa*} | | 34.2 | 60.8 | 759 |

TABLE 1A-continued

| MJ1268 | 259458 | 258973 | high-affinity branched-chain amino acid transport ATP-binding protein {Salmonella typhimurium} | 40.4 | 68.6 | 486 |
|---|---|---|---|---|---|---|
| Anions | | | | | | |
| MJ0412 | 1099862 | 1100608 | nitrate transport ATP-binding protein {Synechococcus sp} | 44.6 | 70.1 | 747 |
| MJ0413 | 1099077 | 1099826 | nitrate transport perinease protein {Synechococcus sp} | 34.2 | 59.4 | 750 |
| MJ1012 | 529685 | 530431 | phosphate transport system ATP-binding protein {Escherichia coli} | 60.9 | 80.7 | 747 |
| MJ1013 | 528941 | 529642 | phosphate transport system permease protein A {Haemophilus influenzae} | 39.6 | 60.5 | 702 |
| MJ1014 | 528397 | 528810 | phosphate transport system permease prdtein C {Haemophilus influenzae} | 40.0 | 66.5 | 414 |
| MJ1009 | 532458 | 533165 | phosphate transport system regulatory protein {Escherichia coli} | 28.5 | 54.6 | 708 |
| MJ1015 | 526871 | 527698 | phosphate-binding protein {Xanthomonas oryzae} | 45.8 | 60.2 | 828 |
| Carbohydrates, organic alcohols, and acids | | | | | | |
| MJ0576 | 960439 | 959399 | malic acid transport protein {Schizosaccharomyces pombe} | 23.8 | 47.9 | 1041 |
| MJ0762 | 786703 | 787524 | malic acid transport protein {Schizosaccharomyces pombe} | 26.5 | 49.3 | 822 |
| MJ0121 | 1354728 | 1355291 | SN-glycerol-3-phosphate transport ATP-binding protein {Escherichia coli} | 33.4 | 51.7 | 564 |
| MJ1319 | 206861 | 205926 | sodium-dependent noradrenaline transporter {Haemophilus influenzae} | 37.8 | 61.0 | 936 |
| Cations | | | | | | |
| MJ1088 | 444480 | 445223 | cobalt transport ATP-binding protein O {Salmonella typhimurium} | 46.1 | 66.6 | 744 |
| MJ1090 | 443372 | 443527 | cobalt transport protein N {Salmonella typhimurium} | 59.1 | 79.6 | 156 |
| MJ1089 | 443778 | 444374 | cobalt transport protein Q {Salmonella typhimurium} | 28.9 | 55.6 | 597 |
| MJ0089 | 1388820 | 1388059 | ferric enterobactin transport ATP-binding protein {Escherichia coli} | 33.1 | 59.6 | 762 |
| MJ0873 | 674824 | 674123 | ferric enterobactin transport ATP-binding protein {Escherichia coli} | 31.5 | 60.3 | 702 |
| MJ0566 | 967842 | 969857 | ferrous iron transport protein B {Escherichia coli} | 35.8 | 61.2 | 2016 |
| MJ0877 | 670239 | 670442 | hemin permease {Haemophilus influenzae} | 27.9 | 62.3 | 204 |
| MJ0087 | 1390284 | 1389385 | hemin permease {Yersinia enterocolitica} | 40.6 | 67.7 | 900 |
| MJ0085 | 1392668 | 1391613 | iron tranport system binding protein {Bacillus subtilis} | 32.9 | 53.3 | 1056 |
| MJ0876 | 670677 | 671498 | iron(III) dicitrate transport system permease protein {Escherichia coli} | 30.8 | 52.8 | 822 |
| MJ1441 | 64080 | 60403 | magnesium chelatase subunit {Arabidopsis thaliana} | 35.3 | 57.3 | 3678 |
| MJ0911 | 628932 | 629972 | magnesium-chelatase subunit {Euglena gracilis} | 54.9 | 73.4 | 1041 |
| MJ1275 | 253661 | 252597 | NA(+)/H(+) antiporter {Enterococcus hirae} | 29.8 | 59.9 | 1065 |
| MJ0672 | 873748 | 874665 | Na$^+$ transporter {Haemophilus influenzae} | 39.3 | 63.1 | 918 |
| MJ1231 | 297233 | 298873 | oxaloacetate decarboxylase, alpha subunit {Salmonella typhimurium} | 52.0 | 68.7 | 1641 |
| MJ1357 | 164247 | 165065 | putative potassium channel protein {Bacillus cereus} | 42.9 | 66.7 | 819 |
| MJ1367 | 154669 | 155559 | sulfate permease (cysA) {Synechococcus sp} | 38.5 | 64.5 | 891 |
| MJ1368 | 153995 | 154666 | sulfate/thiosulfate transport protein {Escherichia coli} | 30.9 | 59.4 | 672 |
| MJ1485 | 16909 | 15713 | TRK system potassium uptake protein {Escherichia coli} | 29.5 | 58.5 | 1197 |
| MJ1105 | 426702 | 427217 | TRK system potassium uptake protein A {Methanosarcina mazei} | 39.3 | 57.6 | 516 |
| Other | | | | | | |
| MJ1142 | 390844 | 389885 | arsenical pump-driving ATPase {Escherichia coli} | 34.7 | 55.9 | 960 |
| MJ0822 | 727897 | 729522 | ATPase, vanadate-senstive {Methanococcus voltae} | 48.1 | 69.0 | 1626 |
| MJ0718 | 820399 | 821523 | chromate resistance protein A {Alcaligenes eutrophus} | 27.9 | 52.4 | 1125 |
| MJ1226 | 304219 | 301988 | H$^+$-transporting ATPase {Arabidopsis thaliana} | 45.1 | 63.7 | 2232 |
| MJ1560 | 1600958 | 1601974 | quinolone resistance norA protein protein {Staphylococcus aureus} | 28.8 | 51.1 | 1017 |
| Other-categories | | | | | | |
| MJ1365 | 157333 | 156458 | pheromone shutdown protein {Enterococcus faecalis} | 31.2 | 57.2 | 876 |
| MJECL24 | 28069 | 28845 | SOJ protein {Bacillus subtilis} | 34.0 | 62.1 | 776 |
| Drug and analog sensitivity | | | | | | |
| MJ1538 | 1621434 | 1620691 | K. lactis toxin sensitivity protein KTI12 {Saccharomyces cerevisiae} | 28.4 | 48.8 | 744 |
| MJ0102 | 1375563 | 1375859 | phenylacrylic acid decarboxylase {Saccharomyces cerevisiae} | 50.0 | 74.0 | 297 |
| Phage-related functions and prophages | | | | | | |
| MJ0630 | 915023 | 914598 | sodium-dependent phosphate transporter {Cricetulus griseus} | 32.6 | 60.8 | 426 |

TABLE 1A-continued

Transposon-related functions

| | | | | | | |
|---|---|---|---|---|---|---|
| MJ0367 | 1138754 | 1138080 | integrase {*Weeksella zoohelcum*} | 30.9 | 54.4 | 675 |
| MJ0017 | 1455555 | 1454946 | transposase {*Bacillus thuringiensis*} | 29.5 | 55.0 | 610 |

Other

| | | | | | | |
|---|---|---|---|---|---|---|
| MJ1064 | 466505 | 467095 | acetyltransferase {*Escherichia coli*} | 47.0 | 62.4 | 591 |
| MJ1612 | 1549430 | 1548297 | BcpC phosphonopyruvate decarboxylase {*Streptomyces hygroscopicus*} | 31.1 | 48.9 | 1134 |
| MJ0677 | 868213 | 869160 | ethylene-inducible protein homolog {*Hevea brasiliensis*} | 68.3 | 81.0 | 948 |
| MJ0534 | 1003199 | 1002072 | flavoprotein {*Methanobacterium thermoautotrophicum*} | 34.6 | 57.2 | 1128 |
| MJ0748 | 797504 | 798673 | flavoprotein {*Methanobacterium thermoautotrophicum*} | 67.0 | 82.6 | 1170 |
| MJ0256 | 1230191 | 1229760 | fom2 phosphonopyruvate decarboxylase {*Streptomyces wedmorensis*} | 36.7 | 58.5 | 432 |
| MJ1682 | 1472535 | 1473320 | heat shock protein X {*Haemophilus influenzae*} | 30.4 | 55.5 | 786 |
| MJ0866 | 682753 | 682367 | HIT protein, member of the HIT-family {*Saccharomyces cerevisiae*} | 39.4 | 64.8 | 387 |
| MJ0294 | 1193529 | 1195817 | large helicase related protein, LHR {*Escherichia coli*} | 31.4 | 53.6 | 2289 |
| MJ0010 | 1460660 | 1459497 | phosphonopyruvate decarboxylase {*Streptomyces hygroscopicus*} | 28.0 | 47.2 | 1164 |
| MJ0734 | 805855 | 806439 | rubrerythrin {*Clostridium perfringens*} | 48.9 | 69.2 | 585 |
| MJ0559 | 978287 | 977490 | surE survival protein {*Escherichia coli*} | 34.7 | 55.6 | 798 |
| MJ1100 | 431754 | 430489 | urease operon protein {*Mycobacterium leprae*} | 33.2 | 55.0 | 1266 |
| MJ0543 | 990687 | 991100 | Wilm's tumor suppressor homolog {*Arabidopsis thaliana*} | 45.6 | 64.9 | 414 |
| MJ0765 | 784011 | 785549 | [6Fe-65] prismane-containing protein {*Desulfovibrio desulfuricans*} | 60.2 | 72.8 | 1539 |

Hypothetical

| | | | | | | |
|---|---|---|---|---|---|---|
| MJ0458 | 1063165 | 1062518 | hypothetical protein {*Sulfolobus acidocaldarius*} | -0.9 | -0.9 | 648 |
| MJ0483 | 1047280 | 1048250 | hypothetical protein {*Saccharomyces cerevisiae*} | 27.7 | 48.7 | 971 |
| MJ0920 | 620866 | 621357 | hypothetical protein {*Mycoplasma genitalium*} | 28.3 | 51.3 | 492 |
| MJ0443 | 1074680 | 1075348 | hypothetical protein {*Saccharomyces cerevisiae*} | 27.8 | 52.8 | 669 |
| MJ0144 | 1330246 | 1330962 | hypothetical protein {*Methanobacterium thermoautotrophicum*} | 33.4 | 58.6 | 717 |
| MJ0044 | 1426552 | 1427241 | hypothetical protein (GP:D38561_6) {*Streptomyces wedmorensis*} | 24.1 | 49.8 | 690 |
| MJ0868 | 680710 | 681000 | hypothetical protein (GP:D63999_31) {*Synechocystis sp.*} | 42.2 | 65.0 | 291 |
| MJ1502 | 1662923 | 1663714 | hypothetical protein (GP:D64001_24) {*Synechocystis sp.*} | 36.4 | 60.1 | 792 |
| MJ1129 | 402152 | 402382 | hypothetical protein (GP:D64001_53) {*Synechocystis sp.*} | 37.5 | 57.9 | 231 |
| MJ0057 | 1414899 | 1416176 | hypothetical protein (GP:D64003_36) {*Synechocystis sp.*} | 28.4 | 53.2 | 1278 |
| MJ1335 | 187757 | 187593 | hypothetical protein (GP:D64004_11) {*Synechocystis sp.*} | 46.2 | 63.5 | 165 |
| MJ0640 | 902502 | 903458 | hypothetical protein (GP:D64005_53) {*Synechocystis sp.*} | 33.9 | 58.8 | 957 |
| MJ1347 | 177726 | 177280 | hypothetical protein (GP:D64006_36) {*Synechocystis sp.*} | 32.1 | 58.6 | 447 |
| MJ0392 | 1116428 | 1115556 | hypothetical protein (GP:D64006_95) {*Synechocystis sp.*} | 29.1 | 54.3 | 873 |
| MJ0590 | 950234 | 948222 | hypothetical protein (GP:D64044_18) {*Escherichia coli*} | 30.6 | 52.6 | 2013 |
| MJ1178 | 355642 | 355956 | hypothetical protein (GP:L47709_14) {*Bacillus subtilis*} | 27.1 | 55.3 | 315 |
| MJ0438 | 1080099 | 1079128 | hypothetical protein (GP:L47838_15) {*Bacillus subtilis*} | 29.6 | 55.8 | 972 |
| MJ0644 | 898810 | 898223 | hypothetical protein (GP:M18279_1) {*Pseudomonas sp.*} | 28.3 | 53.4 | 588 |
| MJ0828 | 723763 | 723668 | hypothetical protein (GP:M35130_5) {M71467 M71468} | 58.1 | 87.1 | 96 |
| MJ1526 | 1632280 | 1632810 | hypothetical protein (GP:M36534_1) {*Methanobrevibacter smithii*} | 42.6 | 66.5 | 531 |
| MJ0888 | 652964 | 653473 | hypothetical protein (GP:U00011_3) {*Mycobacterium leprae*} | 29.5 | 51.4 | 510 |
| MJ0729 | 809665 | 809321 | hypothetical protein (GP:U18744_1) {*Bacillus firmus*} | 29.4 | 56.9 | 345 |
| MJ0787 | 761402 | 760077 | hypothetical protein (GP:U19363_11) {*Methanobacterium thermoautotrophicum*} | 49.9 | 71.9 | 1326 |
| MJ0693 | 852445 | 853059 | hypothetical protein (GP:U19363_2) {*Methanobacterium thermoautotrophicum*} | 42.8 | 61.9 | 615 |
| MJ0489 | 1039414 | 1038686 | hypothetical protein (GP:U19363_4) {*Methanobacterium thermoautotrophicum*} | 41.3 | 57.5 | 729 |
| MJ0446 | 1072662 | 1071784 | hypothetical protein (GP:U19363_5) {*Methanobacterium thermoautotrophicum*} | 29.8 | 50.7 | 879 |
| MJ0076 | 1400741 | 1400403 | hypothetical protein (GP:U19364_10) {*Methanobacterium thermoautotrophicum*} | 25.3 | 56.1 | 339 |
| MJ0034 | 1435995 | 1436921 | hypothetical protein (GP:UI9364_2) {*Methanobacterium thermoautotrophicum*} | 23.9 | 49.7 | 927 |
| MJ1251 | 277892 | 277392 | hypothetical protein (GP:UI9364_4) {*Methanobacterium thermoautotrophicum*} | 37.8 | 61.0 | 501 |
| MJ0927 | 615224 | 615694 | hypothetical protein (GP:U19364_6) {*Methanobacterium thermoautotrophicum*} | 37.9 | 57.2 | 471 |
| MJ0785 | 763999 | 762923 | hypothetical protein (GP:U19364_8) {*Methanobacterium thermoautotrophicum*} | 57.5 | 76.6 | 1077 |
| MJ0746 | 799630 | 799935 | hypothetical protein (GP:U21086_2) {*Methanobacterium thermoautotrophicum*} | 60.3 | 76.4 | 306 |
| MJ1155 | 378926 | 380485 | hypothetical protein (GP:W28377_114) {*Escherichia coli*} | 40.0 | 63.7 | 1560 |
| MJ0653 | 890904 | 890359 | hypothetical protein (GP:U31567_2) {*Methanopyrus kandleri*} | 42.2 | 64.8 | 546 |
| MJ0532 | 1003608 | 1004750 | hypothetical protein (GP:U32666_1) {*Methanosarcina barkeri*} | 39.3 | 59.5 | 1143 |
| MJ0674 | 872153 | 871623 | hypothetical protein (GP:X83963_2) {*Thermococcus litoralis*} | 58.3 | 76.7 | 531 |
| MJ1552 | 1608984 | 1608592 | hypothetical protein (GP:X85250_3) {*Pyrococcus furiosus*} | 48.5 | 68.0 | 393 |
| MJ0709 | 837195 | 835996 | hypothetical protein (GP:X91006_2) {*Pyrococcus sp.*} | 25.1 | 50.5 | 1200 |
| MJ0226 | 1255943 | 1255389 | hypothetical protein (GP:Z49569_1) {*Saccharomyces cerevisiae*} | 39.0 | 60.6 | 555 |
| MJ1476 | 25468 | 24851 | hypothetical protein (HI0380) {*Haemophilus influenzae*} | 39.7 | 62.6 | 618 |
| MJ0441 | 1076859 | 1076125 | hypothetical protein (HI0902) {*Haemophilus influenzae*} | 29.2 | 51.1 | 735 |
| MJ1372 | 151434 | 150760 | hypothetical protein (HI0920) {*Haemophilus influenzae*} | 46.7 | 67.5 | 675 |
| MJ0931 | 611416 | 610298 | hypothetical protein (MG372) {*Mycoplasma genitalium*} | 34.9 | 59.9 | 1119 |
| MJ0861 | 687240 | 688532 | hypothetical protein (MG423) {*Mycoplasma genitalium*} | 33.9 | 53.9 | 1293 |
| MJ1252 | 277977 | 278609 | hypothetical protein (PIR:B48653) {*Lactococcus lactis*} | 32.5 | 47.2 | 633 |
| MJ0279 | 1206983 | 1206147 | hypothetical protein (PIR:S01072) {*Desulfurococcus mobilis*} | 29.2 | 53.4 | 837 |
| MJ0299 | 1189620 | 1190600 | hypothetical protein (PIR:S11602) {*Thermoplasma acidophilum*} | 62.1 | 76.6 | 981 |
| MJ1208 | 320842 | 319766 | hypothetical protein (PIR:S21569) {*Metbanobacterium thermoautotrophicum*} | 55.4 | 74.8 | 1077 |
| MJ1533 | 1625982 | 1627727 | hypothetical protein (PIR:S28724) {*Methanococcus vannielii*} | 67.3 | 83.3 | 1746 |
| MJ0323 | 1172727 | 1172276 | hypothetical protein (PIR:S38467) {*Desulfurococcus mobilis*} | 60.7 | 71.7 | 471 |
| MJ1162 | 368773 | 369060 | hypothetical protein (PIR:S41581) {*Methanothermus fervidus*} | 48.3 | 67.7 | 288 |
| MJ0922 | 619284 | 619598 | hypothetical protein (PIR:S41583) {*Methanothermus fervidus*} | 48.6 | 73.4 | 315 |
| MJ0867 | 681124 | 682371 | hypothetical protein (PIR:S49379) {*Pseudomonas aeruginosa*} | 28.7 | 55.2 | 1248 |
| MJ0047 | 1423924 | 1424988 | hypothetical protein (PIR:S51413) {*Saccharomyces cerevisiae*} | 26.9 | 49.9 | 1065 |

TABLE 1A-continued

| | | | | | | | |
|---|---|---|---|---|---|---|---|
| MJ1236 | 290570 | 292111 | hypothetical protein (PIR:S51413) {Saccharomyces cerevisiae} | 33.9 | 54.6 | 1542 |
| MJ0162 | 1306782 | 1305562 | hypothetical protein (PIR:S51413) {Saccharomyces cerevisiae} | 32.4 | 56.4 | 1221 |
| MJ0928 | 614493 | 614957 | hypothetical protein (PIR:S51868) {Saccharomyces cerevisiae} | 38.4 | 61.7 | 465 |
| MJ1625 | 1535098 | 1533113 | hypothetical protein (PIR:S52522) {Saccharomyces cerevisiae} | 27.6 | 50.4 | 1986 |
| MJ0862 | 686185 | 687054 | hypothetical protein (PIR:S52979) {Erwinia herbicola} | 35.5 | 59.2 | 870 |
| MJ1432 | 69872 | 69453 | hypothetical protein (PIR:S53543) {Saccharomyces cerevisiae} | 38.5 | 66.0 | 420 |
| MJ0710 | 835912 | 834914 | hypothetical protein (SP:P05409) {Methanococcus thermolithotrophicus} | 59.2 | 79.9 | 999 |
| MJ0170 | 1299322 | 1300185 | hypothetical protein (SP:P11666) {Escherichia coli} | 30.1 | 54.8 | 864 |
| MJ1593 | 1571988 | 1571740 | hypothetical protein (SP:P12049) {Bacillus subtilis} | 40.3 | 69.6 | 249 |
| MJ0463 | 1060127 | 1059819 | hypothetical protein (SP:P14021) {Methanococcus vannielii} | 78.5 | 92.2 | 309 |
| MJ0464 | 1059719 | 1059435 | hypothetical protein (SP:P14022) {Methanococcus vannielii} | 58.8 | 79.4 | 285 |
| MJ0136 | 1340892 | 1340105 | hypothetical protein (SP:P14027) {Methanococcus vannielii} | 63.4 | 87.8 | 788 |
| MJ0388 | 1118696 | 1119244 | hypothetical protein (SP:P15886) {Methanococcus vannielii} | 46.9 | 66.3 | 549 |
| MJ1225 | 305183 | 304425 | hypothetical protein (SP:P15889) {Thermofilum pendens} | 24.1 | 53.9 | 759 |
| MJ1133 | 398771 | 397509 | hypothetical protein (SP:P22349) {Methanobrevibacter smithii} | 45.9 | 67.4 | 1263 |
| MJ1273 | 255725 | 254676 | hypothetical protein (SP:P25125) {Thermus aquaticus} | 41.4 | 60.2 | 1050 |
| MJ1426 | 76255 | 75812 | hypothetical protein (SP:P25768) {Methanobacterium ivanovii} | 47.3 | 69.3 | 444 |
| MJ0549 | 986782 | 986360 | hypothetical protein (SP:P28910) {Escherichia coli} | 33.9 | 59.3 | 423 |
| MJ0982 | 557497 | 558078 | hypothetical protein (SP:P29202) {Haloarcula marismortui} | 55.9 | 75.4 | 582 |
| MJ0990 | 552446 | 552658 | hypothetical protein (SP:P31065) {Escherichia coli,} | 39.2 | 62.4 | 213 |
| MJ0326 | 1170026 | 1168809 | hypothetical protein (SP:P31466) {Escherichia coli} | 45.6 | 71.7 | 1218 |
| MJ0812 | 736053 | 736679 | hypothetical protein (SP:P31473) {Escherichia coli} | 25.8 | 54.3 | 627 |
| MJ0079 | 1398567 | 1399694 | hypothetical protein (SP:P31473) {Escherichia coli} | 38.0 | 63.3 | 1128 |
| MJ1586 | 1578018 | 1576645 | hypothetical protein (SP:P31806) {Escherichia coli} | 32.4 | 52.1 | 1434 |
| MJ1124 | 409920 | 406336 | hypothetical protein (SP:P32639) {Saccharomyces cerevisiae} {Saccharomyces cerevisiae} | 26.9 | 51.5 | 3585 |
| MJ1081 | 451124 | 450726 | hypothetical protein (SP:P32698) {Escherichia coli} | 38.2 | 62.8 | 399 |
| MJ1413 | 97390 | 97629 | hypothetical protein (SP:P33382) {Listeria monocytogenes} | 40.0 | 60.0 | 240 |
| MJ1170 | 362086 | 361820 | hypothetical protein (SP:P33382) {Listeria monocytogenes} | 42.2 | 63.9 | 267 |
| MJ0051 | 1419978 | 1419670 | hypothetical protein (SP:P34222) {Saccharomyces cerevisiae} | 38.5 | 55.8 | 309 |
| MJ1523 | 1636316 | 1635945 | hypothetical protein (SP:P37002) {Escherichia coli} | 43.0 | 65.0 | 372 |
| MJ0608 | 934974 | 935750 | hypothetical protein (SP:P37487) {Bacillus subtilis} | 44.3 | 71.4 | 777 |
| MJ1661 | 1493414 | 1493809 | hypothetical protein (SP:P37528) {Bacillus subtilis} | 47.0 | 72.6 | 396 |
| MJ1582 | 1580646 | 1579909 | hypothetical protein (SP:P37545) {Bacillus subtilis} | 35.4 | 60.6 | 738 |
| MJ1375 | 148221 | 149408 | hypothetical protein (SP:P37555) {Bacillus subtilis} | 25.0 | 48.6 | 1188 |
| MJ0231 | 1249786 | 1250814 | hypothetical protein (SP:P37869) {Bacillus subtilis} | 40.0 | 44.0 | 1029 |
| MJ0882 | 664582 | 663910 | hypothetical protein (SP:P37872) {Bacillus subtilis} | 44.0 | 68.7 | 673 |
| MJ0043 | 1429606 | 1427252 | hypothetical protein (SP:P38423) {Bacillus subtilis} {Bacillus subtilis} | 45.5 | 58.4 | 2355 |
| MJ0048 | 1422159 | 1422842 | hypothetical protein (SP:P38619) {Sulfolobus acidocaldarius} | 36.6 | 59.1 | 684 |
| MJ0989 | 552670 | 553011 | hypothetical protein (SP:P39164) {Escherichia coli} | 29.0 | 51.8 | 342 |
| MJ1115 | 415733 | 416479 | hypothetical protein (SP:P39364) {Eschenchia coli} | 27.1 | 48.3 | 747 |
| MJ1649 | 1506277 | 1507068 | hypothetical protein (SP:P39587) {Bacillus subtilis} | 28.9 | 48.5 | 792 |
| MJ0577 | 959388 | 958903 | hypothetical protein (SP:P42297) {Bacillus subtilis} | 31.6 | 56.4 | 486 |
| MJ0531 | 1004977 | 1004759 | hypothetical protein (SP:P42297) {Bacillus subtilis} | 43.3 | 68.7 | 219 |
| MJ1247 | 282030 | 281677 | hypothetical protein (SP:P42404) {Bacillus subtilis} | 38.4 | 60.0 | 354 |
| MJ0486 | 1041905 | 1042681 | hypothetical protein (SP:P45476) {Escherichia coli} | 30.6 | 55.7 | 777 |
| MJ0449 | 1070080 | 1069565 | hypothetical protein (SP:P46348) {Bacillus subtilis} | 31.8 | 60.7 | 516 |
| MJ0682 | 861537 | 864374 | hypothetical protein (SP:P46850) {Escherichia coli} | 33.4 | 53.9 | 2838 |
| MJ1677 | 1476726 | 1476376 | hypothetical protein (SP:P46851) {Escherichia coli} | 40.3 | 62.0 | 351 |
| MJ0588 | 951068 | 952243 | hypothetical protein GP:L07942_2 {Escherichia coli} | 31.1 | 55.0 | 1176 |
| MJ0225 | 1256840 | 1256121 | hypothetical protein GP:U00014_23 {Mycobacterium leprae} | 27.4 | 49.0 | 720 |
| MJ0134 | 1342043 | 1342792 | hypothetical protein GP:U00017_21{Mycobacterium leprae} | 32.2 | 52.7 | 750 |
| MJ0376 | 1130650 | 1129136 | hypothetical proiein GP:U29579_58 {Escherichia coli} | 30.1 | 51.5 | 1521 |
| MJ0028 | 1443023 | 1443844 | hypothetical protein HI1305 {Haemophilus influenzae} | 27.0 | 50.0 | 822 |
| MJ1136 | 395844 | 394486 | hypothetical protein Lpg22p (GP:U43281_22) {Saccharomyces cerevisiae} | 46.2 | 63.8 | 1359 |
| MJ0952 | 588063 | 588479 | hypothetical protein PIR:S49633 {Saccharomyces cerevisiae} | 26.8 | 55.0 | 417 |
| MJ0403 | 1109067 | 1108276 | hypothetical protein PIR:S55196 {Saccharomyces cerevisiae} | 27.6 | 48.2 | 792 |
| MJ1031 | 509420 | 508506 | hypothetical protein SP:P45869 {Bacillus subtilis} | 26.8 | 51.1 | 915 |

TABLE 1B

| | | | | | | |
|---|---|---|---|---|---|---|
| MJ0479 | 1,050,508 | 1,049,948 | adenylate kinase {Methanococcus jannaschii} | 100.0% | 100.0% | 585 |

TABLE 2

| | | |
|---|---|---|
| MJ0002 | 4071 | 3343 |
| MJ0003 | 4911 | 5378 |
| MJ0008 | 10075 | 10734 |
| MJ0009 | 10743 | 11570 |
| MJ0011 | 12983 | 13459 |
| MJ0012 | 13927 | 13427 |
| MJ0013 | 14836 | 14351 |
| MJ0014 | 15455 | 14820 |
| MJ0015 | 15514 | 15804 |
| MJ0016 | 16416 | 15866 |
| MJ0018 | 17658 | 19229 |
| MJ0019 | 21121 | 19232 |
| MJ0021 | 22762 | 23886 |
| MJ0023 | 25284 | 25637 |
| MJ0024 | 26105 | 25689 |
| MJ0025 | 27122 | 26109 |
| MJ0027 | 28572 | 28021 |
| MJ0037 | 38073 | 38786 |
| MJ0038 | 39443 | 38793 |
| MJ0039 | 39974 | 39654 |

TABLE 2-continued

| | | |
|---|---|---|
| MJ0041 | 41838 | 40477 |
| MJ0042 | 42527 | 41883 |
| MJ0045 | 46506 | 45907 |
| MJ0046 | 47351 | 46569 |
| MJ0050 | 52237 | 51050 |
| MJ0052 | 53374 | 52709 |
| MJ0053 | 54068 | 53388 |
| MJ0054 | 55001 | 54159 |
| MJ0056 | 56154 | 55759 |
| MJ0062 | 60618 | 61238 |
| MJ0063 | 61322 | 61855 |
| MJ0064 | 61897 | 62454 |
| MJ0065 | 63551 | 62463 |
| MJ0066 | 65078 | 63657 |
| MJ0067 | 65160 | 65468 |
| MJ0068 | 65861 | 65517 |
| MJ0070 | 66966 | 67211 |
| MJ0071 | 67211 | 67480 |
| MJ0072 | 67562 | 67693 |
| MJ0073 | 67729 | 68007 |
| MJ0074 | 69089 | 68016 |
| MJ0075 | 70324 | 69236 |
| MJ0077 | 71539 | 70394 |
| MJ0078 | 72674 | 72054 |
| MJ0080 | 74182 | 73802 |
| MJ0086 | 80788 | 81903 |
| MJ0088 | 83019 | 83537 |
| MJ0093 | 88517 | 88092 |
| MJ0094 | 89481 | 88564 |
| MJ0095 | 89828 | 89568 |
| MJ0096 | 90752 | 89967 |
| MJ0100 | 94823 | 93297 |
| MJ0103 | 97958 | 99256 |
| MJ0105 | 101649 | 101239 |
| MJ0106 | 102541 | 101840 |
| MJ0107 | 102733 | 104295 |
| MJ0109 | 106419 | 105664 |
| MJ0110 | 106880 | 106614 |
| MJ0114 | 111874 | 112782 |
| MJ0115 | 113249 | 112785 |
| MJ0116 | 113931 | 113257 |
| MJ0119 | 116397 | 115726 |
| MJ0120 | 117070 | 116372 |
| MJ0123 | 119524 | 119195 |
| MJ0125 | 123378 | 123031 |
| MJ0126 | 123685 | 123392 |
| MJ0127 | 124034 | 123672 |
| MJ0128 | 124341 | 124048 |
| MJ0129 | 124487 | 124996 |
| MJ0131 | 126783 | 126475 |
| MJ0133 | 129427 | 128609 |
| MJ0137 | 134976 | 134119 |
| MJ0138 | 136566 | 135121 |
| MJ0139 | 136616 | 138244 |
| MJ0140 | 139150 | 139539 |
| MJ0141 | 139529 | 139825 |
| MJ0142 | 139797 | 140237 |
| MJ0145 | 142991 | 142188 |
| MJ0146 | 143409 | 143203 |
| MJ0147 | 144813 | 143701 |
| MJ0149 | 146003 | 145830 |
| MJ0150 | 146069 | 146587 |
| MJ0154 | 152143 | 152589 |
| MJ0157 | 159807 | 160085 |
| MJ0158 | 160155 | 161276 |
| MJ0159 | 163046 | 161430 |
| MJ0163 | 167378 | 166818 |
| MJ0164 | 168614 | 167430 |
| MJ0165 | 169394 | 168627 |
| MJ0166 | 170194 | 169430 |
| MJ0173 | 175871 | 176341 |
| MJ0175 | 178089 | 177475 |
| MJ0181 | 182625 | 181918 |
| MJ0182 | 183311 | 182730 |
| MJ0183 | 183491 | 183348 |
| MJ0184 | 183606 | 183827 |
| MJ0185 | 183886 | 184032 |
| MJ0187 | 185874 | 185440 |
| MJ0188 | 186674 | 185880 |
| MJ0198 | 191384 | 192259 |
| MJ0201 | 193486 | 193007 |
| MJ0202 | 193687 | 194454 |
| MJ0206 | 198871 | 198467 |
| MJ0207 | 198967 | 199419 |
| MJ0208 | 200166 | 199429 |
| MJ0209 | 200956 | 200159 |
| MJ0212 | 203759 | 204019 |
| MJ0213 | 204137 | 204583 |
| MJ0215 | 205636 | 205190 |
| MJ0223 | 214474 | 214163 |
| MJ0224 | 215072 | 214566 |
| MJ0227 | 218176 | 219099 |
| MJ0229 | 221136 | 220852 |
| MJ0230 | 221386 | 221144 |
| MJ0233 | 224281 | 225111 |
| MJ0235 | 226124 | 226369 |
| MJ0236 | 226362 | 227639 |
| MJ0239 | 230506 | 230988 |
| MJ0240 | 231618 | 231094 |
| MJ0241 | 232062 | 231628 |
| MJ0243 | 232563 | 232318 |
| MJ0248 | 235142 | 235651 |
| MJ0251 | 238728 | 238288 |
| MJ0252 | 238849 | 239487 |
| MJ0255 | 241359 | 240607 |
| MJ0257 | 242764 | 243696 |
| MJ0258 | 245039 | 243840 |
| MJ0259 | 245717 | 245112 |
| MJ0261 | 247082 | 246423 |
| MJ0263 | 251686 | 250727 |
| MJ0270 | 256421 | 256188 |
| MJ0271 | 256902 | 257441 |
| MJ0272 | 257452 | 257649 |
| MJ0273 | 258107 | 258412 |
| MJ0274 | 260378 | 258819 |
| MJ0275 | 261121 | 260516 |
| MJ0280 | 266375 | 266758 |
| MJ0281 | 267291 | 266761 |
| MJ0282 | 267341 | 267787 |
| MJ0284 | 269902 | 269174 |
| MJ0286 | 270849 | 270499 |
| MJ0287 | 271160 | 270870 |
| MJ0288 | 271755 | 271222 |
| MJ0289 | 272805 | 271801 |
| MJ0290 | 273753 | 273121 |
| MJ0292 | 275409 | 275137 |
| MJ0296 | 279767 | 280360 |
| MJ0297 | 281155 | 280406 |
| MJ0298 | 281290 | 281739 |
| MJ0301 | 285101 | 284220 |
| MJ0303 | 285971 | 285558 |
| MJ0305 | 286594 | 287778 |
| MJ0306 | 287997 | 287818 |
| MJ0308 | 289084 | 288386 |
| MJ0310 | 290609 | 290268 |
| MJ0311 | 290981 | 290652 |
| MJ0312 | 291845 | 291228 |
| MJ0314 | 293767 | 294369 |
| MJ0315 | 294826 | 294455 |
| MJ0316 | 295458 | 294964 |
| MJ0317 | 296374 | 295733 |
| MJ0319 | 297675 | 297902 |
| MJ0320 | 298001 | 298645 |
| MJ0321 | 298675 | 299040 |
| MJ0325 | 302095 | 301172 |
| MJ0327 | 303625 | 303927 |
| MJ0328 | 304755 | 304318 |
| MJ0329 | 306607 | 304760 |
| MJ0330 | 308266 | 306620 |
| MJ0331 | 308670 | 308266 |
| MJ0332 | 308995 | 308678 |
| MJ0333 | 309670 | 309410 |
| MJ0334 | 309816 | 310112 |
| MJ0335 | 310179 | 310919 |
| MJ0336 | 310932 | 311288 |
| MJ0337 | 311299 | 312084 |
| MJ0338 | 312100 | 312402 |
| MJ0339 | 312374 | 312694 |

TABLE 2-continued

| | | |
|---|---|---|
| MJ0340 | 312697 | 313398 |
| MJ0341 | 313411 | 313770 |
| MJ0342 | 313918 | 314286 |
| MJ0343 | 314270 | 316807 |
| MJ0344 | 316820 | 317359 |
| MJ0345 | 317314 | 318264 |
| MJ0346 | 318277 | 318579 |
| MJ0347 | 318593 | 319045 |
| MJ0348 | 319620 | 321995 |
| MJ0349 | 322367 | 322053 |
| MJ0350 | 322681 | 322418 |
| MJ0351 | 323154 | 322705 |
| MJ0352 | 323901 | 323185 |
| MJ0353 | 324142 | 323891 |
| MJ0354 | 324296 | 324123 |
| MJ0355 | 324661 | 324374 |
| MJ0356 | 324957 | 324697 |
| MJ0357 | 326407 | 325943 |
| MJ0358 | 326796 | 326413 |
| MJ0359 | 327449 | 326808 |
| MJ0360 | 328174 | 327770 |
| MJ0361 | 329502 | 329182 |
| MJ0362 | 329659 | 329847 |
| MJ0364 | 332163 | 332495 |
| MJ0365 | 332503 | 333030 |
| MJ0366 | 333033 | 333308 |
| MJ0368 | 334581 | 334886 |
| MJ0369 | 336040 | 334934 |
| MJ0371 | 337418 | 337639 |
| MJ0374 | 339873 | 338884 |
| MJ0375 | 339920 | 340681 |
| MJ0377 | 343243 | 343752 |
| MJ0378 | 343921 | 344886 |
| MJ0379 | 345500 | 344889 |
| MJ0380 | 345657 | 345974 |
| MJ0381 | 345977 | 346936 |
| MJ0382 | 346955 | 347683 |
| MJ0383 | 347677 | 349518 |
| MJ0384 | 349546 | 350259 |
| MJ0385 | 350252 | 351304 |
| MJ0386 | 351648 | 351307 |
| MJ0390 | 355149 | 354760 |
| MJ0395 | 357787 | 357314 |
| MJ0398 | 359111 | 359923 |
| MJ0400 | 361593 | 362411 |
| MJ0401 | 362717 | 362520 |
| MJ0402 | 363046 | 362729 |
| MJ0404 | 364804 | 364355 |
| MJ0405 | 365385 | 365002 |
| MJ0408 | 367518 | 367880 |
| MJ0409 | 367946 | 370054 |
| MJ0410 | 370074 | 370865 |
| MJ0414 | 374603 | 373419 |
| MJ0415 | 374712 | 375197 |
| MJ0416 | 375222 | 375791 |
| MJ0417 | 376510 | 375800 |
| MJ0418 | 376627 | 377388 |
| MJ0419 | 377369 | 378430 |
| MJ0420 | 378394 | 379533 |
| MJ0421 | 379640 | 380719 |
| MJ0423 | 381855 | 382031 |
| MJ0424 | 382046 | 382336 |
| MJ0425 | 382317 | 382712 |
| MJ0426 | 383243 | 382704 |
| MJ0427 | 383719 | 383243 |
| MJ0431 | 387350 | 387135 |
| MJ0432 | 388127 | 387852 |
| MJ0433 | 388663 | 388139 |
| MJ0434 | 389342 | 388677 |
| MJ0435 | 389620 | 389342 |
| MJ0437 | 391903 | 391667 |
| MJ0439 | 394280 | 393234 |
| MJ0440 | 394492 | 395292 |
| MJ0444 | 398609 | 397740 |
| MJ0447 | 401037 | 400555 |
| MJ0448 | 401168 | 401935 |
| MJ0450 | 403277 | 403834 |
| MJ0452 | 404962 | 404519 |
| MJ0453 | 405287 | 404967 |
| MJ0455 | 406863 | 406285 |
| MJ0456 | 406888 | 407943 |
| MJ0459 | 410088 | 410354 |
| MJ0480 | 422470 | 423063 |
| MJ0481 | 423792 | 424085 |
| MJ0482 | 423793 | 423074 |
| MJ0485 | 427056 | 428102 |
| MJ0488 | 432390 | 432854 |
| MJ0491 | 434681 | 435106 |
| MJ0492 | 435385 | 435101 |
| MJ0494 | 436499 | 436891 |
| MJ0496 | 438482 | 438823 |
| MJ0497 | 439219 | 438821 |
| MJ0498 | 439679 | 439212 |
| MJ0500 | 442304 | 441537 |
| MJ0501 | 442990 | 442394 |
| MJ0504 | 445785 | 446372 |
| MJ0505 | 446365 | 447117 |
| MJ0512 | 453993 | 453292 |
| MJ0513 | 454868 | 454149 |
| MJ0517 | 459731 | 459321 |
| MJ0518 | 460018 | 459737 |
| MJ0519 | 460275 | 460033 |
| MJ0521 | 461746 | 461549 |
| MJ0522 | 462422 | 461769 |
| MJ0523 | 463226 | 462534 |
| MJ0524 | 463697 | 463239 |
| MJ0525 | 463997 | 463839 |
| MJ0526 | 464308 | 464123 |
| MJ0527 | 465146 | 464655 |
| MJ0528 | 465442 | 465149 |
| MJ0529 | 466215 | 465520 |
| MJ0538 | 474805 | 474026 |
| MJ0539 | 476422 | 474833 |
| MJ0540 | 476947 | 476693 |
| MJ0541 | 477507 | 476971 |
| MJ0545 | 483451 | 482711 |
| MJ0546 | 483623 | 483456 |
| MJ0548 | 485032 | 484589 |
| MJ0550 | 487106 | 486012 |
| MJ0551 | 487918 | 487106 |
| MJ0553 | 489383 | 488925 |
| MJ0554 | 490365 | 489910 |
| MJ0556 | 492396 | 491875 |
| MJ0557 | 493186 | 492572 |
| MJ0558 | 493984 | 493202 |
| MJ0560 | 495301 | 494891 |
| MJ0562 | 496903 | 496691 |
| MJ0565 | 502486 | 502046 |
| MJ0567 | 504742 | 504497 |
| MJ0568 | 504847 | 505221 |
| MJ0570 | 506837 | 506112 |
| MJ0572 | 509860 | 510117 |
| MJ0573 | 510262 | 510828 |
| MJ0574 | 510865 | 511143 |
| MJ0575 | 511121 | 511807 |
| MJ0580 | 515428 | 515075 |
| MJ0581 | 515692 | 515937 |
| MJ0582 | 515940 | 516323 |
| MJ0583 | 516393 | 516563 |
| MJ0584 | 516563 | 517657 |
| MJ0585 | 517680 | 518294 |
| MJ0586 | 518563 | 519057 |
| MJ0587 | 519994 | 519536 |
| MJ0589 | 521451 | 521768 |
| MJ0592 | 525620 | 526357 |
| MJ0594 | 526886 | 527392 |
| MJ0596 | 528074 | 528475 |
| MJ0597 | 528539 | 529612 |
| MJ0599 | 530524 | 531120 |
| MJ0602 | 533752 | 532970 |
| MJ0604 | 535443 | 535144 |
| MJ0605 | 535634 | 535443 |
| MJ0606 | 536194 | 535922 |
| MJ0607 | 536435 | 536199 |
| MJ0610 | 540394 | 539093 |
| MJ0614 | 545444 | 545061 |
| MJ0618 | 547877 | 547584 |
| MJ0619 | 549378 | 547861 |

TABLE 2-continued

| | | |
|---|---|---|
| MJ0621 | 551088 | 550573 |
| MJ0623 | 552787 | 553362 |
| MJ0625 | 553606 | 554613 |
| MJ0626 | 554709 | 555335 |
| MJ0627 | 555369 | 555719 |
| MJ0628 | 555715 | 556203 |
| MJ0629 | 556208 | 556849 |
| MJ0632 | 558292 | 559380 |
| MJ0634 | 562682 | 564565 |
| MJ0635 | 564797 | 565636 |
| MJ0638 | 568586 | 567912 |
| MJ0639 | 568870 | 568586 |
| MJ0642 | 571462 | 572451 |
| MJ0645 | 574498 | 574743 |
| MJ0646 | 574757 | 575248 |
| MJ0647 | 575457 | 575296 |
| MJ0648 | 575881 | 575441 |
| MJ0650 | 577458 | 579521 |
| MJ0652 | 580869 | 580471 |
| MJ0659 | 585626 | 586039 |
| MJ0660 | 586366 | 586136 |
| MJ0661 | 587014 | 586496 |
| MJ0662 | 587657 | 587007 |
| MJ0664 | 589291 | 590163 |
| MJ0665 | 590629 | 590180 |
| MJ0668 | 594556 | 594314 |
| MJ0670 | 596945 | 595887 |
| MJ0675 | 601925 | 600753 |
| MJ0678 | 605240 | 604263 |
| MJ0683 | 611696 | 610920 |
| MJ0686 | 615407 | 613668 |
| MJ0687 | 616482 | 615478 |
| MJ0688 | 616670 | 617110 |
| MJ0690 | 617965 | 617375 |
| MJ0691 | 618300 | 617974 |
| MJ0694 | 620244 | 621365 |
| MJ0695 | 621809 | 621486 |
| MJ0696 | 622409 | 621933 |
| MJ0699 | 625837 | 624698 |
| MJ0700 | 625851 | 626822 |
| MJ0701 | 626831 | 628063 |
| MJ0702 | 628050 | 629831 |
| MJ0703 | 629859 | 630536 |
| MJ0704 | 631069 | 632199 |
| MJ0706 | 633440 | 634081 |
| MJ0708 | 634868 | 634425 |
| MJ0711 | 643995 | 644960 |
| MJ0712 | 645967 | 644963 |
| MJ0714 | 648530 | 648880 |
| MJ0716 | 650013 | 650270 |
| MJ0717 | 650815 | 650459 |
| MJ0724 | 657809 | 657189 |
| MJ0730 | 663605 | 663048 |
| MJ0731 | 664213 | 663620 |
| MJ0733 | 665883 | 665521 |
| MJ0737 | 667834 | 667652 |
| MJ0738 | 668149 | 667877 |
| MJ0739 | 668627 | 668175 |
| MJ0742 | 669819 | 669496 |
| MJ0745 | 672208 | 671675 |
| MJ0747 | 673416 | 672961 |
| MJ0749 | 675903 | 675151 |
| MJ0750 | 676710 | 675997 |
| MJ0751 | 677628 | 676795 |
| MJ0752 | 677942 | 677715 |
| MJ0753 | 678766 | 678146 |
| MJ0754 | 679347 | 678775 |
| MJ0755 | 680644 | 679619 |
| MJ0756 | 681296 | 680889 |
| MJ0757 | 682155 | 681424 |
| MJ0758 | 682653 | 682213 |
| MJ0759 | 683029 | 682700 |
| MJ0760 | 683871 | 683047 |
| MJ0761 | 684833 | 684072 |
| MJ0763 | 686251 | 685889 |
| MJ0764 | 686611 | 686264 |
| MJ0766 | 688821 | 688729 |
| MJ0767 | 689531 | 689100 |
| MJ0768 | 689589 | 690335 |
| MJ0769 | 690987 | 690481 |
| MJ0770 | 691651 | 690983 |
| MJ0772 | 692429 | 693487 |
| MJ0773 | 694540 | 694016 |
| MJ0774 | 695228 | 696454 |
| MJ0775 | 696438 | 697379 |
| MJ0776 | 697375 | 698523 |
| MJ0777 | 698474 | 699046 |
| MJ0778 | 699097 | 699603 |
| MJ0779 | 700509 | 699613 |
| MJ0780 | 701537 | 700533 |
| MJ0783 | 706171 | 706737 |
| MJ0786 | 710078 | 710620 |
| MJ0788 | 712303 | 712539 |
| MJ0789 | 712625 | 712972 |
| MJ0790 | 713001 | 713696 |
| MJ0792 | 715511 | 715777 |
| MJ0793 | 716398 | 716931 |
| MJ0794 | 716992 | 717405 |
| MJ0795 | 717488 | 718999 |
| MJ0797 | 720647 | 721759 |
| MJ0798 | 721779 | 722780 |
| MJ0799 | 722786 | 723667 |
| MJ0801 | 725037 | 726173 |
| MJ0802 | 726398 | 726961 |
| MJ0803 | 726984 | 727499 |
| MJ0804 | 727530 | 728387 |
| MJ0805 | 728332 | 728994 |
| MJ0807 | 730149 | 730670 |
| MJ0808 | 730806 | 731804 |
| MJ0809 | 733025 | 733525 |
| MJ0810 | 733584 | 734255 |
| MJ0811 | 735675 | 734359 |
| MJ0815 | 739584 | 738697 |
| MJ0816 | 740542 | 739652 |
| MJ0817 | 741119 | 740502 |
| MJ0818 | 741733 | 741125 |
| MJ0819 | 742225 | 741899 |
| MJ0820 | 742295 | 742191 |
| MJ0821 | 742765 | 742598 |
| MJ0823 | 744830 | 745600 |
| MJ0826 | 747462 | 747875 |
| MJ0830 | 750568 | 750101 |
| MJ0831 | 750950 | 752245 |
| MJ0833 | 758976 | 758239 |
| MJ0834 | 759796 | 759083 |
| MJ0835 | 760901 | 759822 |
| MJ0836 | 762786 | 762430 |
| MJ0837 | 762860 | 763606 |
| MJ0838 | 764466 | 764816 |
| MJ0839 | 765906 | 764857 |
| MJ0840 | 765992 | 766972 |
| MJ0841 | 768225 | 766981 |
| MJ0856 | 780538 | 779996 |
| MJ0857 | 781920 | 781099 |
| MJ0858 | 782318 | 781980 |
| MJ0859 | 782837 | 782355 |
| MJ0865 | 788311 | 789585 |
| MJ0871 | 795055 | 795975 |
| MJ0872 | 797236 | 796022 |
| MJ0874 | 798213 | 798491 |
| MJ0875 | 798611 | 800854 |
| MJ0878 | 803147 | 804388 |
| MJ0880 | 805402 | 806325 |
| MJ0883 | 808397 | 809404 |
| MJ0887 | 818880 | 818209 |
| MJ0889 | 819606 | 821000 |
| MJ0890 | 821429 | 821019 |
| MJ0894 | 824064 | 824486 |
| MJ0895 | 824467 | 825492 |
| MJ0896 | 825552 | 825953 |
| MJ0897 | 825946 | 826362 |
| MJ0898 | 826495 | 826932 |
| MJ0899 | 826954 | 827643 |
| MJ0900 | 827668 | 829308 |
| MJ0901 | 829430 | 830998 |
| MJ0902 | 831028 | 831729 |
| MJ0903 | 831942 | 833855 |
| MJ0904 | 834299 | 834547 |

TABLE 2-continued

| | | |
|---|---|---|
| MJ0905 | 834622 | 834954 |
| MJ0906 | 834959 | 836056 |
| MJ0907 | 836917 | 836072 |
| MJ0909 | 840933 | 841220 |
| MJ0910 | 841954 | 841433 |
| MJ0912 | 843688 | 844416 |
| MJ0914 | 845908 | 845783 |
| MJ0915 | 847507 | 846707 |
| MJ0916 | 847875 | 847609 |
| MJ0917 | 847950 | 849671 |
| MJ0919 | 850996 | 850550 |
| MJ0921 | 852470 | 851571 |
| MJ0923 | 853368 | 854258 |
| MJ0925 | 855529 | 855212 |
| MJ0926 | 856378 | 856638 |
| MJ0933 | 862692 | 863390 |
| MJ0935 | 864824 | 865447 |
| MJ0936 | 865545 | 866042 |
| MJ0938 | 868207 | 867473 |
| MJ0939 | 868278 | 869102 |
| MJ0943 | 875111 | 873870 |
| MJ0944 | 875300 | 875659 |
| MJ0945 | 876358 | 875687 |
| MJ0948 | 881231 | 880668 |
| MJ0949 | 881637 | 881269 |
| MJ0950 | 882370 | 881684 |
| MJ0951 | 883634 | 882570 |
| MJ0953 | 884488 | 884787 |
| MJ0954 | 886106 | 884802 |
| MJ0956 | 887437 | 888216 |
| MJ0957 | 888219 | 889268 |
| MJ0958 | 889276 | 890553 |
| MJ0962 | 894937 | 895320 |
| MJ0966 | 899875 | 901197 |
| MJ0967 | 901940 | 901326 |
| MJ0968 | 901996 | 902814 |
| MJ0969 | 903935 | 903126 |
| MJ0970 | 904627 | 904199 |
| MJ0971 | 904756 | 905844 |
| MJ0972 | 905808 | 906488 |
| MJ0973 | 907728 | 906496 |
| MJ0974 | 908172 | 907741 |
| MJ0975 | 908365 | 908162 |
| MJ0976 | 908463 | 909560 |
| MJ0977 | 909594 | 911000 |
| MJ0978 | 911359 | 911688 |
| MJ0979 | 912309 | 911719 |
| MJ0981 | 914246 | 913641 |
| MJ0986 | 917606 | 917373 |
| MJ0987 | 917909 | 918247 |
| MJ0988 | 918361 | 919347 |
| MJ0991 | 920189 | 920608 |
| MJ0992 | 920924 | 921142 |
| MJ0995 | 924316 | 923636 |
| MJ0997 | 925109 | 925719 |
| MJ0998 | 926425 | 926012 |
| MJ1002 | 930965 | 931891 |
| MJ1004 | 933349 | 933990 |
| MJ1005 | 933994 | 934386 |
| MJ1006 | 934412 | 935437 |
| MJ1010 | 941079 | 939958 |
| MJ1011 | 941860 | 941471 |
| MJ1016 | 946060 | 946941 |
| MJ1017 | 946934 | 947542 |
| MJ1020 | 950418 | 951194 |
| MJ1021 | 951732 | 951244 |
| MJ1022 | 953674 | 951968 |
| MJ1024 | 954536 | 955744 |
| MJ1025 | 956917 | 955751 |
| MJ1028 | 959569 | 961611 |
| MJ1030 | 962492 | 962932 |
| MJ1032 | 963985 | 965082 |
| MJ1034 | 966050 | 966310 |
| MJ1036 | 967587 | 968276 |
| MJ1049 | 986885 | 987367 |
| MJ1050 | 987438 | 987968 |
| MJ1052 | 989793 | 989503 |
| MJ1053 | 990349 | 989861 |
| MJ1060 | 1000457 | 1002067 |
| MJ1067 | 1008238 | 1008681 |
| MJ1069 | 1010805 | 1009630 |
| MJ1070 | 1011399 | 1010929 |
| MJ1071 | 1012337 | 1011399 |
| MJ1072 | 1012709 | 1012362 |
| MJ1073 | 1013688 | 1012879 |
| MJ1074 | 1014135 | 1013800 |
| MJ1076 | 1016646 | 1015636 |
| MJ1077 | 1018245 | 1016683 |
| MJ1078 | 1019039 | 1018338 |
| MJ1079 | 1020506 | 1019316 |
| MJ1080 | 1021091 | 1020687 |
| MJ1082 | 1021657 | 1022016 |
| MJ1083 | 1022089 | 1022667 |
| MJ1085 | 1023633 | 1025159 |
| MJ1086 | 1025159 | 1026178 |
| MJ1092 | 1030102 | 1030743 |
| MJ1094 | 1033051 | 1031897 |
| MJ1095 | 1034350 | 1033088 |
| MJ1098 | 1039265 | 1038627 |
| MJ1099 | 1040323 | 1039619 |
| MJ1103 | 1043990 | 1043727 |
| MJ1106 | 1046606 | 1046052 |
| MJ1107 | 1047073 | 1046627 |
| MJ1110 | 1052574 | 1051117 |
| MJ1111 | 1053691 | 1052540 |
| MJ1112 | 1053818 | 1053645 |
| MJ1114 | 1055795 | 1055220 |
| MJ1117 | 1058450 | 1059037 |
| MJ1118 | 1059065 | 1059331 |
| MJ1120 | 1060339 | 1061175 |
| MJ1121 | 1061532 | 1061251 |
| MJ1122 | 1061729 | 1061508 |
| MJ1123 | 1061809 | 1062423 |
| MJ1125 | 1066578 | 1066399 |
| MJ1126 | 1067325 | 1068140 |
| MJ1127 | 1068204 | 1069043 |
| MJ1128 | 1069964 | 1069050 |
| MJ1132 | 1073401 | 1073048 |
| MJ1134 | 1075567 | 1074881 |
| MJ1137 | 1078625 | 1078035 |
| MJ1138 | 1078694 | 1079215 |
| MJ1139 | 1080031 | 1079336 |
| MJ1140 | 1080732 | 1080049 |
| MJ1141 | 1080810 | 1081406 |
| MJ1143 | 1082498 | 1083604 |
| MJ1144 | 1084575 | 1083607 |
| MJ1145 | 1085112 | 1084918 |
| MJ1147 | 1086431 | 1087786 |
| MJ1150 | 1088688 | 1089230 |
| MJ1151 | 1089352 | 1089681 |
| MJ1152 | 1089693 | 1089902 |
| MJ1153 | 1089902 | 1090087 |
| MJ1154 | 1091598 | 1090246 |
| MJ1157 | 1097614 | 1098636 |
| MJ1158 | 1097631 | 1097245 |
| MJ1159 | 1098676 | 1100610 |
| MJ1161 | 1102129 | 1102629 |
| MJ1163 | 1104052 | 1104747 |
| MJ1164 | 1106045 | 1105095 |
| MJ1172 | 1111539 | 1111781 |
| MJ1173 | 1111785 | 1112066 |
| MJ1177 | 1117451 | 1118467 |
| MJ1179 | 1118839 | 1119285 |
| MJ1180 | 1119545 | 1119979 |
| MJ1181 | 1120081 | 1120677 |
| MJ1182 | 1121087 | 1122184 |
| MJ1183 | 1122200 | 1122670 |
| MJ1184 | 1122741 | 1123160 |
| MJ1185 | 1125032 | 1123167 |
| MJ1186 | 1125194 | 1126231 |
| MJ1188 | 1127047 | 1126238 |
| MJ1189 | 1128908 | 1128060 |
| MJ1198 | 1142323 | 1144605 |
| MJ1199 | 1145059 | 1144631 |
| MJ1205 | 1148679 | 1148371 |
| MJ1206 | 1149937 | 1148675 |
| MJ1207 | 1150577 | 1151254 |
| MJ1209 | 1154047 | 1152613 |

TABLE 2-continued

| | | |
|---|---|---|
| MJ1210 | 1154918 | 1154148 |
| MJ1211 | 1155290 | 1154943 |
| MJ1213 | 1156520 | 1156191 |
| MJ1215 | 1159884 | 1159639 |
| MJ1216 | 1160233 | 1159871 |
| MJ1217 | 1160540 | 1160247 |
| MJ1219 | 1162177 | 1161875 |
| MJ1221 | 1164080 | 1164958 |
| MJ1222 | 1165703 | 1164984 |
| MJ1223 | 1165956 | 1165681 |
| MJ1224 | 1167016 | 1166600 |
| MJ1230 | 1173450 | 1173235 |
| MJ1232 | 1176334 | 1175447 |
| MJ1233 | 1176475 | 1177311 |
| MJ1234 | 1178669 | 1177947 |
| MJ1239 | 1184644 | 1185318 |
| MJ1240 | 1185617 | 1185327 |
| MJ1241 | 1185877 | 1185644 |
| MJ1243 | 1187992 | 1187624 |
| MJ1244 | 1188410 | 1188087 |
| MJ1245 | 1188760 | 1188425 |
| MJ1248 | 1191184 | 1190723 |
| MJ1249 | 1191367 | 1192449 |
| MJ1250 | 1192973 | 1193731 |
| MJ1254 | 1197164 | 1197400 |
| MJ1255 | 1197430 | 1198611 |
| MJ1256 | 1198911 | 1199543 |
| MJ1257 | 1199543 | 1200589 |
| MJ1262 | 1204364 | 1205530 |
| MJ1272 | 1216145 | 1216633 |
| MJ1278 | 1223720 | 1223184 |
| MJ1279 | 1224266 | 1223724 |
| MJ1280 | 1224460 | 1224930 |
| MJ1281 | 1224854 | 1227994 |
| MJ1282 | 1228714 | 1229769 |
| MJ1283 | 1231676 | 1231017 |
| MJ1284 | 1232029 | 1231667 |
| MJ1285 | 1232580 | 1232029 |
| MJ1286 | 1234269 | 1232587 |
| MJ1287 | 1235086 | 1234319 |
| MJ1288 | 1235901 | 1235155 |
| MJ1289 | 1236778 | 1236284 |
| MJ1290 | 1237713 | 1236778 |
| MJ1291 | 1238448 | 1237729 |
| MJ1292 | 1238662 | 1241124 |
| MJ1293 | 1241174 | 1241866 |
| MJ1295 | 1243251 | 1242847 |
| MJ1301 | 1250120 | 1248921 |
| MJ1302 | 1250541 | 1250149 |
| MJ1304 | 1252617 | 1252162 |
| MJ1305 | 1253036 | 1252596 |
| MJ1306 | 1253300 | 1253052 |
| MJ1307 | 1254110 | 1253325 |
| MJ1308 | 1254426 | 1254115 |
| MJ1309 | 1255877 | 1254459 |
| MJ1310 | 1256325 | 1255942 |
| MJ1311 | 1256457 | 1257287 |
| MJ1312 | 1257321 | 1258283 |
| MJ1313 | 1258388 | 1259596 |
| MJ1315 | 1260519 | 1261589 |
| MJ1316 | 1261606 | 1261833 |
| MJ1317 | 1263015 | 1261822 |
| MJ1318 | 1264868 | 1263063 |
| MJ1320 | 1268194 | 1267802 |
| MJ1321 | 1270356 | 1268218 |
| MJ1322 | 1273392 | 1270378 |
| MJ1323 | 1274489 | 1273392 |
| MJ1325 | 1275428 | 1275694 |
| MJ1327 | 1277081 | 1277815 |
| MJ1330 | 1280424 | 1280792 |
| MJ1331 | 1281220 | 1280801 |
| MJ1333 | 1282515 | 1282766 |
| MJ1336 | 1284800 | 1285282 |
| MJ1337 | 1285743 | 1286216 |
| MJ1339 | 1287389 | 1287850 |
| MJ1340 | 1287925 | 1288266 |
| MJ1341 | 1289221 | 1288286 |
| MJ1342 | 1289457 | 1289798 |
| MJ1345 | 1291918 | 1292841 |
| MJ1348 | 1295149 | 1296126 |
| MJ1350 | 1298227 | 1297454 |
| MJ1354 | 1304338 | 1304772 |
| MJ1355 | 1304858 | 1306531 |
| MJ1356 | 1306729 | 1307295 |
| MJ1358 | 1309040 | 1308648 |
| MJ1359 | 1309889 | 1309164 |
| MJ1360 | 1310249 | 1309953 |
| MJ1361 | 1310355 | 1311230 |
| MJ1364 | 1313354 | 1314619 |
| MJ1369 | 1318564 | 1319028 |
| MJ1370 | 1319061 | 1320044 |
| MJ1371 | 1320053 | 1320775 |
| MJ1373 | 1321601 | 1322086 |
| MJ1374 | 1322262 | 1322954 |
| MJ1379 | 1328524 | 1328823 |
| MJ1380 | 1328819 | 1329052 |
| MJ1382 | 1331473 | 1331036 |
| MJ1383 | 1332364 | 1331597 |
| MJ1384 | 1333177 | 1332596 |
| MJ1385 | 1333741 | 1333205 |
| MJ1386 | 1333877 | 1334008 |
| MJ1387 | 1335433 | 1334297 |
| MJ1389 | 1337813 | 1337412 |
| MJ1393 | 1341979 | 1343802 |
| MJ1394 | 1343895 | 1346852 |
| MJ1395 | 1347176 | 1347571 |
| MJ1396 | 1347707 | 1356388 |
| MJ1397 | 1356457 | 1357905 |
| MJ1398 | 1358183 | 1359355 |
| MJ1399 | 1359929 | 1359339 |
| MJ1400 | 1360142 | 1359942 |
| MJ1401 | 1360259 | 1362682 |
| MJ1402 | 1364357 | 1363320 |
| MJ1403 | 1365794 | 1364673 |
| MJ1404 | 1366111 | 1367364 |
| MJ1405 | 1367427 | 1367639 |
| MJ1407 | 1368408 | 1368794 |
| MJ1409 | 1370733 | 1369939 |
| MJ1410 | 1371310 | 1370834 |
| MJ1412 | 1373210 | 1374703 |
| MJ1414 | 1375807 | 1375094 |
| MJ1416 | 1378350 | 1376995 |
| MJ1419 | 1382016 | 1381714 |
| MJ1423 | 1394263 | 1393208 |
| MJ1424 | 1394481 | 1395002 |
| MJ1427 | 1396680 | 1397633 |
| MJ1428 | 1397643 | 1399343 |
| MJ1429 | 1399343 | 1400842 |
| MJ1431 | 1401322 | 1402398 |
| MJ1433 | 1402914 | 1403654 |
| MJ1435 | 1404402 | 1404614 |
| MJ1436 | 1404758 | 1405048 |
| MJ1437 | 1405055 | 1405738 |
| MJ1440 | 1407288 | 1408133 |
| MJ1442 | 1412130 | 1412735 |
| MJ1443 | 1412784 | 1413104 |
| MJ1445 | 1414331 | 1414858 |
| MJ1447 | 1415840 | 1416982 |
| MJ1448 | 1416982 | 1418571 |
| MJ1449 | 1418577 | 1419686 |
| MJ1450 | 1419699 | 1420811 |
| MJ1451 | 1420869 | 1422320 |
| MJ1452 | 1422616 | 1423392 |
| MJ1453 | 1423398 | 1423973 |
| MJ1455 | 1425643 | 1424729 |
| MJ1457 | 1427021 | 1427422 |
| MJ1458 | 1427487 | 1428140 |
| MJ1460 | 1430419 | 1429943 |
| MJ1461 | 1431156 | 1430560 |
| MJ1462 | 1431506 | 1431258 |
| MJ1463 | 1432201 | 1431530 |
| MJ1466 | 1436397 | 1435756 |
| MJ1467 | 1436562 | 1437008 |
| MJ1468 | 1437029 | 1440055 |
| MJ1469 | 1440055 | 1440279 |
| MJ1470 | 1440747 | 1442618 |
| MJ1471 | 1442618 | 1443151 |
| MJ1472 | 1443165 | 1444796 |

TABLE 2-continued

| | | |
|---|---|---|
| MJ1475 | 1446447 | 1446821 |
| MJ1477 | 1447530 | 1448537 |
| MJ1478 | 1449448 | 1448540 |
| MJ1480 | 1451452 | 1452720 |
| MJ1481 | 1452735 | 1453373 |
| MJ1483 | 1454337 | 1454783 |
| MJ1484 | 1454768 | 1455217 |
| MJ1487 | 1459016 | 1460293 |
| MJ1488 | 1460315 | 1461493 |
| MJ1491 | 1465684 | 1466055 |
| MJ1492 | 1466067 | 1466534 |
| MJ1493 | 1466552 | 1467235 |
| MJ1495 | 1468532 | 1469377 |
| MJ1496 | 1469370 | 1469711 |
| MJ1497 | 1469711 | 1470748 |
| MJ1499 | 1472128 | 1471649 |
| MJ1500 | 1472920 | 1472363 |
| MJ1501 | 1473615 | 1472947 |
| MJ1503 | 1474982 | 1474587 |
| MJ1506 | 1479963 | 1478767 |
| MJ1507 | 1480030 | 1481214 |
| MJ1509 | 1482024 | 1482482 |
| MJ1510 | 1483084 | 1482506 |
| MJ1511 | 1483234 | 1483572 |
| MJ1513 | 1489601 | 1488606 |
| MJ1514 | 1489692 | 1490078 |
| MJ1515 | 1490084 | 1491148 |
| MJ1516 | 1491173 | 1491466 |
| MJ1517 | 1492030 | 1492863 |
| MJ1518 | 1492917 | 1493975 |
| MJ1519 | 1494094 | 1497618 |
| MJ1520 | 1498588 | 1497656 |
| MJ1521 | 1498905 | 1500170 |
| MJ1524 | 1501404 | 1501727 |
| MJ1525 | 1501702 | 1504500 |
| MJ1527 | 1505607 | 1505281 |
| MJ1535 | 1512870 | 1513766 |
| MJ1537 | 1515742 | 1514714 |
| MJ1539 | 1516728 | 1517042 |
| MJ1540 | 1517209 | 1517466 |
| MJ1542 | 1521169 | 1518746 |
| MJ1544 | 1523759 | 1522470 |
| MJ1545 | 1523900 | 1524592 |
| MJ1547 | 1525820 | 1526005 |
| MJ1548 | 1526062 | 1526427 |
| MJ1550 | 1527849 | 1528031 |
| MJ1551 | 1528046 | 1528216 |
| MJ1553 | 1528749 | 1529240 |
| MJ1554 | 1529326 | 1531191 |
| MJ1556 | 1532701 | 1533636 |
| MJ1557 | 1533644 | 1534390 |
| MJ1558 | 1534666 | 1534397 |
| MJ1559 | 1534699 | 1535262 |
| MJ1561 | 1538168 | 1536510 |
| MJ1562 | 1539331 | 1538168 |
| MJ1563 | 1539812 | 1539345 |
| MJ1564 | 1540186 | 1540695 |
| MJ1565 | 1540699 | 1542237 |
| MJ1566 | 1543572 | 1542232 |
| MJ1567 | 1544072 | 1543557 |
| MJ1568 | 1544632 | 1544078 |
| MJ1570 | 1545637 | 1545981 |
| MJ1571 | 1546111 | 1546986 |
| MJ1573 | 1548452 | 1548270 |
| MJ1576 | 1551559 | 1552164 |
| MJ1577 | 1552197 | 1553990 |
| MJ1579 | 1555146 | 1554937 |
| MJ1580 | 1555498 | 1555127 |
| MJ1583 | 1557431 | 1557808 |
| MJ1584 | 1558268 | 1557816 |
| MJ1585 | 1559172 | 1558255 |
| MJ1587 | 1560732 | 1561265 |
| MJ1588 | 1561285 | 1561620 |
| MJ1589 | 1561657 | 1562379 |
| MJ1590 | 1562770 | 1563084 |
| MJ1595 | 1567357 | 1566332 |
| MJ1598 | 1572075 | 1571026 |
| MJ1599 | 1572924 | 1572094 |
| MJ1600 | 1573002 | 1573532 |
| MJ1601 | 1573539 | 1574018 |
| MJ1604 | 1578693 | 1577308 |
| MJ1608 | 1582917 | 1583126 |
| MJ1609 | 1583168 | 1584289 |
| MJ1613 | 1589822 | 1589058 |
| MJ1614 | 1590582 | 1589830 |
| MJ1615 | 1591350 | 1590586 |
| MJ1617 | 1593103 | 1593381 |
| MJ1618 | 1593786 | 1593397 |
| MJ1620 | 1594531 | 1596084 |
| MJ1621 | 1596297 | 1596127 |
| MJ1622 | 1597169 | 1597719 |
| MJ1623 | 1597939 | 1599474 |
| MJ1624 | 1599991 | 1599602 |
| MJ1626 | 1602381 | 1600087 |
| MJ1627 | 1604683 | 1604231 |
| MJ1628 | 1606127 | 1604784 |
| MJ1629 | 1607293 | 1606418 |
| MJ1630 | 1610737 | 1607330 |
| MJ1631 | 1611184 | 1612740 |
| MJ1632 | 1612697 | 1613446 |
| MJ1633 | 1614897 | 1613467 |
| MJ1634 | 1615733 | 1615011 |
| MJ1635 | 1615933 | 1617174 |
| MJ1637 | 1618268 | 1619686 |
| MJ1638 | 1620457 | 1619678 |
| MJ1639 | 1620605 | 1621036 |
| MJ1640 | 1621671 | 1621057 |
| MJ1641 | 1622664 | 1621804 |
| MJ1642 | 1623032 | 1623514 |
| MJ1644 | 1627146 | 1627667 |
| MJ1646 | 1628442 | 1629074 |
| MJ1650 | 1632586 | 1631435 |
| MJ1651 | 1633407 | 1632631 |
| MJ1653 | 1635797 | 1636951 |
| MJ1654 | 1637097 | 1637693 |
| MJ1657 | 1639687 | 1640427 |
| MJ1658 | 1640511 | 1640783 |
| MJ1659 | 1640800 | 1641870 |
| MJ1660 | 1641857 | 1643503 |
| MJ1664 | 1646502 | 1647179 |
| MJ1665 | 1648555 | 1647182 |
| MJ1666 | 1650080 | 1648686 |
| MJ1667 | 1651336 | 1650083 |
| MJ1668 | 1652321 | 1651194 |
| MJ1669 | 1653119 | 1652376 |
| MJ1670 | 1653547 | 1653149 |
| MJ1671 | 1653684 | 1653550 |
| MJ1672 | 1656206 | 1653807 |
| MJ1673 | 1656630 | 1656244 |
| MJ1674 | 1658539 | 1656638 |
| MJ1676 | 1659621 | 1660334 |
| MJ1678 | 1660939 | 1662126 |
| MJ1679 | 1662142 | 1662432 |
| MJ1680 | 1662411 | 1662866 |
| MJ1681 | 1663887 | 1662862 |
| MJECS01 | 1268 | 432 |
| MJECS02 | 4814 | 1272 |
| MJECS03 | 5192 | 4851 |
| MJECS04 | 5884 | 5459 |
| MJECS05 | 6365 | 6814 |
| MJECS06 | 7443 | 7009 |
| MJECS07 | 8765 | 7428 |
| MJECS08 | 11950 | 8738 |
| MJECS09 | 12641 | 11925 |
| MJECS10 | 14062 | 13181 |
| MJECS11 | 14404 | 15030 |
| MJECS12 | 16547 | 15411 |
| MJECL01 | 275 | 1048 |
| MJECL02 | 1474 | 1085 |
| MJECL03 | 1700 | 1377 |
| MJECL04 | 1865 | 3250 |
| MJECL05 | 3235 | 3450 |
| MJECL06 | 4170 | 3787 |
| MJECL07 | 5844 | 4561 |
| MJECL08 | 7415 | 5832 |
| MJECL09 | 7780 | 8103 |
| MJECL10 | 8107 | 8784 |
| MJECL11 | 8788 | 9159 |

TABLE 2-continued

| | | |
|---|---|---|
| MJECL12 | 9150 | 9887 |
| MJECL13 | 10678 | 12483 |
| MJECL14 | 14468 | 15427 |
| MJECL15 | 15420 | 16541 |
| MJECL16 | 16599 | 16811 |
| MJECL18 | 20873 | 21505 |
| MJECL19 | 21456 | 22019 |
| MJECL20 | 22829 | 23290 |
| MJECL21 | 24596 | 23298 |
| MJECL22 | 25120 | 24854 |
| MJECL23 | 27628 | 25136 |
| MJECL25 | 28835 | 29167 |
| MJECL26 | 30215 | 29178 |
| MJECL27 | 31077 | 30571 |
| MJECL28 | 35352 | 31534 |
| MJECL30 | 37621 | 37151 |
| MJECL31 | 37811 | 37599 |
| MJECL32 | 40153 | 38828 |
| MJECL33 | 41381 | 40125 |
| MJECL34 | 43121 | 42231 |
| MJECL35 | 45007 | 43115 |
| MJECL36 | 45921 | 45394 |
| MJECL37 | 46065 | 46865 |
| MJECL38 | 47997 | 47197 |
| MJECL39 | 49387 | 48329 |
| MJECL41 | 53908 | 52613 |
| MJECL43 | 57371 | 56187 |
| MJECL44 | 58339 | 57341 |

TABLE 3

Genes of *M. jannaschii* that contain inteins.

| Gene No. | Putative identification | No. of inteins |
|---|---|---|
| MJ0043 | Hypothetical protein (*Bacillus subtilis*) | 1 |
| MJ0262 | Putative translation initiation factor, FUN12/IF-2 family | 1 |
| MJ0542 | Phosphoenolpyruvate synthase | 1 |
| MJ0682 | Hypothetical protein (*Escherichia coli*) | 1 |
| MJ0782 | Transcription initiation factor IIB | 1 |
| MJ0832 | Anaerobic ribonucleoside-triphosphate reductase | 2 |
| MJ0885 | DNA-dependent DNA polymerase, family B | 2 |
| MJ1042 | DNA-dependent RNA polymerase, subunit A' | 1 |
| MJ1043 | DNA-dependent RNA polymerase, subunit A" | 1 |
| MJ1054 | UDP-glucose dehydrogenase | 1 |
| MJ1124 | Hypothetical protein (*Saccharomyces cerevisiae*) | 1 |
| MJ1420 | Glutamine-fructose-6-phosphate transaminase | 1 |
| MJ1422 | Replication factor C, 37-kD subunit | 3 |
| MJ1512 | Reverse gyrase | 1 |

While the present invention has been described in some detail for purposes of clarity and understanding, one skilled in the art will appreciate that various changes in form and detail can be made without departing from the true scope of the invention.

All patents, patent applications and publications recited herein are hereby incorporated by reference.

SEQUENCE LISTING

The patent contains a lengthy "Sequence Listing" section. A copy of the "Sequence Listing" is available in electronic form from the USPTO web site (http://seqdata.uspto.gov/sequence.html?DocID=5790914B9). An electronic copy of the "Sequence Listing" will also be available from the USPTO upon request and payment of the fee set forth in 37 CFR 1.19(b)(3).

What is claimed is:

1. An isolated polynucleotide comprising the nucleic acid sequence of ORF MJ0428, represented by nucleotides 1087456–1088655 of SEQ ID NO:1.

2. The isolated polynucleotide of claim 1, wherein said polynucleotide comprises a heterologous polynucleotide sequence.

3. The isolated polynucleotide of claim 2, wherein said heterologous polynucleotide sequence encodes a heterologous polypeptide.

4. A method for making a recombinant vector comprising inserting the isolated polynucleotide of claim 1 into a vector.

5. A nucleic acid sequence complimentary to the polynucleotide of claim 1.

6. A recombinant vector comprising the isolated polynucleotide of claim 1.

7. The recombinant vector of claim 6, wherein said polynucleotide is operably associated with a heterologous regulatory sequence that controls gene expression.

8. A recombinant host cell comprising the isolated polynucleotide of claim 1.

9. The recombinant host cell of claim 8, wherein said polynucleotide is operably associated with a heterologous regulatory sequence that controls gene expression.

10. An isolated polynucleotide fragment comprising a nucleic acid sequence which hybridizes under hybridization conditions, comprising hybridization in 5×SSC and 50% formamide at 50–65° C. and washing in a wash buffer consisting of 0.5×SSC at 50–65° C., to the complementary strand of ORF MJ0428, represented by nucleotides 1087456–1088655 of SEQ ID NO:1.

11. The isolated polynucleotide of claim 10, wherein said polynucleotide comprises a heterologous polynucleotide sequence.

12. The isolated polynucleotide of claim 11, wherein said heterologous polynucleotide sequence encodes a heterologous polypeptide.

13. A method for making a recombinant vector comprising inserting the isolated polynucleotide of claim 10 into a vector.

14. A nucleic acid sequence complimentary to the polynucleotide of claim 10.

15. A recombinant vector comprising the isolated polynucleotide of claim 10.

16. The recombinant vector of claim 15 wherein said polynucleotide is operably associated with a heterologous regulatory sequence that controls gene expression.

17. A recombinant host cell comprising the isolated polynucleotide of claim 10.

18. The recombinant host cell of claim 17, wherein said polynucleotide is operably associated with a heterologous regulatory sequence that controls gene expression.

19. An isolated polynucleotide for the detection of *Methanococcus jannaschii*, wherein said isolated polynucleotide comprises at least 30 contiguous nucteotides of the nucleic acid sequence of ORF MJ0428, represented by nucleotides 1087456–1088655 of SEQ ID NO:1.

20. The isolated polynucleotide of claim 19, wherein said polynucleotide comprises a heterologous polynucleotide sequence.

21. The isolated polynucleotide of claim 20, wherein said heterologous polynucleotide sequence encodes a heterologous polypeptide.

22. A method for making a recombinant vector comprising inserting the isolated polynucleotide of claim 19 into a vector.

23. A nucleic acid sequence complimentary to the polynucleotide of claim 19.

24. A recombinant vector comprising the isolated polynucleotide of claim 19.

25. The recombinant vector of claim 24, wherein said polynucleotide is operably associated with a heterologous regulatory sequence that controls gene expression.

26. A recombinant host cell comprising the isolated polynucleotide of claim 19.

27. The recombinant host cell of claim 26, wherein said polynucleotide is operably associated with a heterologous regulatory sequence that controls gene expression.

28. The isolated polynucleotide of claim 19, wherein said isolated polynucleotide comprises at least 40 contiguous nucleotides of the nucleic acid sequence of ORF MJ0428, represented by nucleotides 1087456–1088655 of SEQ ID NO:1.

29. A method for detecting *Methanococcus jannaschii* comprising:
   (a) contacting a biological sample with the isolated polynucleotide of claim 10 under conditions suitable for the hybridization of said polynucleotide to a nucleic acid molecule complementary thereto; and
   (b) detecting the presence or absence of *Methanococcus jannaschii* in the biological sample.

30. A method for detecting *Methanococcus jannaschii* comprising:
   (a) contacting said biological sample with the isolated polynucleotide of claim 19 under conditions suitable for the hybridization of said polynucleotide to a nucleic acid molecule complementary thereto; and
   (b) detecting the presence or absence of *Methanococcus jannaschii* in the biological sample.

31. A method for detecting *Methanococcus jannaschii* comprising:
   (a) contacting said biological sample with the isolated polynucleotide of claim 28 under conditions suitable for the hybridization of said polynucleotide to a nucleic acid molecule complementary thereto; and
   (b) detecting the presence or absence of *Methanococcus jannaschii* in the biological sample.

\* \* \* \* \*